US012501830B2

(12) United States Patent
Hong et al.

(10) Patent No.: US 12,501,830 B2
(45) Date of Patent: Dec. 16, 2025

(54) COMPOUND, SENSOR, SENSOR EMBEDDED DISPLAY PANEL, AND ELECTRONIC DEVICE

(71) Applicant: Samsung Electronics Co., Ltd., Suwon-si (KR)

(72) Inventors: Hye Rim Hong, Suwon-si (KR); Seon-Jeong Lim, Yongin-si (KR); Chul Joon Heo, Busan (KR); Kyung Bae Park, Hwaseong-si (KR); Sung Young Yun, Suwon-si (KR); Taejin Choi, Suwon-si (KR)

(73) Assignee: Samsung Display Co., Ltd., Gyeonggi-do (KR)

( * ) Notice: Subject to any disclaimer, the term of this patent is extended or adjusted under 35 U.S.C. 154(b) by 733 days.

(21) Appl. No.: 17/857,709

(22) Filed: Jul. 5, 2022

(65) Prior Publication Data

US 2023/0105575 A1 Apr. 6, 2023

(30) Foreign Application Priority Data

Jul. 29, 2021 (KR) ........................ 10-2021-0099855

(51) Int. Cl.
*H10K 85/60* (2023.01)
*C07D 209/86* (2006.01)
(Continued)

(52) U.S. Cl.
CPC ....... *H10K 85/6572* (2023.02); *C07D 209/86* (2013.01); *H10K 39/32* (2023.02); *H10K 65/00* (2023.02); *H10K 30/20* (2023.02)

(58) Field of Classification Search
CPC .... H10K 85/6572; H10K 39/32; H10K 65/00; H10K 30/20; H10K 59/40; H10K 30/00;
(Continued)

(56) References Cited

U.S. PATENT DOCUMENTS

| | | | |
|---|---|---|---|
| 9,412,952 | B2 | 8/2016 | Fukuzaki et al. |
| 9,614,163 | B2 | 4/2017 | Choi et al. |

(Continued)

FOREIGN PATENT DOCUMENTS

| | | | |
|---|---|---|---|
| EP | 2259358 | B1 | 10/2013 |
| KR | 2014-0039126 | A | 4/2014 |

(Continued)

OTHER PUBLICATIONS

Katsuhiko Ono "Synthesis and Electroluminescence Properties of fac-Tris(2-phenylpyridine)- iridium Derivatives Containing Hole-Trapping Moieties" Eur. J. Inorg. Chem. 2006, 3676-3683 (Year: 2006).*

*Primary Examiner* — Michael Y Sun
(74) *Attorney, Agent, or Firm* — Harness, Dickey & Pierce, P.L.C.

(57) ABSTRACT

A compound that may be applied to a sensor to improve electrical properties thereof is represented by Chemical Formula 1:

[Chemical Formula 1]

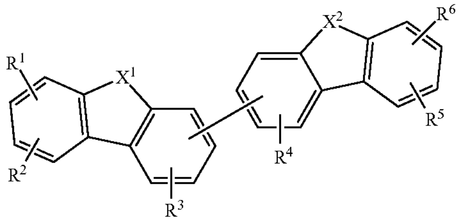

In Chemical Formula 1, each substituent is the same as defined in the detailed description.

24 Claims, 14 Drawing Sheets

(51) Int. Cl.

| | |
|---|---|
| ***H10K 39/32*** | (2023.01) |
| ***H10K 65/00*** | (2023.01) |
| *H10K 30/20* | (2023.01) |

(58) Field of Classification Search

CPC .. H10K 85/649; H10K 85/657; C07D 209/86; C07D 421/04; C07D 421/14; C07D 471/04; C07D 471/14; C07D 513/04; C07D 517/04; C07D 517/14; Y02E 10/549

See application file for complete search history.

(56) References Cited

U.S. PATENT DOCUMENTS

| | | | | |
|---|---|---|---|---|
| 9,842,998 | B2 | 12/2017 | Choi et al. | |
| 10,978,523 | B2 | 4/2021 | Park et al. | |
| 2014/0158859 | A1 | 6/2014 | Fukuzaki et al. | |
| 2015/0318511 | A1* | 11/2015 | Kim | H10K 85/615 257/40 |
| 2016/0111663 | A1 | 4/2016 | Kim et al. | |
| 2017/0170408 | A1 | 6/2017 | Park et al. | |
| 2020/0111851 | A1 | 4/2020 | Park et al. | |
| 2021/0135125 | A1 | 5/2021 | Hong et al. | |
| 2022/0123083 | A1* | 4/2022 | Han | H10K 59/60 |

FOREIGN PATENT DOCUMENTS

| | | | |
|---|---|---|---|
| KR | 2016-0010373 | A | 1/2016 |
| KR | 2016-0046296 | A | 4/2016 |
| KR | 2021-0054902 | A | 5/2021 |
| WO | WO-2020/053692 | A1 | 3/2020 |

* cited by examiner

COMPOUND, SENSOR, SENSOR EMBEDDED DISPLAY PANEL, AND ELECTRONIC DEVICE

CROSS-REFERENCE TO RELATED APPLICATION

This application claims priority to and the benefit of Korean Patent Application No. 10-2021-0099855 filed in the Korean Intellectual Property Office on Jul. 29, 2021, the entire contents of which are incorporated herein by reference.

BACKGROUND

1. Field

Compounds, sensors, sensor-embedded display panels, and electronic devices are disclosed.

2. Description of the Related Art

A photoelectric conversion device is a device that receives light and converts the light into an electrical signal, and may be applied to a sensor that senses light. A sensor is increasingly required to have a higher resolution, and accordingly, the pixel size is getting smaller. At present, a silicon photodiode is widely used, but it has a problem of deteriorated sensitivity since silicon photodiode has a smaller absorption area due to small pixels. Accordingly, an organic light absorbing material that can replace silicon is being studied. However, since the organic light absorbing material exhibits different characteristics from those of silicon due to high binding energy and a recombination behavior, the characteristics of the organic light absorbing material are difficult to precisely predict, and thus required properties of a sensor may not be easily controlled.

SUMMARY

Some example embodiments provide a compound that may be applied to (e.g., included in) a sensor to improve electrical properties thereof.

Some example embodiments provide a sensor including the compound.

Some example embodiments provide a sensor-embedded display panel in which the sensor is embedded.

Some example embodiments provide an electronic device including the compound, the sensor, or the sensor-embedded display panel.

According to some example embodiments, a compound that may be represented by Chemical Formula 1 is provided.

[Chemical Formula 1]

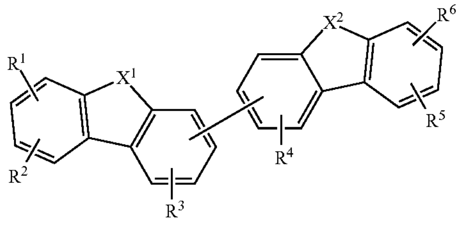

In Chemical Formula 1, $X^1$ and $X^2$ are different from each other and are each independently $CR^aR^b$, $SiR^cR^d$, or $NR^e$, $R^1$ to $R^6$ are each independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heterocyclic group, a halogen, a cyano group, —$NR^fR^g$, or any combination thereof, at least one of $R^1$ or $R^6$ is a substituted or unsubstituted C6 to C20 aryl group, a substituted or unsubstituted C3 to C20 heterocyclic group, —$NR^fR^g$, or any combination thereof, $R^a$ to $R^g$ are each independently hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof, $R^a$ and $R^b$ are each independently present or are linked to each other to form a ring, $R^c$ and $R^d$ are each independently present or are linked to each other to form a ring, and $R^f$ and $R^g$ are each independently present or are linked to each other to form a ring.

$R^1$ and $R^6$ may each independently be —$NR^fR^g$, wherein $R^f$ and $R^g$ may each be a substituted or unsubstituted C6 to C20 aryl group, and $R^f$ and $R^g$ may be linked to each other through a single bond, a substituted or unsubstituted C1 to C5 alkylene group, a substituted or unsubstituted C2 to C5 alkenylene group, a substituted or unsubstituted C6 to C20 arylene group, O, S, Se, Te, $CR^hR^i$, $SiR^jR^k$, or $GeR^lR^m$ to provide a ring, wherein $R^h$ to $R^m$ may each independently be hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof.

$X^1$ may be $CR^aR^b$ or $SiR^cR^d$, wherein $R^a$ to $R^d$ may each independently be hydrogen, a substituted or unsubstituted C1 to C30 alkyl group or a substituted or unsubstituted C6 to C20 aryl group, and $X^2$ may be $NR^e$, wherein $R^e$ may be a substituted or unsubstituted C6 to C20 aryl group.

A glass transition temperature of the compound may be greater than or equal to about 170° C., and a LUMO energy level of the compound may be less than or equal to about 2.80 eV.

The compound may be represented by Chemical Formula 1A.

[Chemical Formula 1A]

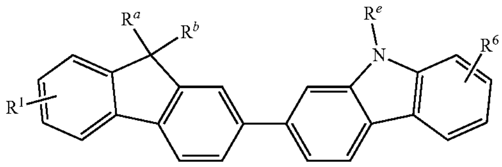

In Chemical Formula 1A, $R^a$ and $R^b$ are each independently hydrogen, a substituted or unsubstituted C1 to C30 alkyl group or a substituted or unsubstituted C6 to C20 aryl group, $R^e$ is a substituted or unsubstituted C6 to C20 aryl group, and $R^1$ and $R^6$ are each one group of a set of groups listed in Group 1,

[Group 1]

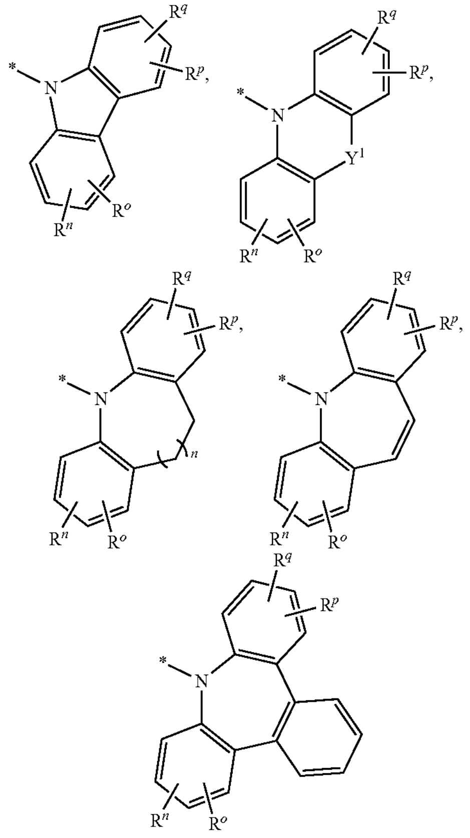

In Group 1, $Y^1$ may be O, S, Se, Te, $CR^hR^i$, $SiR^jR^k$, or $GeR^lR^m$, $R^h$ to $R^g$ may each independently be hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof, n may be an integer from 0 to 2, and

* may be a linking point with Chemical Formula 1A.

According to some example embodiments, a sensor may include a first electrode and a second electrode, a photoelectric conversion layer between the first electrode and the second electrode, and a buffer layer between the first electrode and the photoelectric conversion layer, wherein the buffer layer includes the compound represented by Chemical Formula 1.

The compound may be represented by Chemical Formula 1A.

The sensor may further include a semiconductor substrate, and the semiconductor substrate may include a circuit unit electrically connected to the first electrode or the second electrode.

According to some example embodiments, a sensor-embedded display panel may include a substrate, a light emitting element on the substrate, and a sensor on the substrate and in parallel with the light emitting element along an in-plane direction of the substrate such that the sensor and the light emitting element at least partially overlap in the in-plane direction, wherein the sensor includes a first electrode and a second electrode, a photoelectric conversion layer between the first electrode and the second electrode, and a buffer layer between the first electrode and the photoelectric conversion layer, wherein the buffer layer includes the compound represented by Chemical Formula 1.

The light emitting element may include first, second, and third light emitting elements arranged in parallel along the in-plane direction of the substrate and configured to emit light of different wavelength spectra in relation to each other, and the sensor may be configured to convert light emitted from at least one of the first, second, or third light emitting elements and then reflected by a recognition target to an electrical signal.

The compound may be represented by Chemical Formula 1A.

The light emitting element may include a third electrode and a fourth electrode, and a light emitting layer between the third electrode and the fourth electrode, wherein the second electrode of the sensor and the fourth electrode of the light emitting element may be a common electrode to which a common voltage is applied.

The sensor-embedded display panel may further include a first common auxiliary layer continuously formed as a single piece of material that extends between the third electrode and the light emitting layer and between the first electrode and the buffer layer.

The first common auxiliary layer may be in contact with the buffer layer in the sensor and the light emitting layer in the light emitting element, respectively.

The buffer layer may be thinner than the first common auxiliary layer.

The sensor-embedded display panel may further include a second common auxiliary layer continuously formed as a single piece of material that extends between the fourth electrode and the light emitting layer and between the second electrode and the photoelectric conversion layer.

The light emitting layer may include an organic light emitter, a quantum dot, a perovskite or any combination thereof, and the photoelectric conversion layer may include an organic photoelectric conversion material.

The light emitting element may include first, second and third light emitting elements configured to emit light in any one of a red wavelength spectrum, a green wavelength spectrum, or a blue wavelength spectrum, and the photoelectric conversion layer may be configured to absorb light of the same wavelength spectrum as light emitted from at least one of the first, second, or third light emitting elements.

The sensor-embedded display panel may include a display area configured to display a color and a non-display area excluding the display area, wherein the sensor may be in the non-display area.

The light emitting element may include first, second and third light emitting elements configured to emit light in any one of a red wavelength spectrum, a green wavelength spectrum, or a blue wavelength spectrum, the display area may include a plurality of first subpixels configured to display red and including the first light emitting element, a plurality of second subpixels configured to display green and including the second light emitting element, and a plurality of third subpixels configured to display blue and including the third light emitting element, and the sensor may be between at least two selected from the first subpixels, the second subpixels, or the third subpixels.

According to some example embodiments, an electronic device including the sensor and/or the sensor-embedded display panel is provided.

Electrical characteristics of the sensor may be improved.

DETAILED DESCRIPTION

Figure 1:
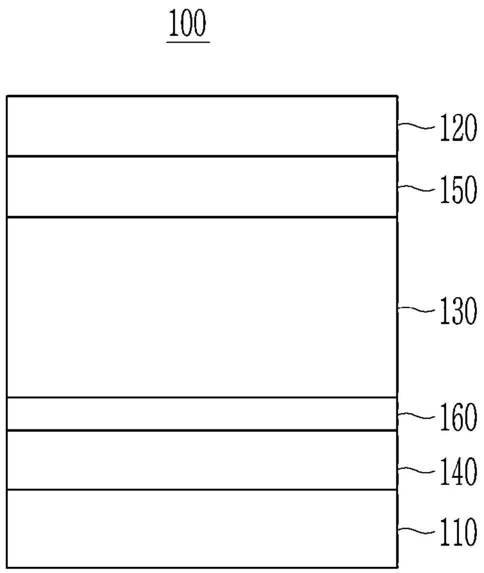
FIG. 1 is a cross-sectional view showing an example of a sensor according to some example embodiments.

Hereinafter, example embodiments of the present inventive concepts will be described in detail so that a person skilled in the art would understand the same. However, this inventive concepts may be embodied in many different forms and is not to be construed as limited to the exemplary embodiments set forth herein.

In the drawings, the thickness of layers, films, panels, regions, etc., are exaggerated for clarity. It will be understood that when an element such as a layer, film, region, or substrate is referred to as being "on" another element, it may be directly on the other element or intervening elements may also be present. In contrast, when an element is referred to as being "directly on" another element, there are no intervening elements present.

In the drawings, parts having no relationship with the description are omitted for clarity, and the same or similar constituent elements are indicated by the same reference numeral throughout the specification.

Hereinafter, the terms "lower portion" and "upper portion" are for convenience of description and do not limit the positional relationship.

As used herein, when a definition is not otherwise provided, "substituted" refers to replacement of hydrogen of a compound or a group by a substituent selected from a halogen, a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C30 alkyl group, a C2 to C30 alkenyl group, a C2 to C30 alkynyl group, a C6 to C30 aryl group, a C7 to C30 arylalkyl group, a C1 to C30 alkoxy group, a C1 to C20 heteroalkyl group, a C3 to C20 heterocyclic group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and any combination thereof.

As used herein, when a definition is not otherwise provided, "hetero" refers to one including 1 to 4 heteroatoms selected from N, O, S, Se, Te, Si, and P.

As used herein, when specific definition is not otherwise provided, an energy level refers to the highest occupied molecular orbital (HOMO) energy level and the lowest unoccupied molecular orbital (LUMO) energy level.

It will further be understood that when an element is referred to as being "on" another element, it may be above or beneath or adjacent (e.g., horizontally adjacent) to the other element.

It will be understood that elements and/or properties thereof (e.g., structures, surfaces, directions, or the like), which may be referred to as being "perpendicular," "parallel," "coplanar," or the like with regard to other elements and/or properties thereof (e.g., structures, surfaces, directions, or the like) may be "perpendicular," "parallel," "coplanar," or the like or may be "substantially perpendicular," "substantially parallel," "substantially coplanar," respectively, with regard to the other elements and/or properties thereof.

Elements and/or properties thereof (e.g., structures, surfaces, directions, or the like) that are "substantially perpendicular" with regard to other elements and/or properties thereof will be understood to be "perpendicular" with regard to the other elements and/or properties thereof within manufacturing tolerances and/or material tolerances and/or have a deviation in magnitude and/or angle from "perpendicular," or the like with regard to the other elements and/or properties thereof that is equal to or less than 10% (e.g., a. tolerance of ±10%).

Elements and/or properties thereof (e.g., structures, surfaces, directions, or the like) that are "substantially parallel" with regard to other elements and/or properties thereof will be understood to be "parallel" with regard to the other elements and/or properties thereof within manufacturing tolerances and/or material tolerances and/or have a deviation in magnitude and/or angle from "parallel," or the like with regard to the other elements and/or properties thereof that is equal to or less than 10% (e.g., a. tolerance of ±10%).

Elements and/or properties thereof (e.g., structures, surfaces, directions, or the like) that are "substantially coplanar" with regard to other elements and/or properties thereof will be understood to be "coplanar" with regard to the other elements and/or properties thereof within manufacturing tolerances and/or material tolerances and/or have a deviation in magnitude and/or angle from "coplanar," or the like with regard to the other elements and/or properties thereof that is equal to or less than 10% (e.g., a. tolerance of ±10%).

It will be understood that elements and/or properties thereof may be recited herein as being "the same" or "equal" as other elements, and it will be further understood that elements and/or properties thereof recited herein as being "identical" to, "the same" as, or "equal" to other elements may be "identical" to, "the same" as, or "equal" to or "substantially identical" to, "substantially the same" as or "substantially equal" to the other elements and/or properties thereof. Elements and/or properties thereof that are "substantially identical" to, "substantially the same" as or "substantially equal" to other elements and/or properties thereof will be understood to include elements and/or properties thereof that are identical to, the same as, or equal to the other elements and/or properties thereof within manufacturing tolerances and/or material tolerances. Elements and/or properties thereof that are identical or substantially identical to and/or the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same and/or identical encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

Hereinafter, when specific definition is not otherwise provided, a work function or an energy level is expressed as an absolute value from a vacuum level. In addition, when the work function or energy level is referred to be deep, high, or large, it may have a large absolute value based on "0 eV" of the vacuum level while when the work function or energy level is referred to be shallow, low, or small, it may have a small absolute value based on "0 eV" of the vacuum level. Further, the differences between the work function and/or the energy level may be values obtained by subtracting a small value of the absolute value from a large value of the absolute value.

Hereinafter, when a definition is not otherwise provided, the HOMO energy level may be evaluated with an amount of photoelectrons emitted by energy when irradiating UV light to a thin film using AC-2 (Hitachi) or AC-3 (Riken Keiki Co., Ltd.).

Hereinafter, when a definition is not otherwise provided, the LUMO energy level may be obtained by obtaining an energy bandgap using a UV-Vis spectrometer (Shimadzu Corporation), and then calculating the LUMO energy level from the energy bandgap and the already measured HOMO energy level.

Hereinafter, a compound according to some example embodiments is described.

The compound according to some example embodiments may have an asymmetric core including different fused rings from each other, and may be represented by Chemical Formula 1.

[Chemical Formula 1]

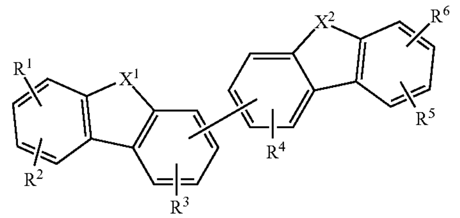

In Chemical Formula 1, $X^1$ and $X^2$ are different from each other and are each $CR^aR^b$, $SiR^cR^d$, or $NR^e$, $R^1$ to $R^6$ are each independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heterocyclic group, a halogen, a cyano group, $—NR^fR^g$, or any combination thereof, at least one of $R^1$ or $R^6$ is a substituted or unsubstituted C6 to C20 aryl group, a substituted or unsubstituted C3 to C20 heterocyclic group, $—NR^fR^g$, or any combination thereof, $R^a$ to $R^g$ are each independently hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof, $R^a$ and $R^b$ are each independently present or are linked to each other to form a ring, $R^c$ and $R^d$ are each independently present or are linked to each other to form a ring, and $R^f$ and $R^g$ are each independently present or are linked to each other to form a ring.

For example, in Chemical Formula 1, $X^1$ may be $CR^aR^b$ or $SiR^cR^d$ and $X^2$ may be $NR^e$. For example, $R^a$ to $R^d$ may each independently be hydrogen, a substituted or unsubstituted C1 to C30 alkyl group or a substituted or unsubstituted C6 to C20 aryl group, and for example $R^a$ to $R^d$ may each independently be hydrogen, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted hexyl group, a substituted or unsubstituted heptyl group, a substituted or unsubstituted octyl group, a substituted or unsubstituted phenyl group, a substituted or unsubstituted biphenyl group, a substituted or unsubstituted naphthyl group, a substituted or unsubstituted anthracenyl group, a substituted or unsubstituted phenanthryl group, or any combination thereof. For example, $R^e$ may be a substituted or unsubstituted C6 to C20 aryl group, and may be, for example, a substituted or unsubstituted phenyl group, a substituted or unsubstituted biphenyl group, a substituted or unsubstituted naphthyl group, a substituted or unsubstituted anthracenyl group, a substituted or unsubstituted phenanthryl group, or any combination thereof.

For example, in Chemical Formula 1, $X^1$ may be $CR^aR^b$, and $X^2$ may be $NR^e$.

For example, at least one of $R^1$ or $R^6$ may be $—NR^fR^g$, and for example $R^1$ and $R^6$ may each be $—NR^fR^g$. For example, $R^f$ and $R^g$ may be linked to each other to provide a ring, and for example, $R^f$ and $R^g$ may be linked to each other through a single bond, a substituted or unsubstituted C1 to C5 alkylene group, a substituted or unsubstituted C2 to C5 alkenylene group, a substituted or unsubstituted C6 to C20 arylene group, O, S, Se, Te, $CR^hR^i$, $SiR^jR^k$, or $GeR^lR^m$ to form a ring. $R^h$ to $R^m$ may each independently be hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof.

For example, at least one of $R^1$ or $R^6$ may be one group of a set of groups listed in Group 1, and for example, $R^1$ and $R^6$ may each be one group of the set of groups listed in Group 1.

[Group 1]

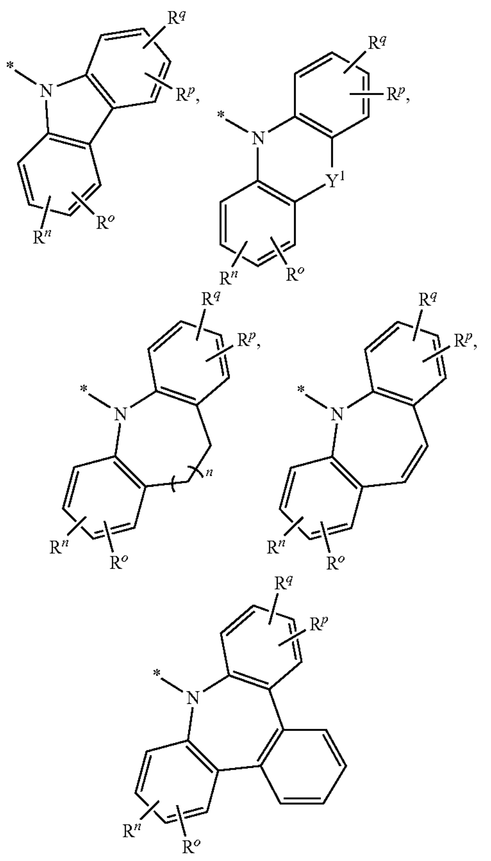

In Group 1, $Y^1$ may be O, S, Se, Te, $CR^hR^i$, $SiR^jR^k$, or $GeR^lR^m$, $R^h$ to $R^q$ may each independently be hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof, n may be an integer from 0 to 2 (e.g., n may be 0, 1, or 2), and

* may be a linking point with Chemical Formula 1.

For example, $R^2$ to $R^5$ may each independently be hydrogen, a substituted or unsubstituted C1 to C30 alkyl group, a halogen, a cyano group, or any combination thereof, and for example, $R^2$ to $R^5$ may each independently be hydrogen.

For example, the compound may be represented by Chemical Formula 1A.

[Chemical Formula 1A]

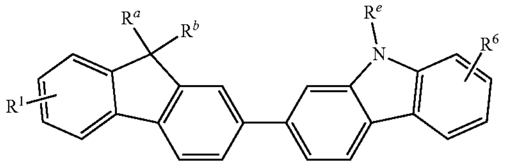

In Chemical Formula 1A, $R^a$, $R^b$, $R^e$, $R^1$, and $R^6$ are the same as described above. For example, $R^a$ and $R^b$ may each independently be hydrogen, a substituted or unsubstituted C1 to C30 alkyl group or a substituted or unsubstituted C6 to C20 aryl group, $R^e$ may be a substituted or unsubstituted C6 to C20 aryl group, and $R^1$ and $R^6$ may each be one group of the set of groups listed in Group 1, wherein, in Group 1, $Y^1$ is O, S, Se, Te, $CR^hR^i$, $SiR^jR^k$ or $GeR^lR^m$, $R^h$ to $R^q$ are each independently hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof, n is an integer of 0 to 2, and * is a linking point with Chemical Formula 1A.

For example, the compound may be represented by Chemical Formula 1AA.

[Chemical Formula 1AA]

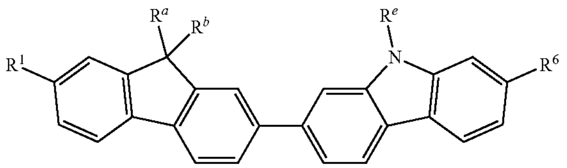

In Chemical Formula 1AA, $R^a$, $R^b$, $R^e$, $R^1$, and $R^6$ are the same as described above. For example, $R^a$ and $R^b$ may each independently be hydrogen, a substituted or unsubstituted C1 to C30 alkyl group or a substituted or unsubstituted C6 to C20 aryl group, $R^e$ may be a substituted or unsubstituted C6 to C20 aryl group, and $R^1$ and $R^6$ may each be one group of the set of groups listed in Group 1.

The compound may be a depositable organic semiconductor that satisfies high heat resistance and a particular (or, alternatively, predetermined) energy level, and may be effectively applied to sensors and display panels to be described later due to such properties.

For example, a glass transition temperature of the compound may be greater than or equal to about 170° C., greater than or equal to about 180° C., greater than or equal to about 190° C., greater than or equal to about 195° C., greater than or equal to about 200° C., or greater than or equal to about 210° C., within the above range, about 170° C. to about 400° C., about 180° C. to about 400° C., about 190° C. to about 400° C., about 195° C. to about 400° C., about 200° C. to about 400° C., or about 210° C. to about 400° C.

For example, the compound may be a material configured to be sublimed without decomposition or polymerization in a particular (or, alternatively, predetermined) temperature range. For example, a temperature $Ts_{10}$ at which a weight loss of 10% relative to the initial weight occurs during thermogravimetric analysis TGA of the compound at a pressure (e.g., ambient pressure) of less than or equal to about 1 Pa (e.g., 0 Pa to about 1 Pa, about 0.01 Pa to about 1 Pa, or the like) may be about 180° C. to about 450° C., about 190° C. to about 450° C., about 200° C. to about 450° C., about 210° C. to about 450° C. or about 220° C. to about 450° C. and a temperature $Ts_{50}$ at which a weight loss of 50% relative to the initial weight occurs may be about 200° C. to about 500° C., about 220° C. to about 500° C., or about 250° C. to about 500° C.

For example, a LUMO energy level of the compound may be less than or equal to about 2.80 eV, less than or equal to about 2.75 eV, less than or equal to about 2.70 eV, less than or equal to about 2.65 eV, or less than or equal to about 2.60 eV, within the above range, about 2.00 eV to about 2.80 eV, about 2.00 eV to about 2.75 eV, about 2.00 eV to about 2.70 eV, about 2.00 eV to about 2.65 eV, or about 2.00 eV to about 2.60 eV.

For example, a HOMO energy level of the compound may be less than or equal to about 5.70 eV, less than or equal to about 5.68 eV, or less than or equal to about 5.65 eV, within the above range, about 5.20 eV to about 5.70 eV, about 5.20 eV to about 5.68 eV, or about 5.20 eV to about 5.65 eV.

The aforementioned compounds may be applied, for example, to a sensor. The sensor may be a light absorption sensor configured to receive light and convert the light into an electrical signal. The sensor may be an organic sensor including an organic material as a photoelectric conversion material.

FIG. 1 is a cross-sectional view showing an example of a sensor according to some example embodiments.

Referring to FIG. 1, a sensor 100 according to some example embodiments includes a first electrode 110, a second electrode 120, a photoelectric conversion layer 130, auxiliary layers 140 and 150, and a buffer layer 160.

A substrate (not shown) may be disposed under the first electrode 110 or on the second electrode 120. The substrate may be, for example, an inorganic substrate such as a glass plate or a silicon wafer or an organic substrate made of an organic material such as polycarbonate, polymethyl methacrylate, polyethylene terephthalate, polyethylene naphthalate, polyamide, polyethersulfone, or any combination thereof. The substrate may be omitted.

The substrate may be, for example, a semiconductor substrate, or a silicon substrate. The semiconductor substrate may include a circuit unit (not shown) including for example circuitry, and the circuit unit (e.g., circuitry) may include transmission transistors (not shown) and/or charge storage (not shown) integrated in the semiconductor substrate. The circuit unit may be electrically connected to the first electrode 110 or the second electrode 120.

One of the first electrode 110 or the second electrode 120 may be an anode and the other may be a cathode. For example, the first electrode 110 may be an anode and the second electrode 120 may be a cathode. For example, the first electrode 110 may be a cathode and the second electrode 120 may be an anode.

At least one of the first electrode 110 or the second electrode 120 may be a light-transmitting electrode. The light-transmitting electrode may be a transparent electrode or a semi-transmissive electrode. The transparent electrode may have a light transmittance of greater than or equal to about 85%, greater than or equal to about 90%, or greater than or equal to about 95%, for example equal to or less than 100%, equal to or less than about 99%, or equal to or less than about 98% and the semi-transmissive electrode may have a light transmittance of greater than or equal to about 30% and less than about 85%, about 40% to about 80%, or about 40% to about 75%. The transparent electrode and the semi-transmissive electrode may include, for example, at least one of an oxide conductor, a carbon conductor, or a metal thin film. The oxide conductors may include, for example, one or more selected from indium tin oxide ITO, indium zinc oxide IZO, zinc tin oxide ZTO, aluminum tin oxide ATO, and aluminum zinc oxide AZO, the carbon conductor may include one or more selected from graphene and carbon nanostructures, and the metal thin film may be a very thin film including aluminum Al, magnesium Mg, silver Ag, gold Au, magnesium-silver Mg—Ag, magnesium-aluminum Mg—Al, an alloy thereof, or any combination thereof.

Any one of the first electrode 110 or the second electrode 120 may be a reflective electrode. The reflective electrode may include a reflective layer having a light transmittance of less than or equal to about 5% (for example, 0% to about 5%, about 0.1% to about 5%, or about 1% to about 5%) and/or a reflectance of greater than or equal to about 80% (for example, about 80% to 100%, about 80% to about 99%, or about 80% to about 95%), and the reflective layer may include an optically opaque material. The optically opaque material may include a metal, a metal nitride, or any combination thereof, for example silver Ag, copper Cu, aluminum Al, gold Au, titanium Ti, chromium Cr, nickel Ni, an alloy thereof, a nitride thereof (e.g., TiN), or any combination thereof, but is not limited thereto. The reflective electrode may comprise (e.g., may be formed of) a reflective layer or may have a stacked structure of a reflective layer/transmissive layer or a transmissive layer/reflective layer/transmissive layer, and the reflective layer may be one layer or two or more layers.

For example, each of the first electrode 110 and the second electrode 120 may be a light-transmitting electrode, and any one of the first electrode 110 or the second electrode 120 may be a light-receiving electrode disposed at the light receiving side.

For example, the first electrode 110 may be a light-transmitting electrode, the second electrode 120 may be a reflective electrode, and the first electrode 110 may be a light-receiving electrode.

For example, the first electrode 110 may be a reflective electrode, the second electrode 120 may be a light-transmitting electrode, and the second electrode 120 may be a light-receiving electrode.

The photoelectric conversion layer 130 may be configured to absorb light of at least some wavelength spectrum and convert the absorbed light into an electrical signal. For example, the photoelectric conversion layer 130 may be configured to convert at least a portion of light in the blue wavelength region (hereinafter referred to as "blue light"), light in the green wavelength region (hereinafter referred to as "green light"), light in the red wavelength region (hereinafter referred to as "red light"), or light in the infrared wavelength region (hereinafter referred to as "infrared light") into an electrical signal.

For example, the photoelectric conversion layer 130 may be configured to selectively absorb any one of blue light, green light, red light, or infrared light and convert the absorbed light into an electrical signal. Herein, the selective absorption of one of blue light, green light, red light, or infrared light may mean that a peak absorption wavelength (Amax) of an absorption spectrum is present in one of wavelength regions of greater than or equal to about 380 nm and less than about 500 nm, about 500 nm to about 600 nm, greater than about 600 nm and less than about 750 nm, or greater than or equal to about 750 nm to less than about 3000 nm, and that the absorption spectrum in the corresponding wavelength region is significantly higher than that of other wavelength regions. Herein, the "significantly higher" may mean that about 70% to about 100%, about 75% to about 100%, about 80% to about 100%, about 85% to about 100%, about 90% to about 100%, or about 95% to about 100% of the total area of the absorption spectrum may belong to the corresponding wavelength region.

The photoelectric conversion layer 130 may include at least one p-type semiconductor and at least one n-type semiconductor for photoelectric conversion of the absorbed light. The p-type semiconductor and the n-type semiconductor may form a pn junction, generate excitons by receiving light from the outside, and then separate the generated excitons into holes and electrons.

At least one of the p-type semiconductor or the n-type semiconductor may be a light absorbing material, and for example, each of the p-type semiconductor and the n-type semiconductor may be a light absorbing material. For example, at least one of the p-type semiconductor or the n-type semiconductor may be an organic material. For example, at least one of the p-type semiconductor or the n-type semiconductor may be a wavelength-selective light absorbing material configured to selectively absorb light in a particular (or, alternatively, predetermined) wavelength spectrum. For example, the p-type semiconductor and the n-type semiconductor may have the maximum absorption wavelength (Amax) in the same or different wavelength region.

For example, at least one of the p-type semiconductor or the n-type semiconductor may be a light absorbing material having a maximum absorption wavelength (Amax) in a wavelength region of greater than or equal to about 380 nm and less than about 500 nm and may be, for example, an organic light absorbing material having a maximum absorption wavelength (Amax) in a wavelength region of about 410 nm to about 480 nm.

For example, at least one of the p-type semiconductor or the n-type semiconductor may be a light absorbing material having a maximum absorption wavelength ($\lambda_{max}$) in a wavelength region of about 500 nm to about 600 nm and may be, for example, an organic light absorbing material having a maximum absorption wavelength ($\lambda_{max}$) in a wavelength region of about 520 nm to about 580 nm.

For example, at least one of the p-type semiconductor or the n-type semiconductor may be a light absorbing material having a maximum absorption wavelength ($\lambda_{max}$) in a wavelength region of greater than about 600 nm and less than about 700 nm and may be, for example, an organic light absorbing material having a maximum absorption wavelength ($\lambda_{max}$) in a wavelength region of about 620 nm to about 680 nm.

For example, the HOMO energy level of the p-type semiconductor may be about 5.0 eV to about 6.0 eV, and within the above range, about 5.1 eV to about 5.9 eV, about 5.2 eV to about 5.8 eV, or about 5.3 eV to about 5.8 eV. For example, the LUMO energy level of the p-type semiconductor may be about 2.7 eV to about 4.3 eV, and within the above range, about 2.8 eV to about 4.1 eV or about 3.0 eV to about 4.0 eV. For example, the energy bandgap of the p-type semiconductor may be about 1.7 eV to about 2.3 eV, and within the above range, about 1.8 eV to about 2.2 eV or about 1.9 eV to about 2.1 eV.

For example, a p-type semiconductor may be an organic material having a core structure including an electron donating moiety EDM, a π-conjugated linking moiety LM, and an electron accepting moiety EAM and represented by Chemical Formula A.

EDM-LM-EAM [Chemical Formula A]

In Chemical Formula A,

EDM may be an electron donating moiety,

EAM may be an electron accepting moiety, and

LM may be a pi conjugated linking moiety to link the electron donating moiety and the electron accepting moiety.

For example, the p-type semiconductor may be represented by Chemical Formula 2.

[Chemical Formula 2]

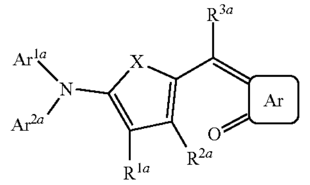

In Chemical Formula 2,

X may be 0, S, Se, Te, SO, $SO_2$, $CR^bR^c$, or $SiR^dR^e$,

Ar may be a substituted or unsubstituted C6 to C30 arylene group, a substituted or unsubstituted C3 to C30 heterocyclic group, or a fused ring of two or more selected therefrom, $Ar^{1a}$ and $Ar^{2a}$ may each independently be a substituted or unsubstituted C6 to C30 aryl(ene) group or a substituted or unsubstituted C3 to C30 heteroaryl(ene) group, $R^{1a}$ to $R^{3a}$ and $R^b$ to $R^e$ may each independently be hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, and $Ar^{1a}$, $Ar^{2a}$, $R^{1a}$, and $R^{2a}$ may each independently be present, or two adjacent ones may be linked to each other to form a ring.

For example, $Ar^{1a}$ and $Ar^{2a}$ may each independently be a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, or a substituted or unsubstituted pyridopyridazinyl group.

For example, $Ar^{1a}$ and $Ar^{2a}$ may be linked to each other to form a ring.

For example, $Ar^{2a}$ and $R^{1a}$ may be linked to each other to form a ring.

Specifically, the p-type semiconductor may be represented by Chemical Formula 2A or 2B.

[Chemical Formula 2A]

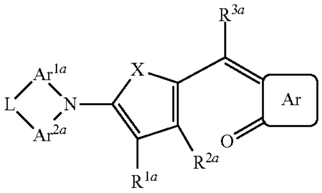

[Chemical Formula 2B]

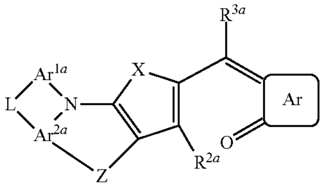

In Chemical Formulas 2A and 2B3,

X may be O, S, Se, Te, SO, $SO_2$, $CR^bR^c$, or $SiR^dR^e$,

Ar may be a substituted or unsubstituted C6 to C30 arylene group, a substituted or unsubstituted C3 to C30 heterocyclic group, or a fused ring thereof, $Ar^{1a}$ and $Ar^{2a}$ may each independently be a substituted or unsubstituted C6 to C30 arylene group or a substituted or unsubstituted C3 to C30 heteroarylene group, L and Z may each independently be a single bond, O, S, Se, Te, SO, $SO_2$, $CR^fR^g$, $SiR^hR^i$, $GeR^jR^k$, $NR^l$, a substituted or unsubstituted C1 to C30 alkylene group, a substituted or unsubstituted C3 to C30 cycloalkylene group, a substituted or unsubstituted C6 to C30 arylene group, or any combination thereof, and $R^{1a}$, $R^{2a}$, $R^{3a}$, and $R^b$ to $R^l$ may each independently be hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof.

For example, the p-type semiconductor may be one compound selected from compounds listed in Groups 2A, 2B, or 2C, but is not limited thereto.

[Group 2A]

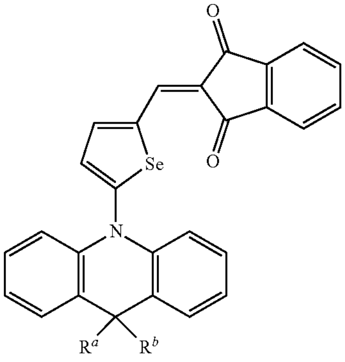

-continued

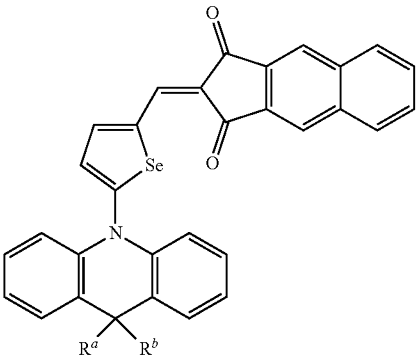

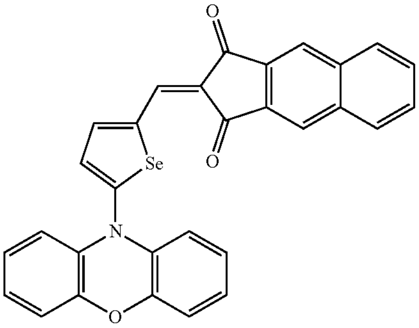

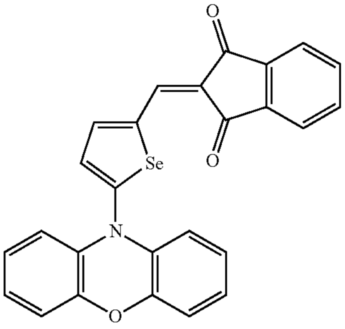

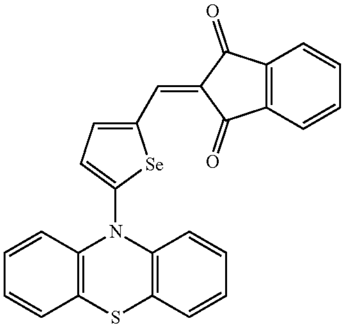

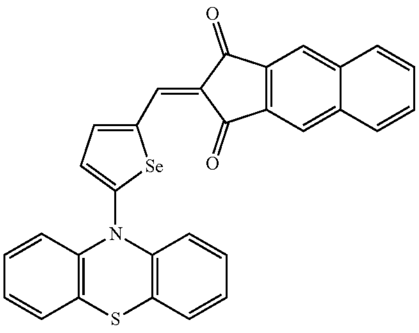

-continued
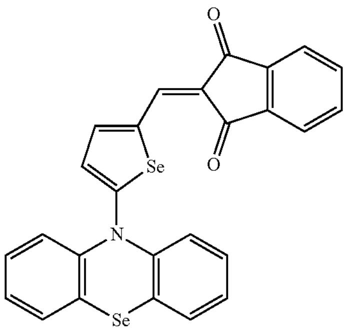
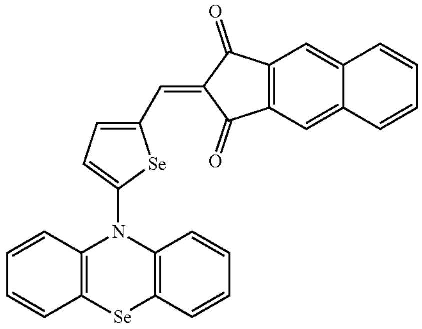
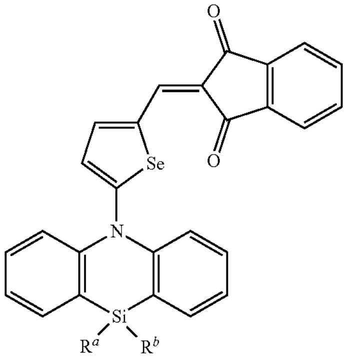
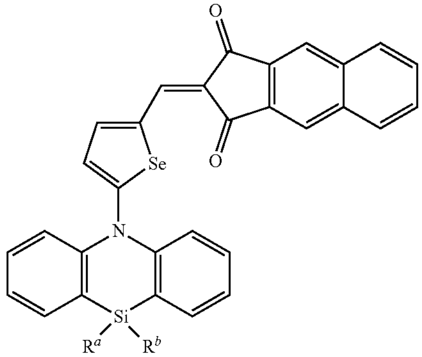
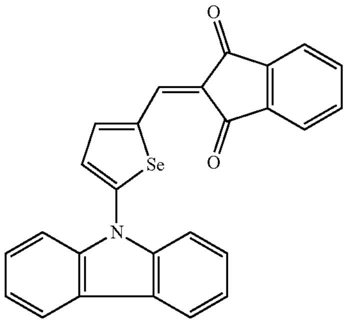
-continued
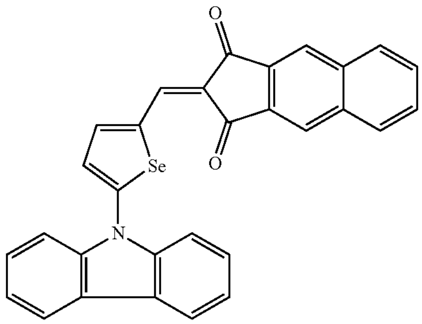
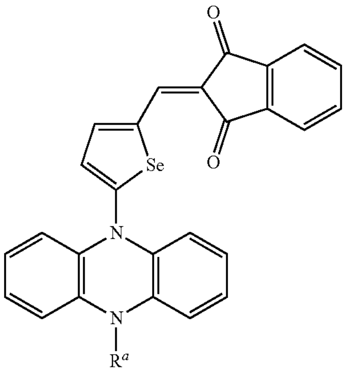
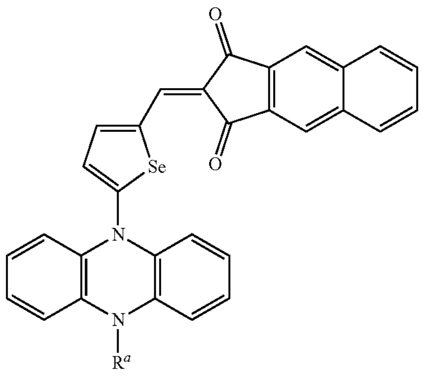
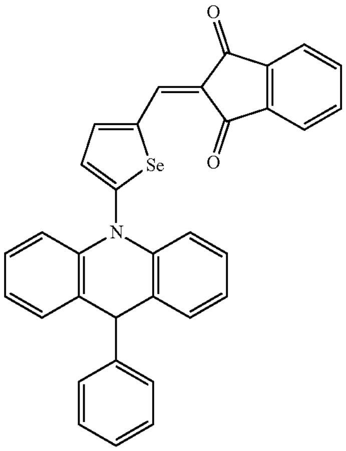

-continued
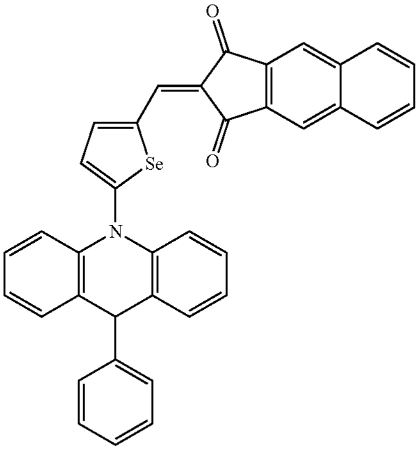
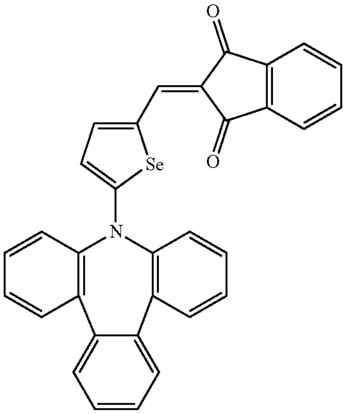
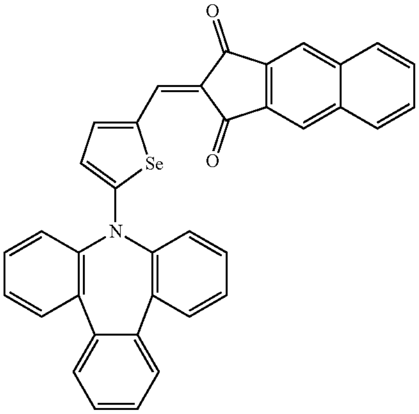
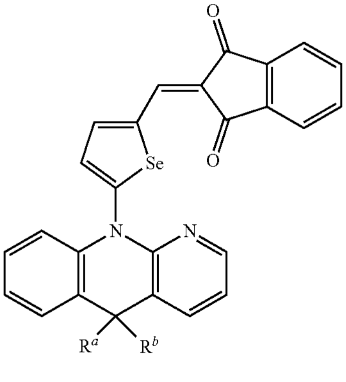
-continued
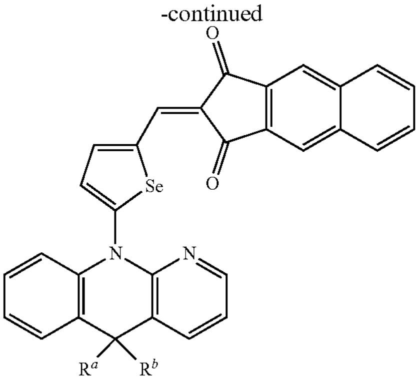
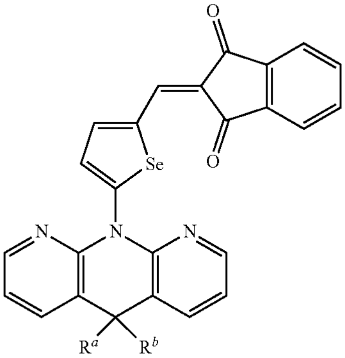
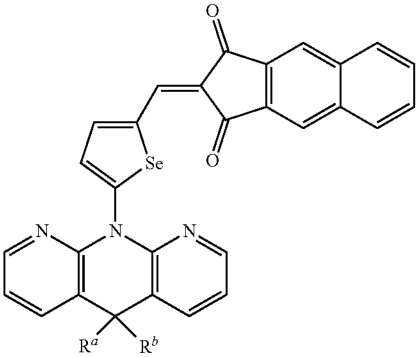
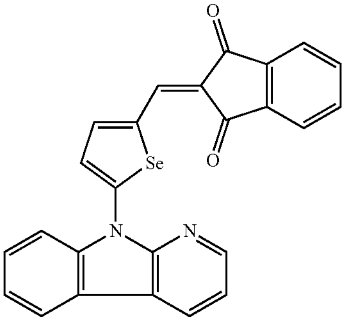
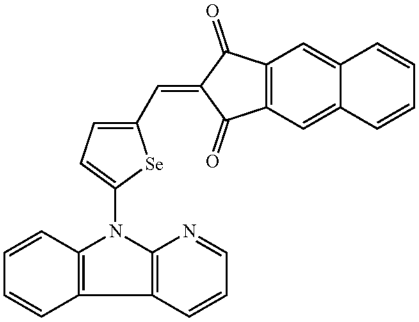

-continued
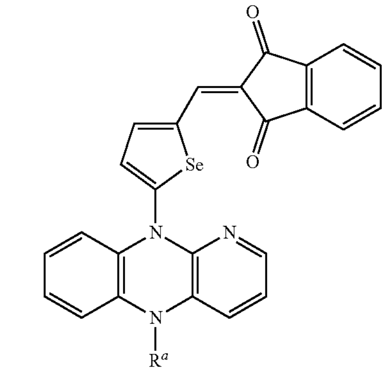
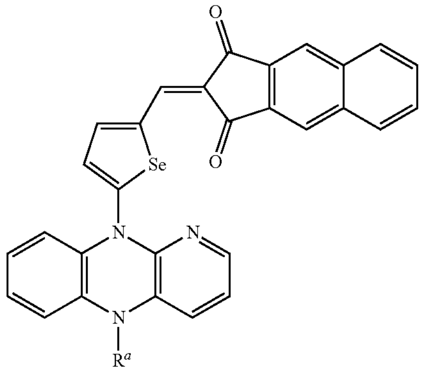
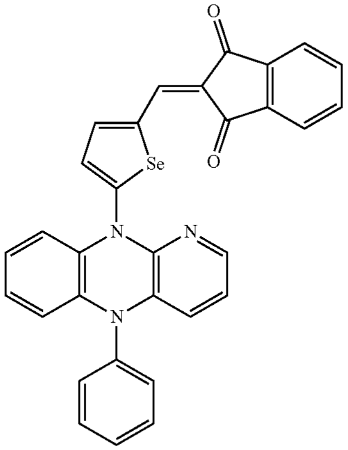
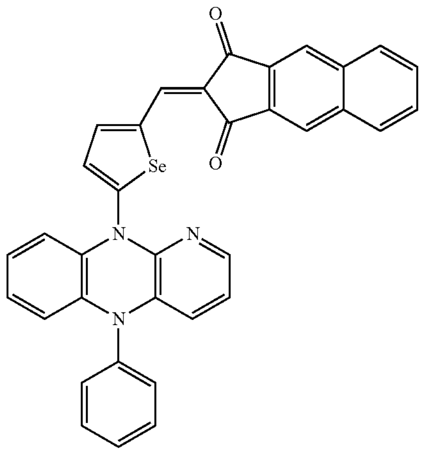
-continued
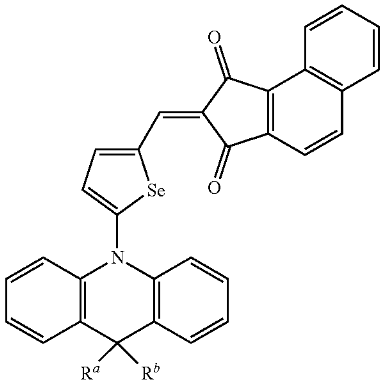
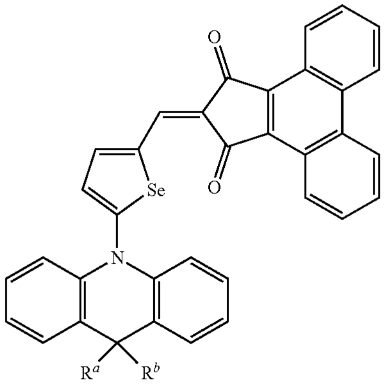
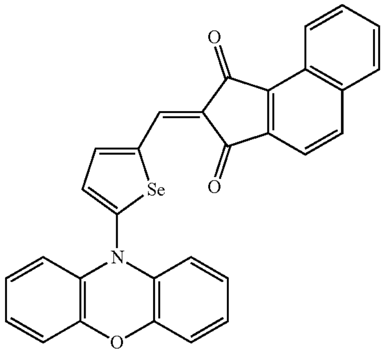
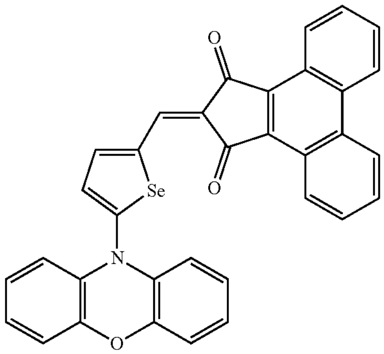

-continued
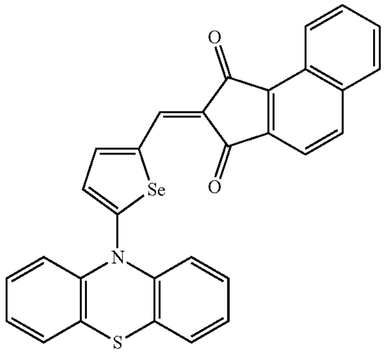
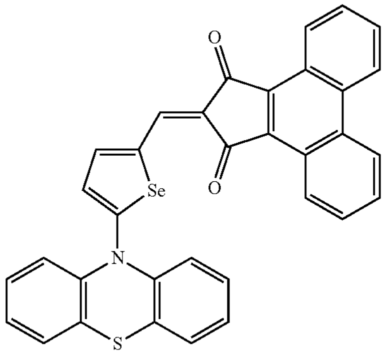
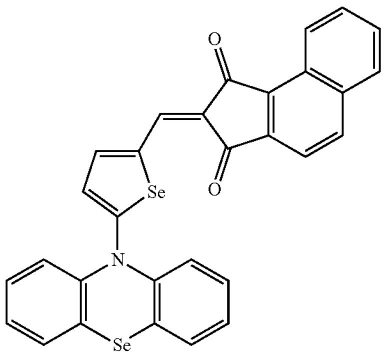
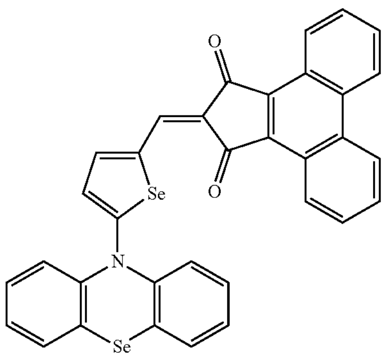
-continued
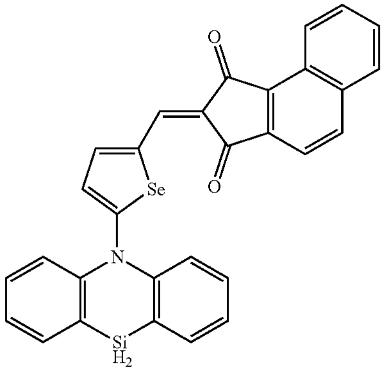
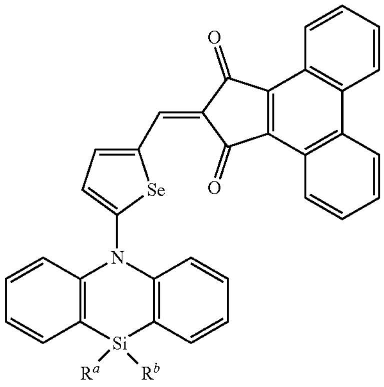
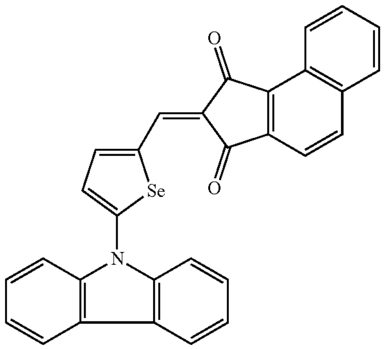
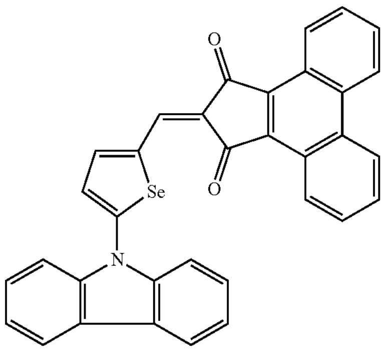

-continued
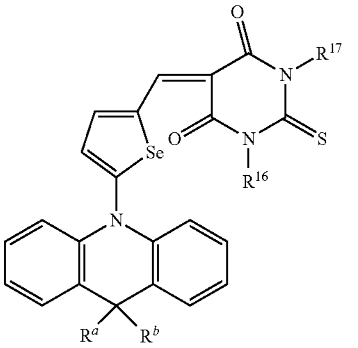
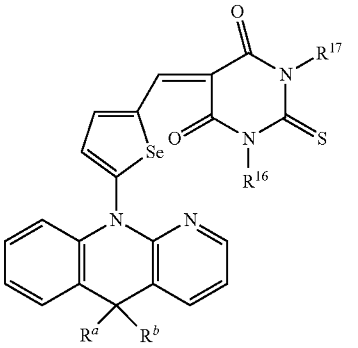
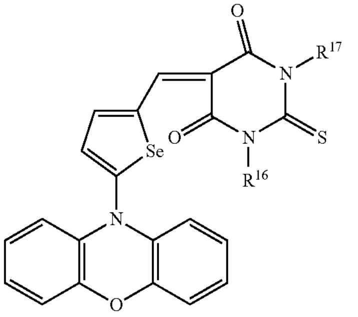
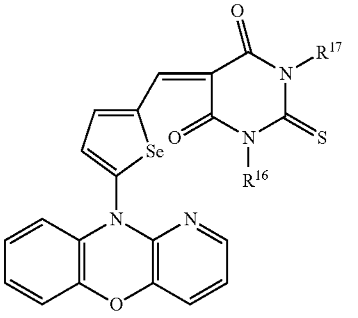
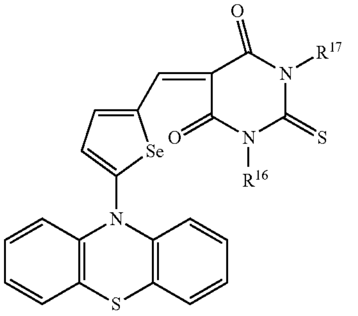
-continued
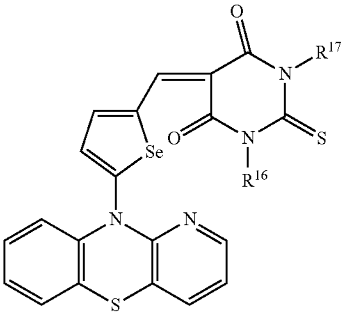
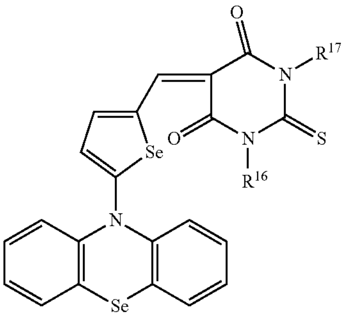
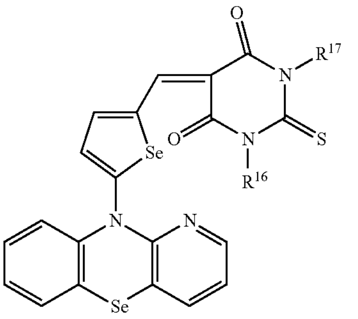
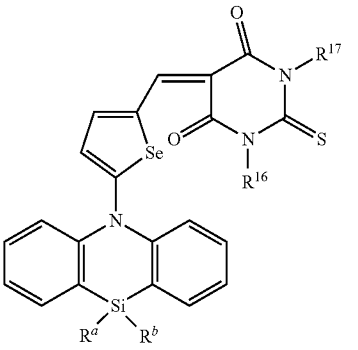
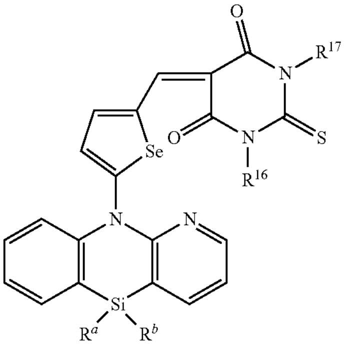

-continued
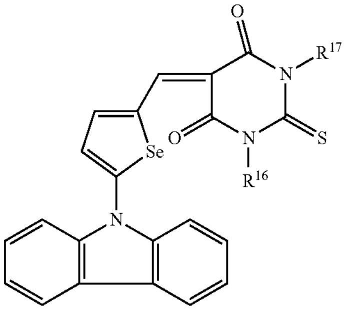
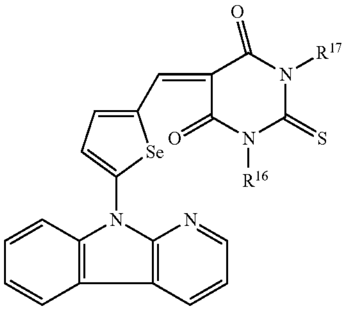
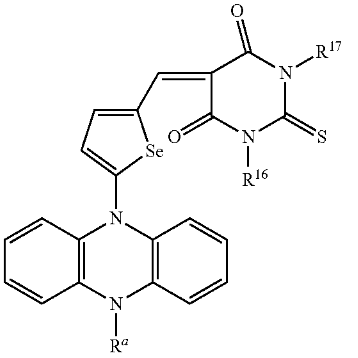
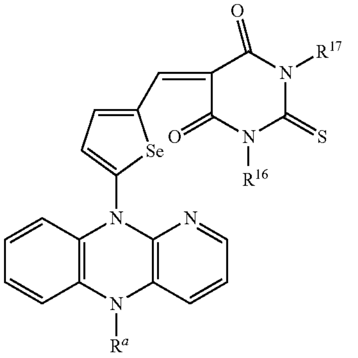
-continued
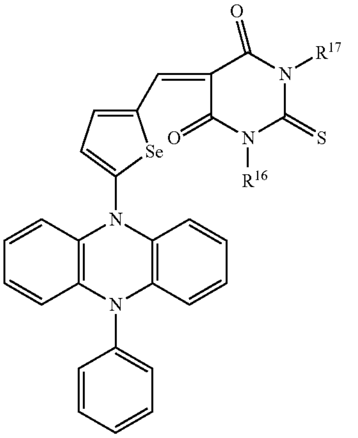
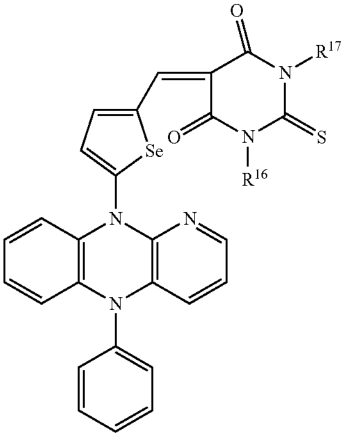
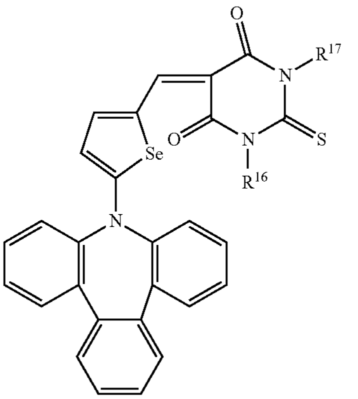
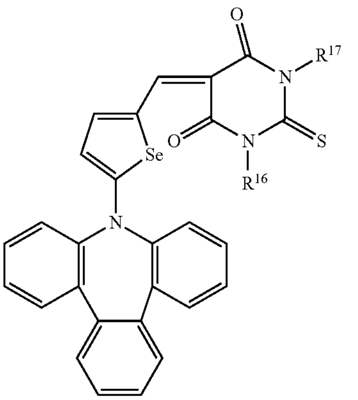

-continued
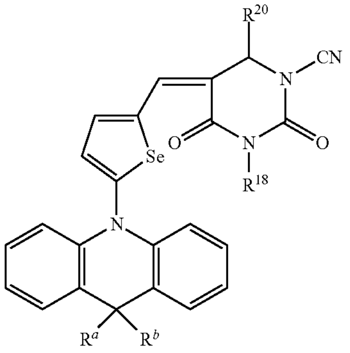
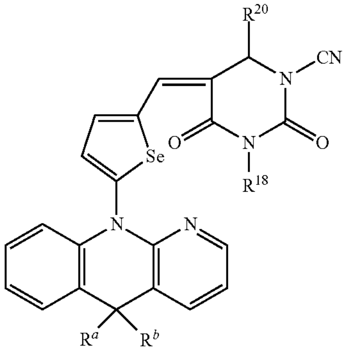
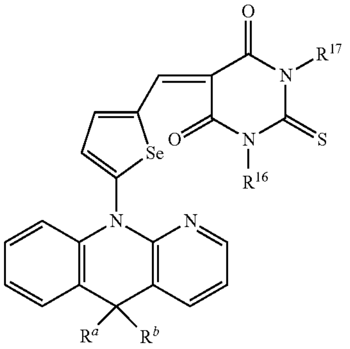
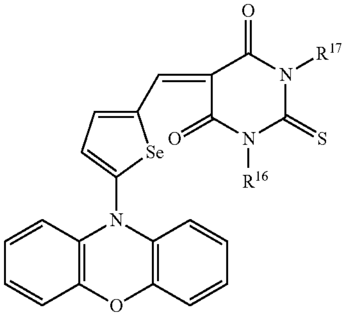
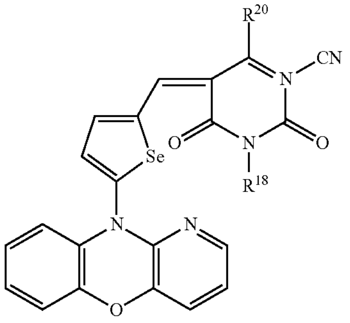
-continued
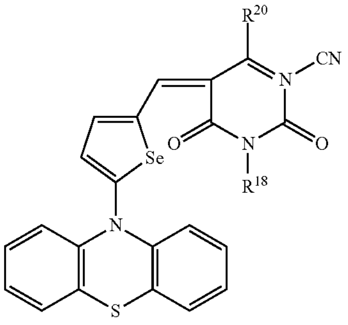
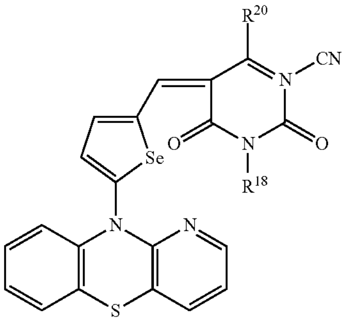
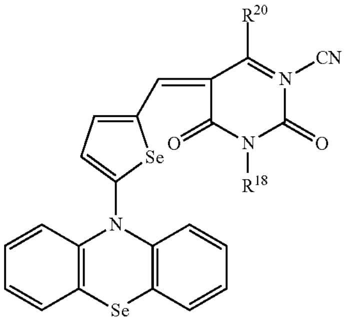
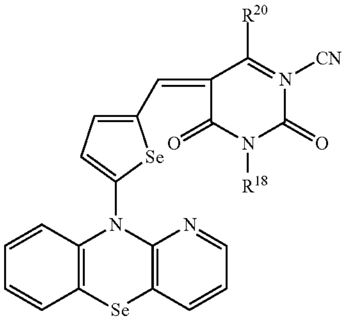
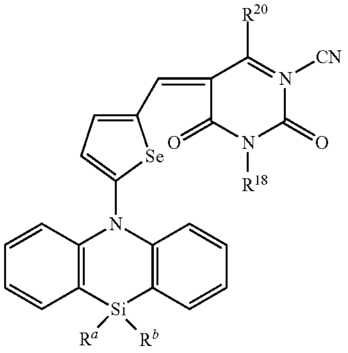

-continued
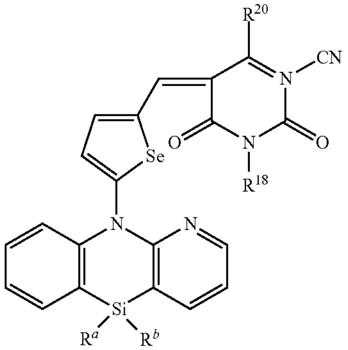
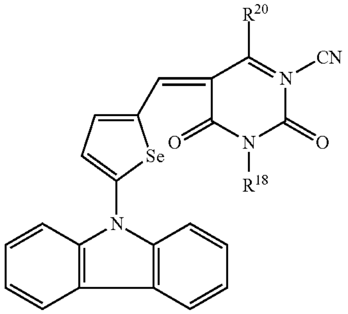
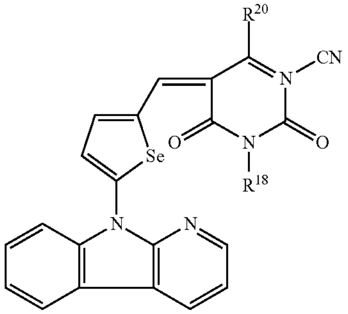
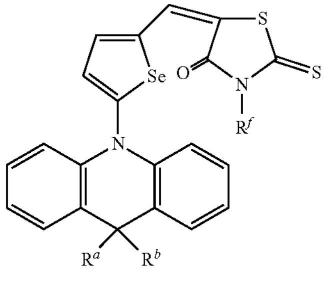
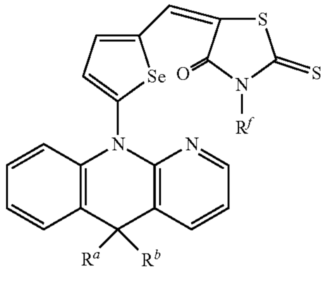
-continued
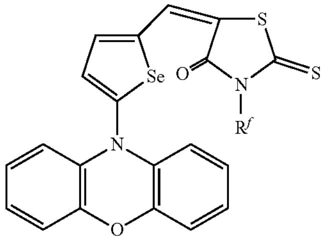
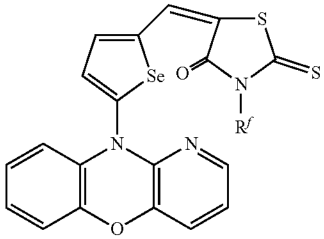
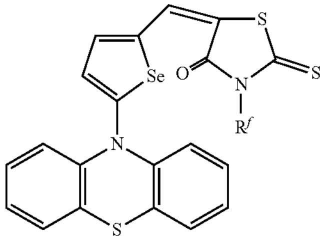
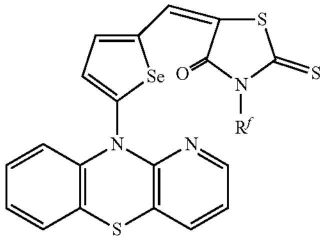
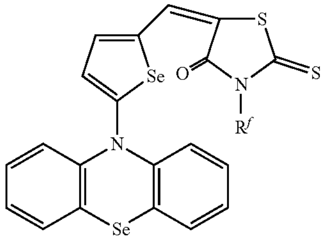
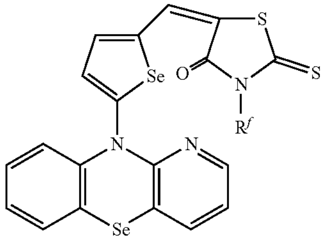
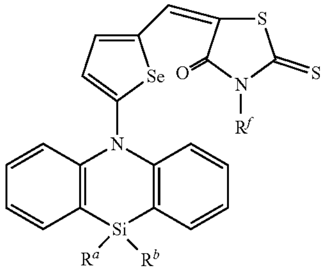

-continued

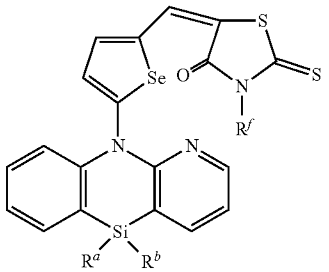

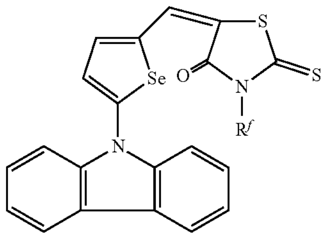

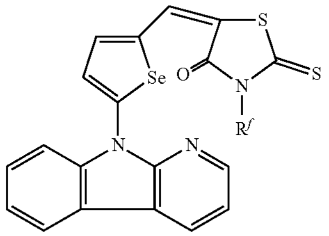

In Group 2A, at least one hydrogen present in each aromatic ring or heteroaromatic ring may each independently replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and any combination thereof, and $R^a$, $R^b$, $R^f$, $R^{16}$, $R^{17}$, $R^{18}$, and $R^{21}$ may each independently be hydrogen or a substituted or unsubstituted C1 to C6 alkyl group.

[Group 2B]

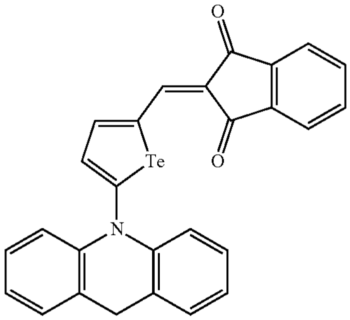

-continued

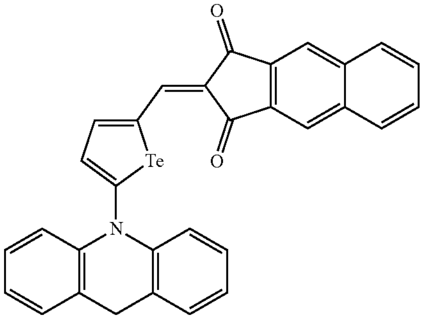

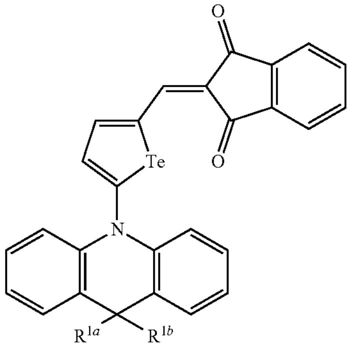

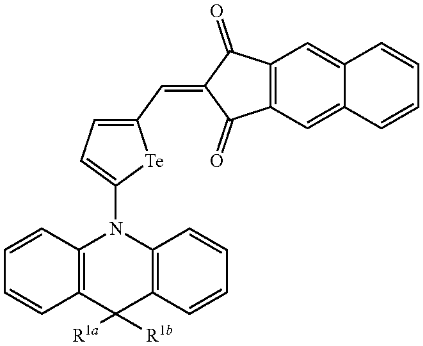

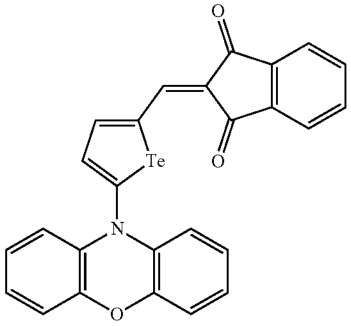

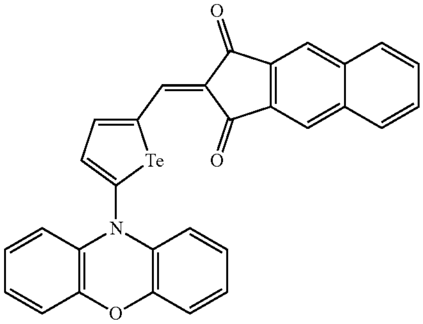

-continued
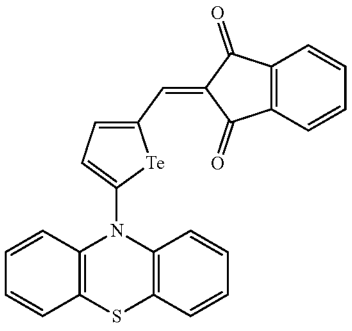
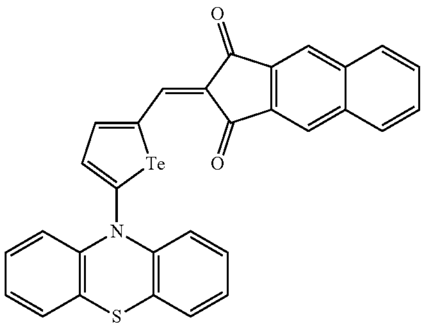
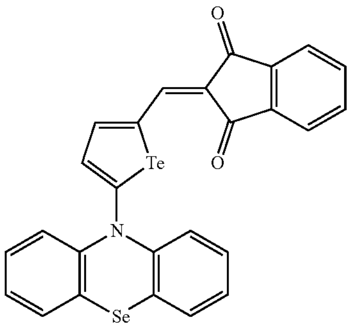
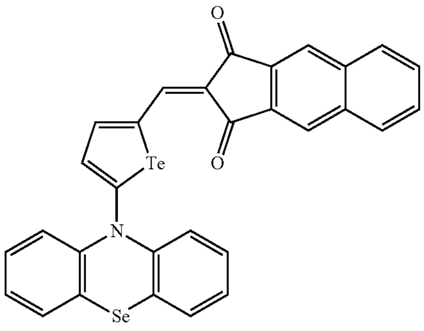
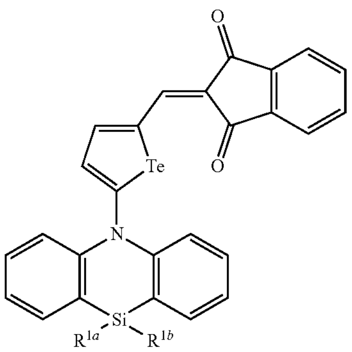
-continued
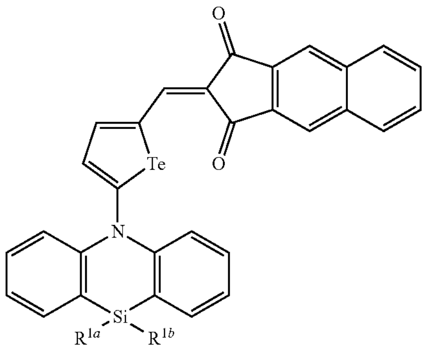
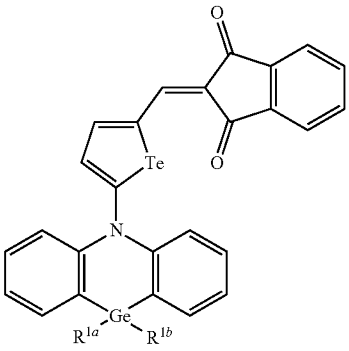
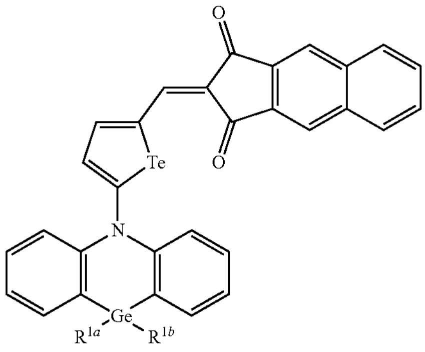
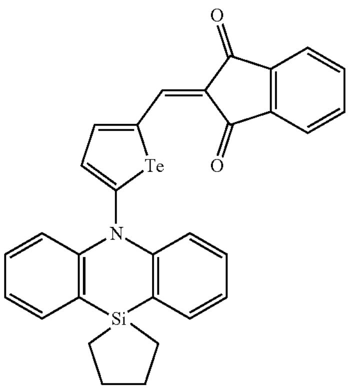

-continued
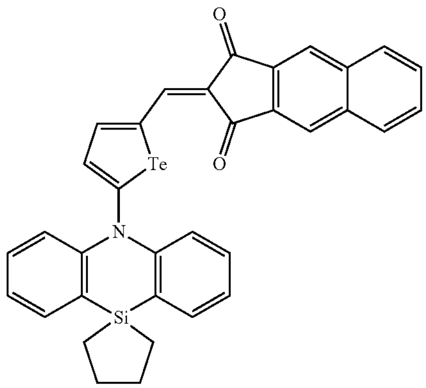
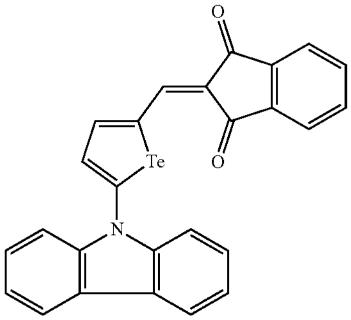
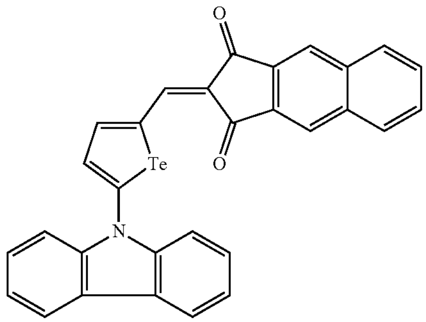
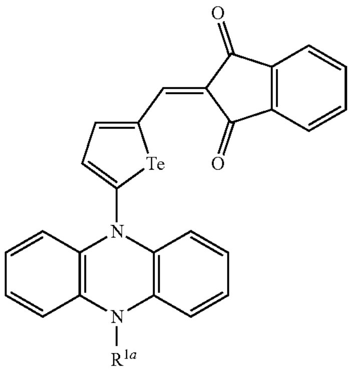
-continued
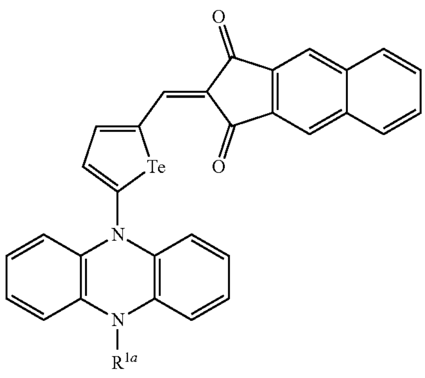
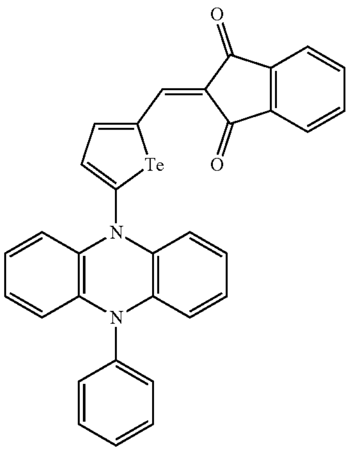
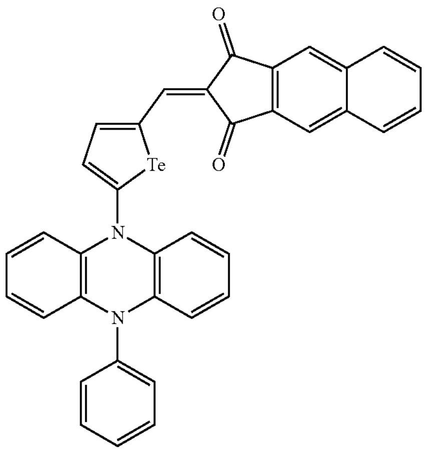
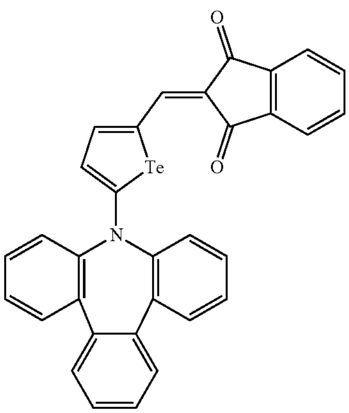

-continued
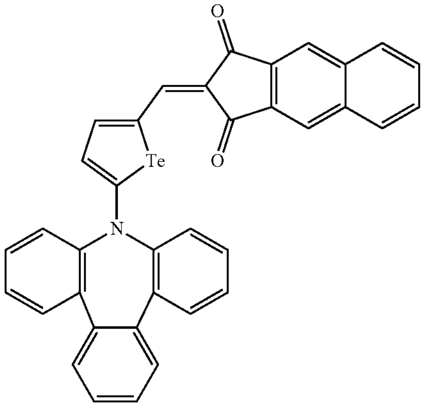
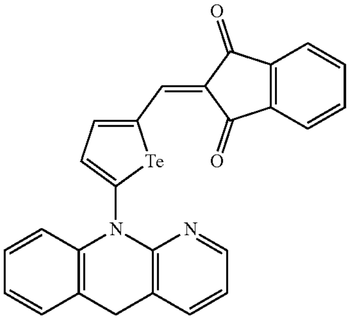
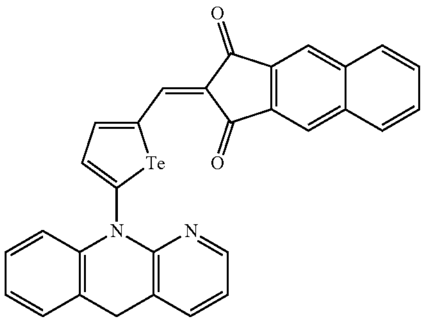
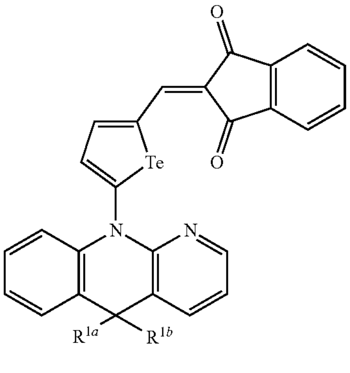
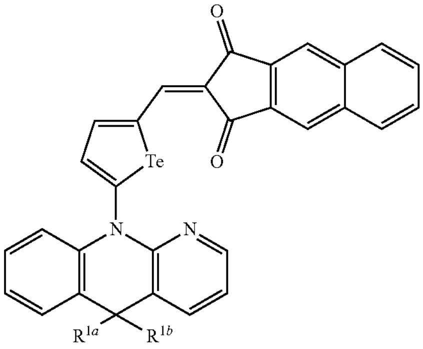
-continued
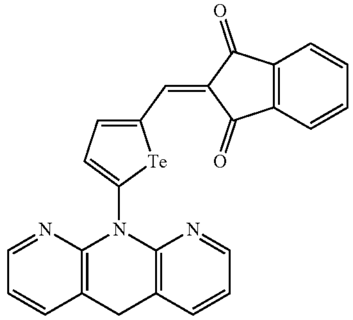
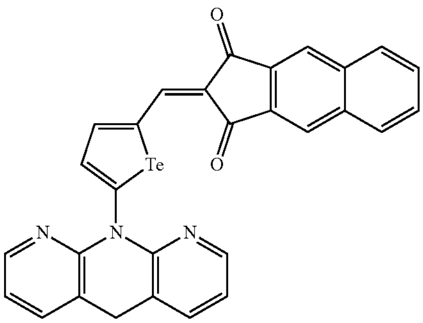
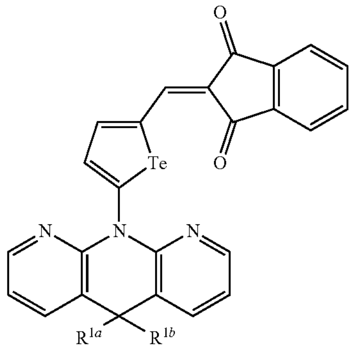
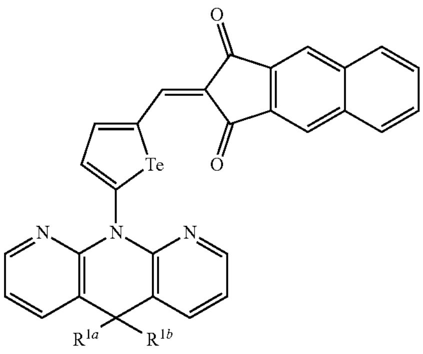

-continued
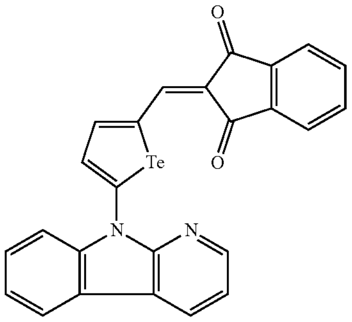
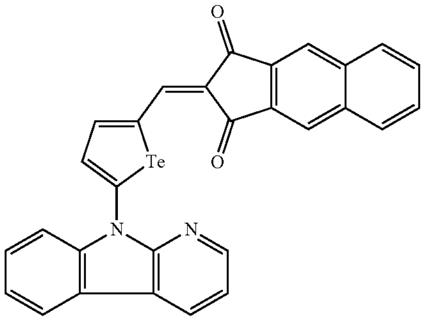
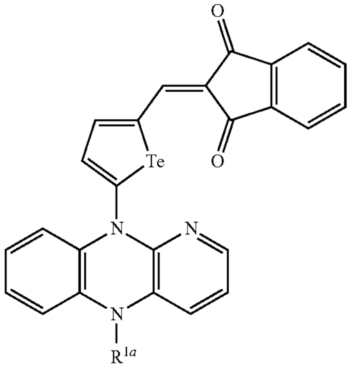
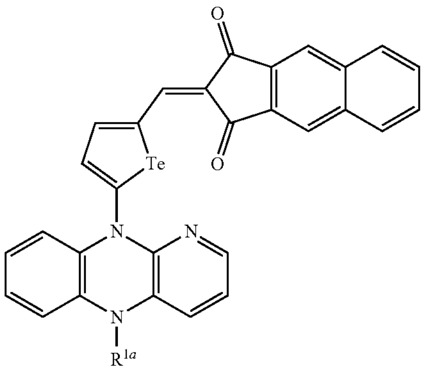
-continued
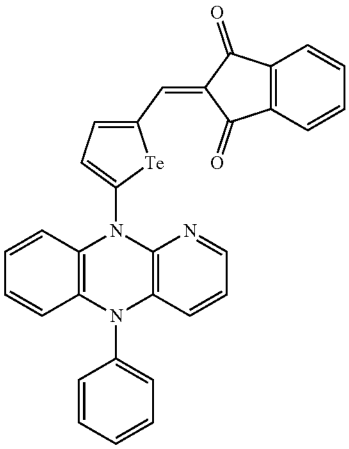
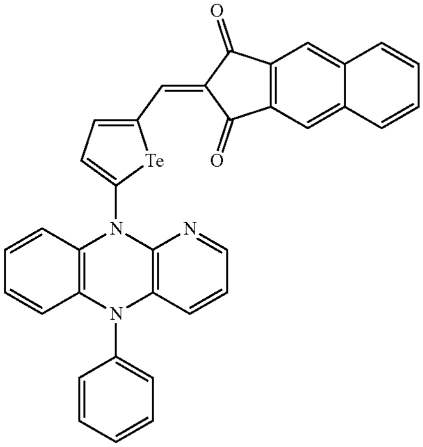
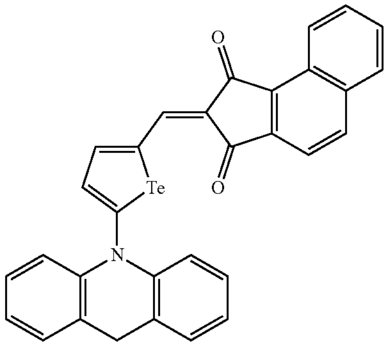
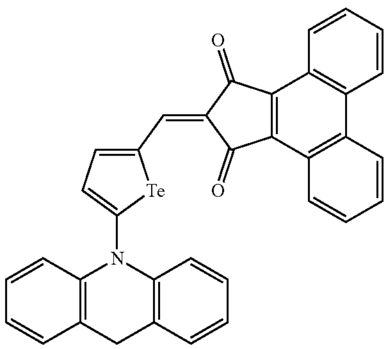

-continued
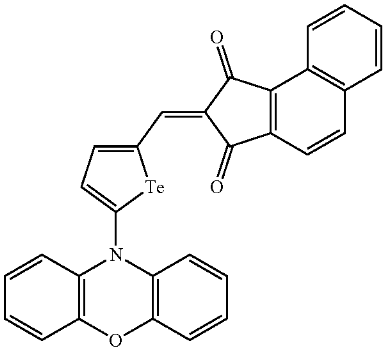
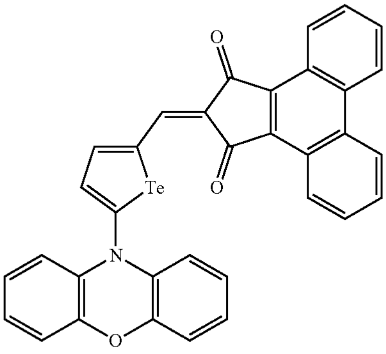
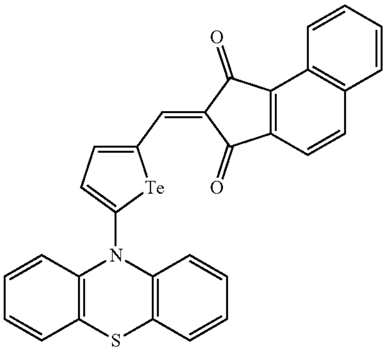
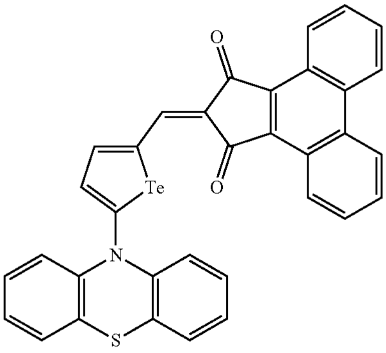
-continued
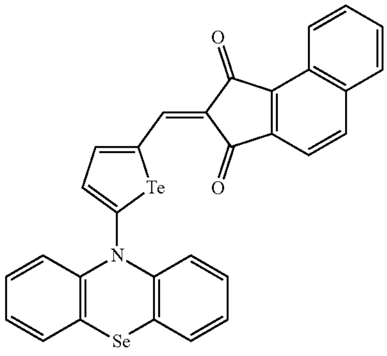
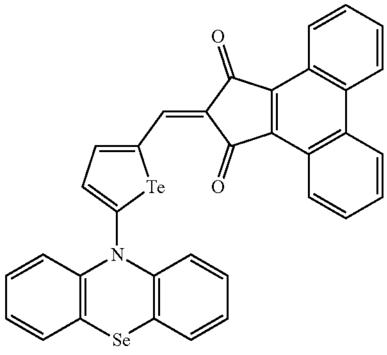
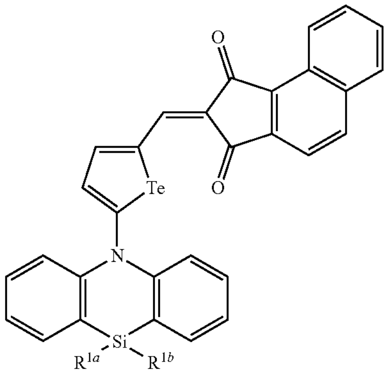
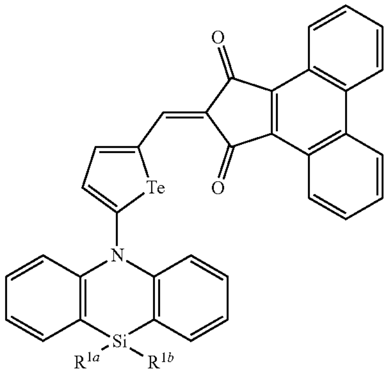

-continued
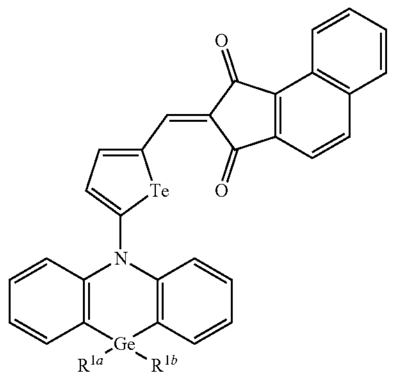
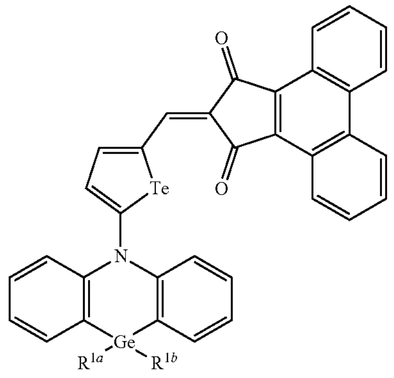
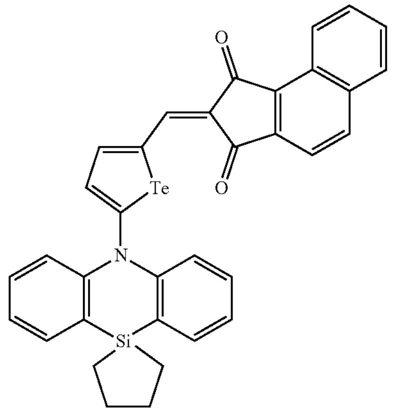
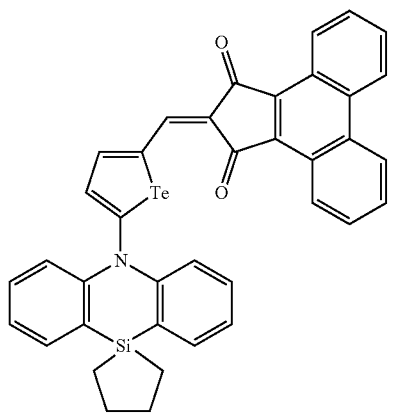
-continued
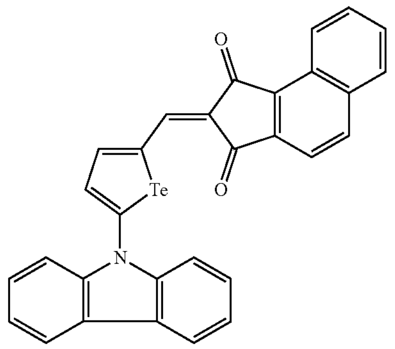
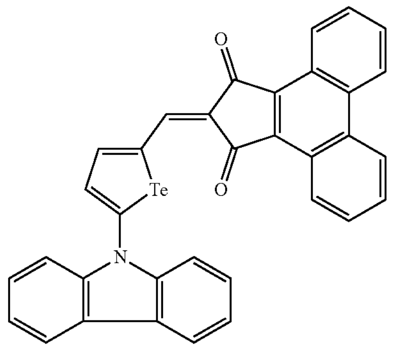
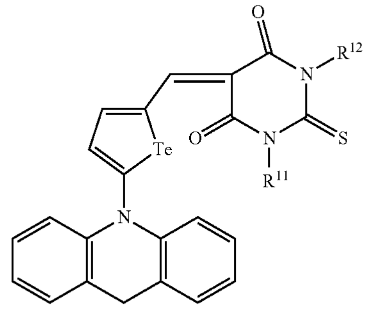
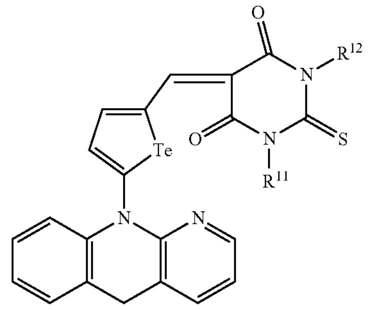
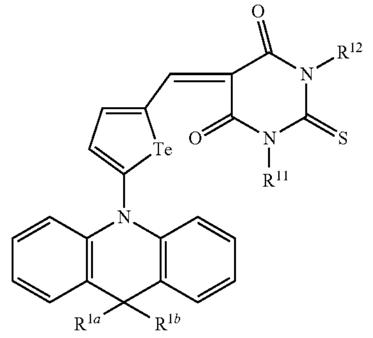

-continued
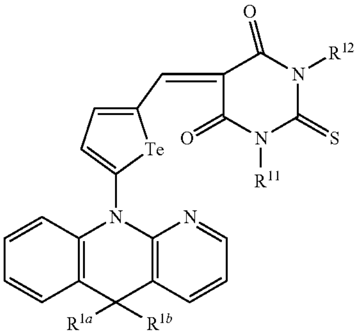
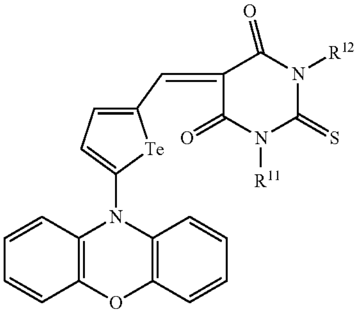
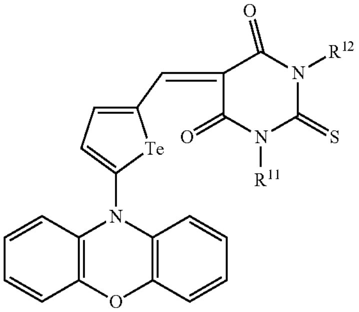
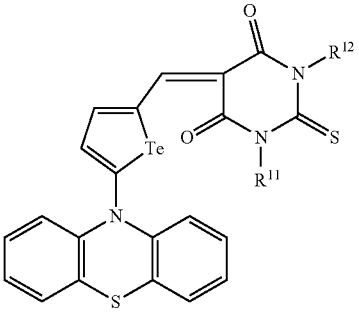
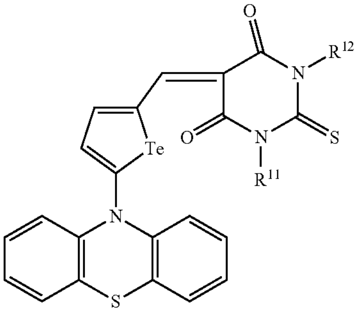
-continued
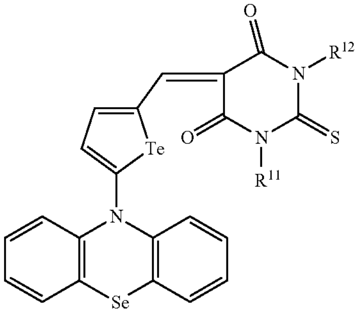
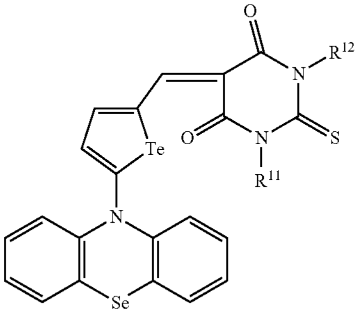
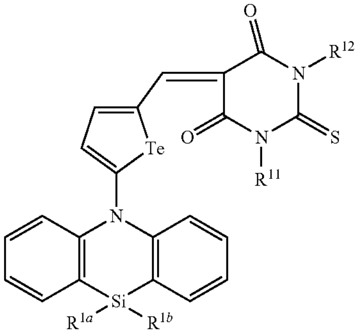
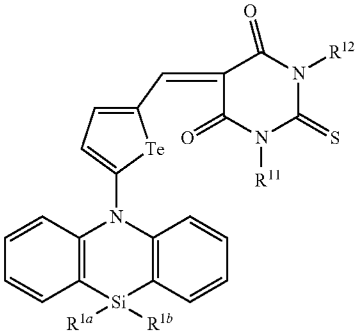
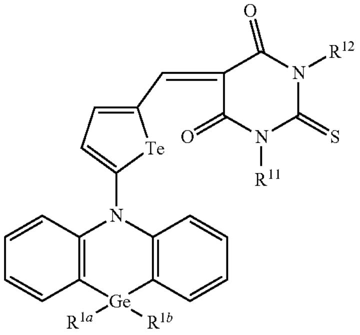

-continued
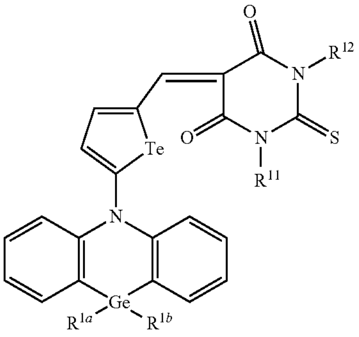
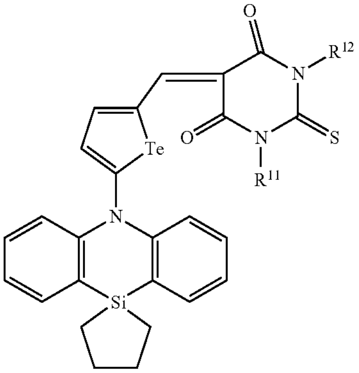
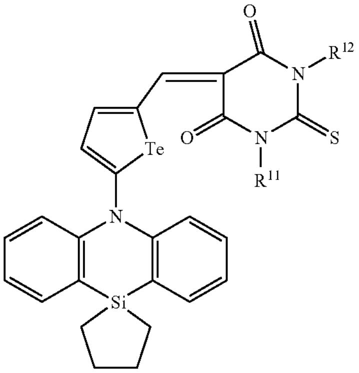
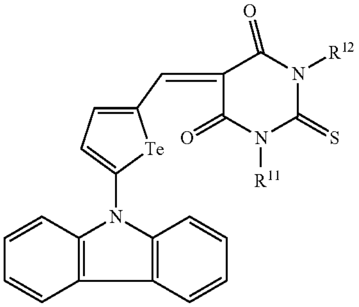
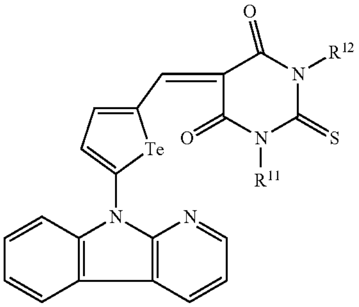
-continued
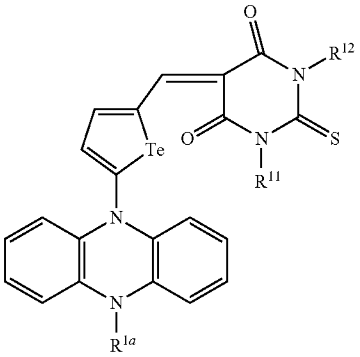
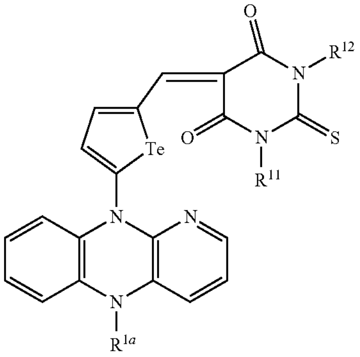
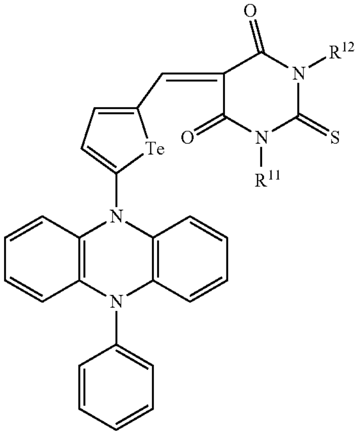
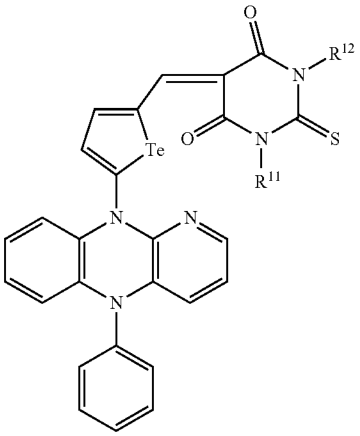

-continued
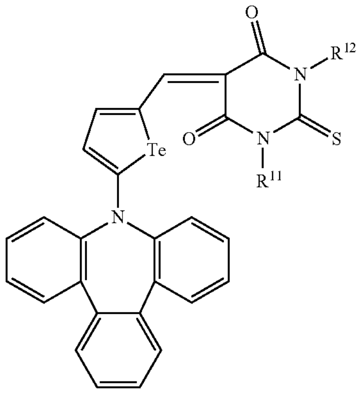
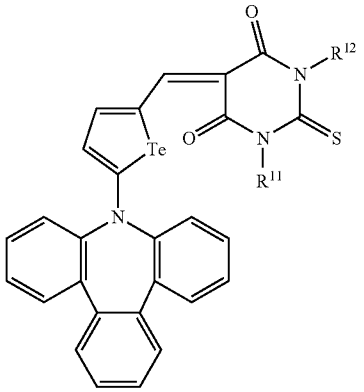
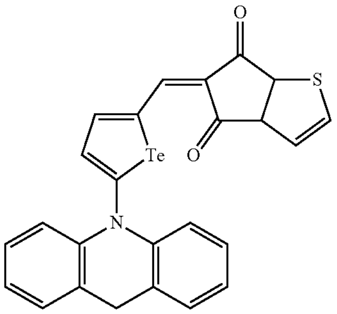
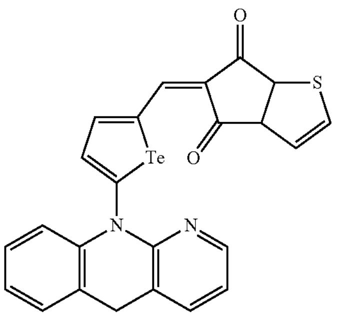
-continued
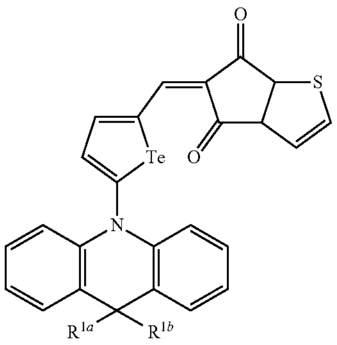
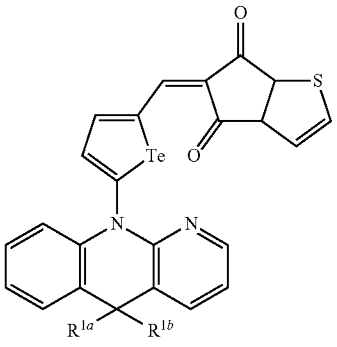
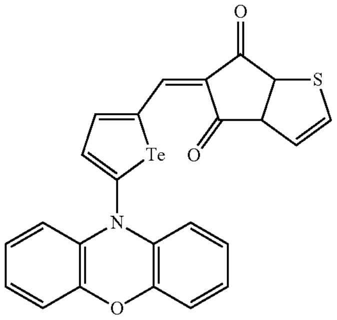
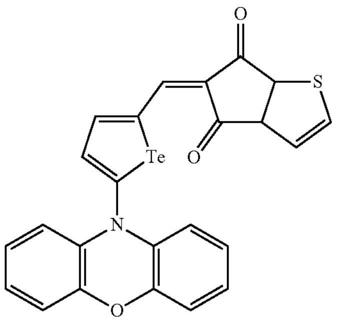
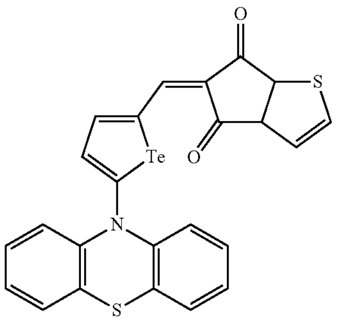

-continued
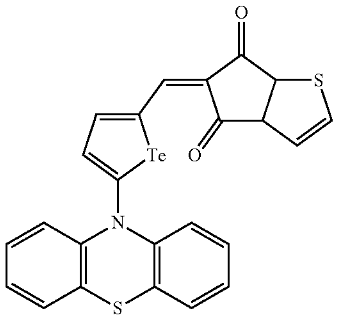
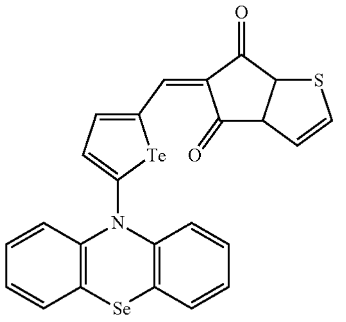
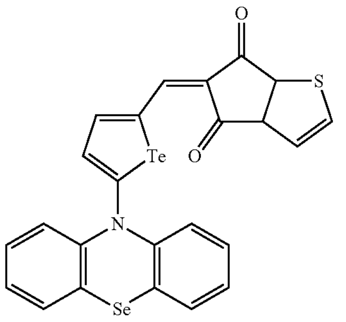
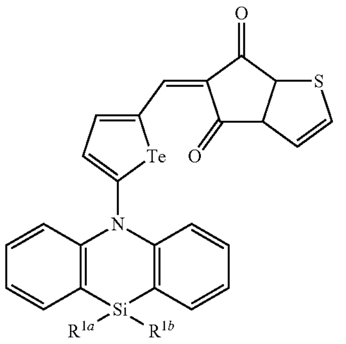
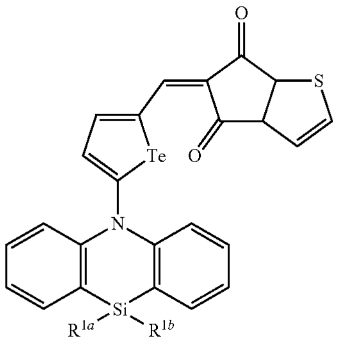
-continued
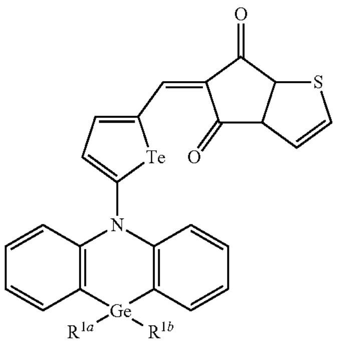
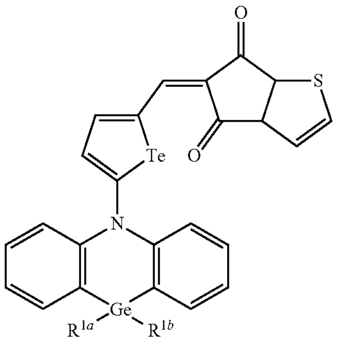
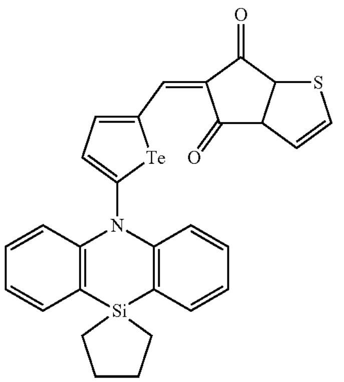
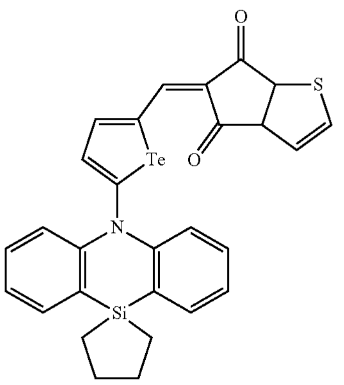

-continued
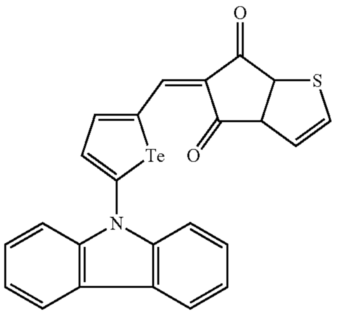
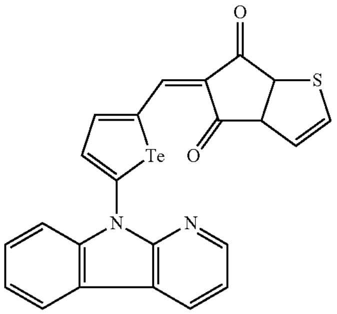
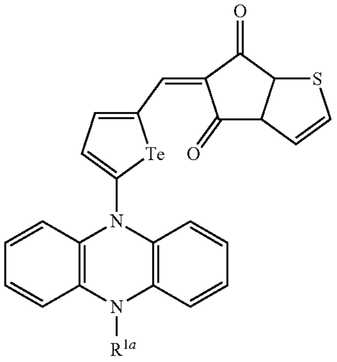
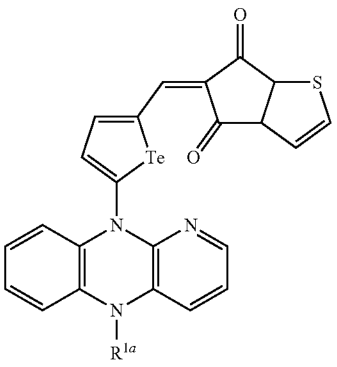
-continued
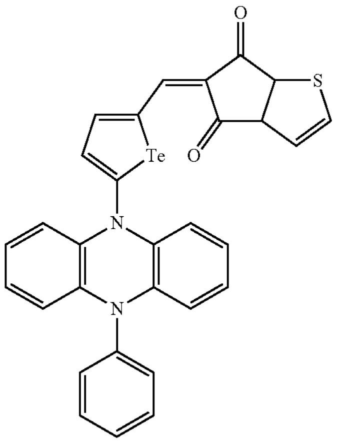
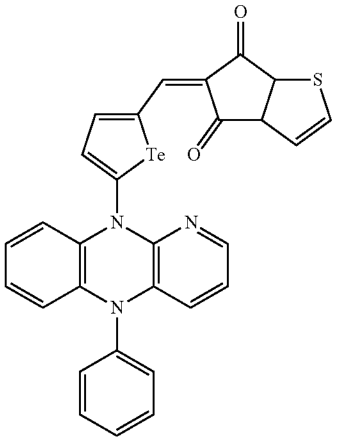
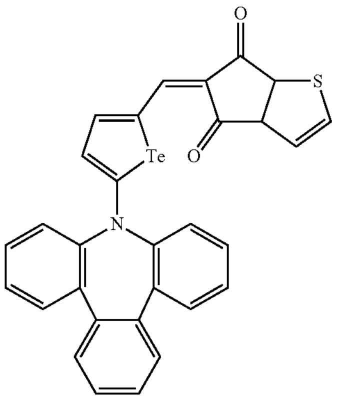
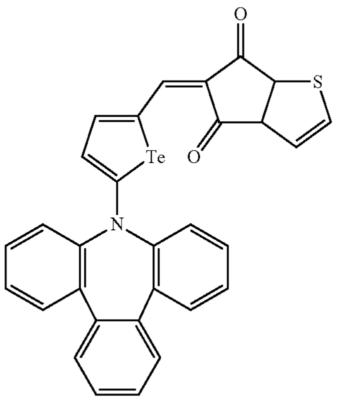

-continued
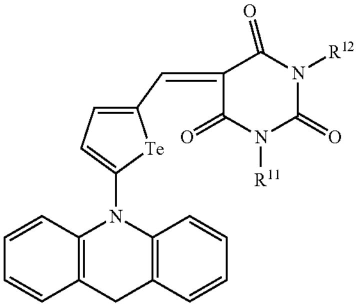
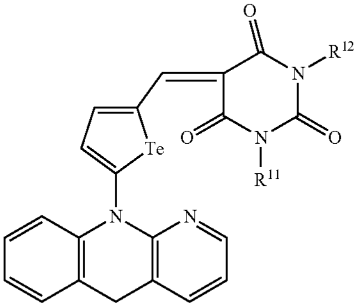
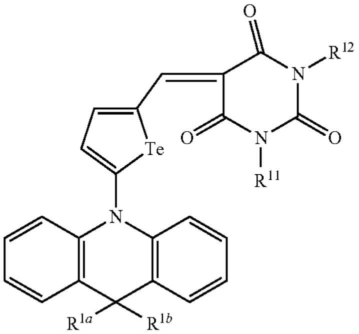
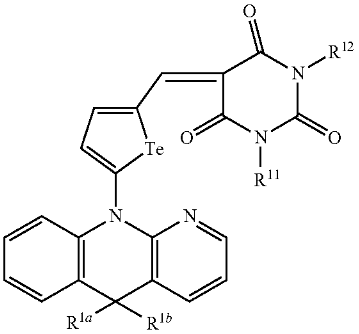
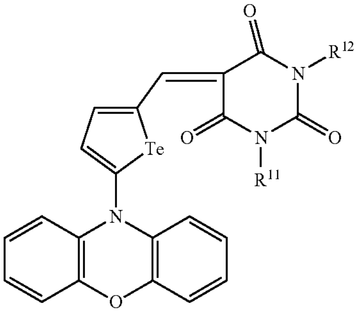
-continued
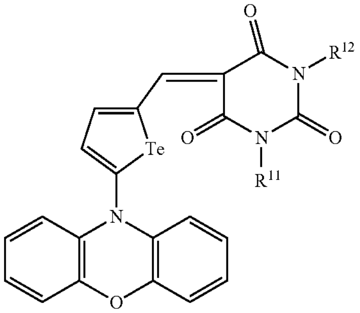
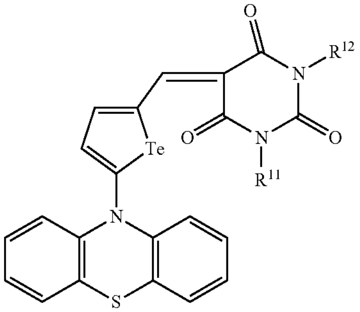
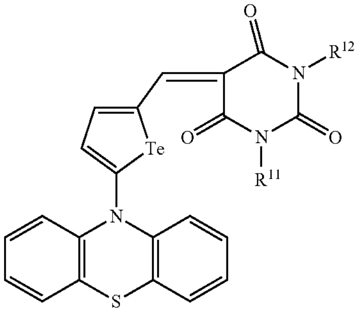
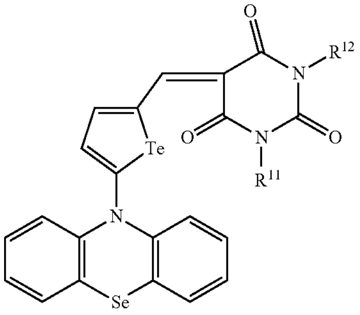
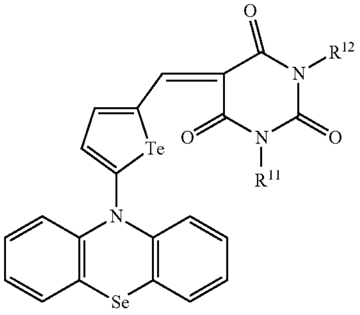

-continued
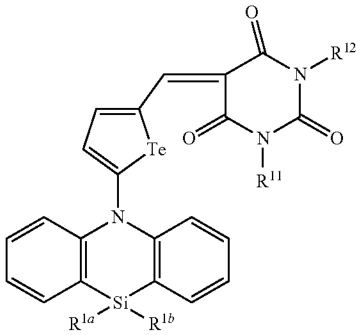
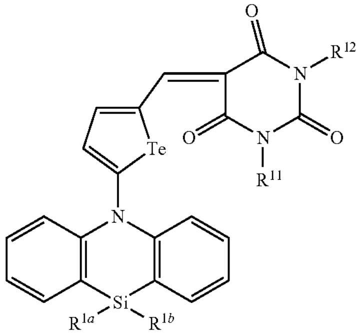
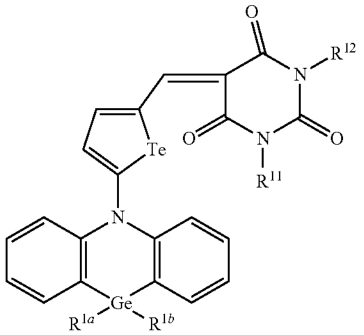
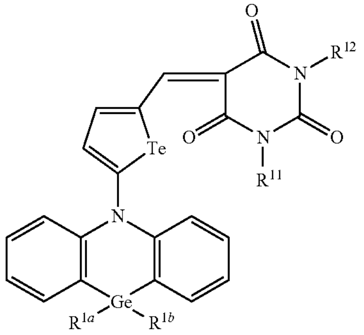
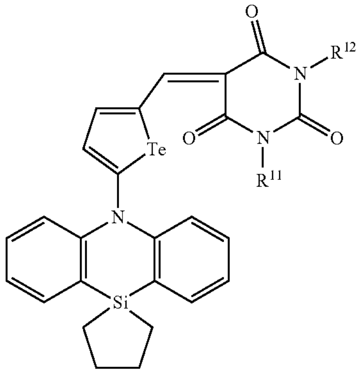
-continued
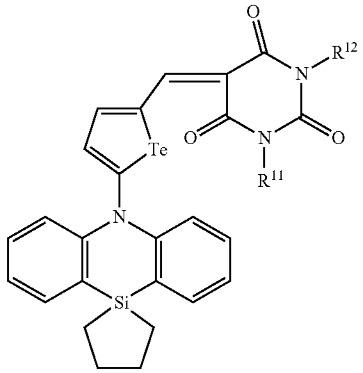
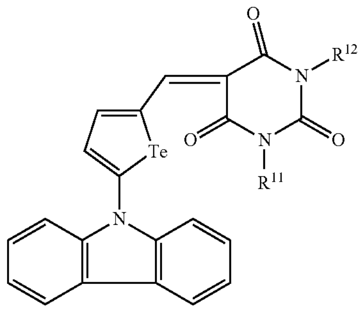
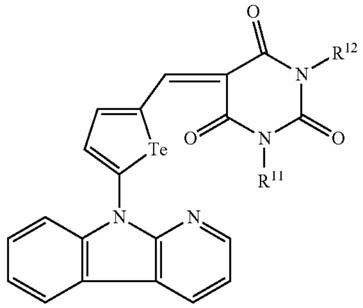
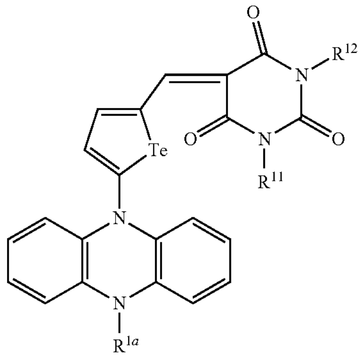
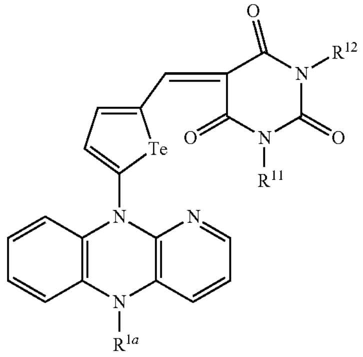

-continued
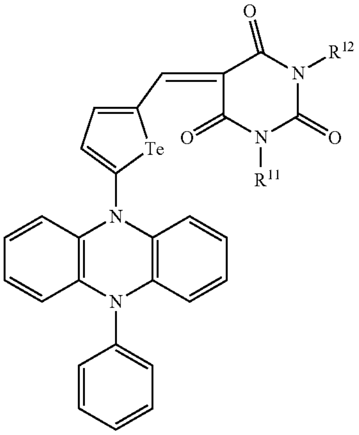
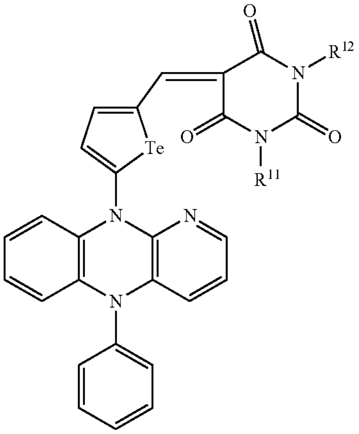
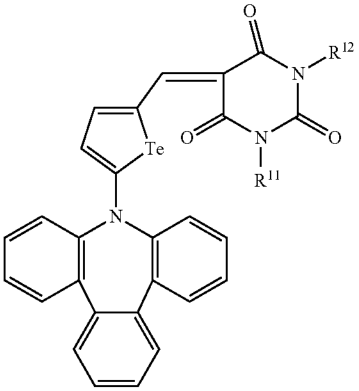
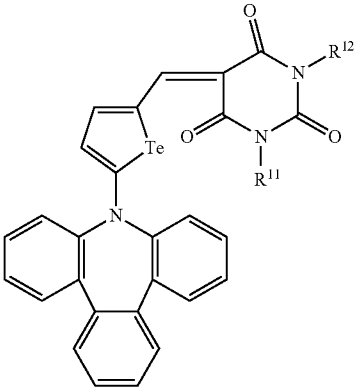
-continued
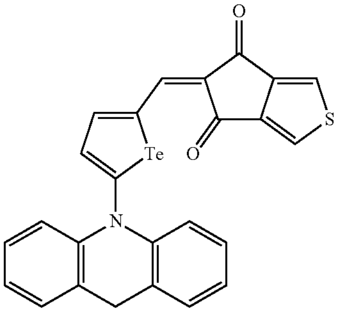
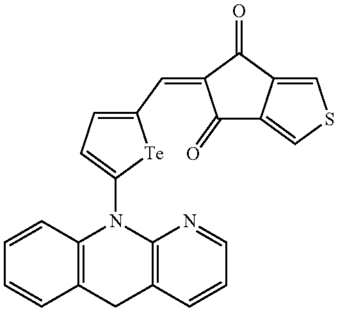
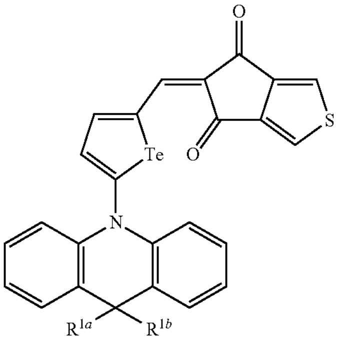
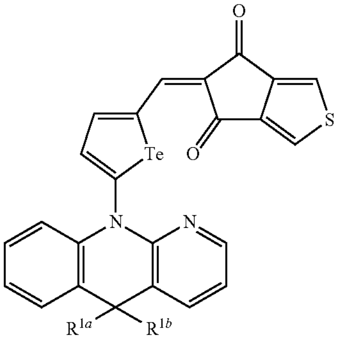
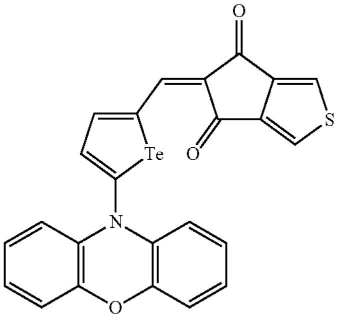

-continued
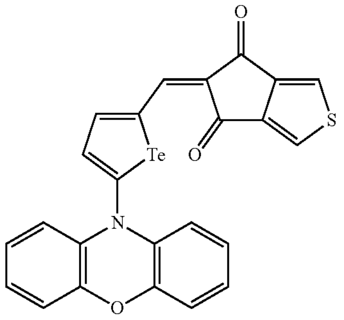
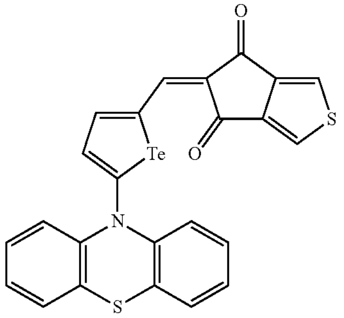
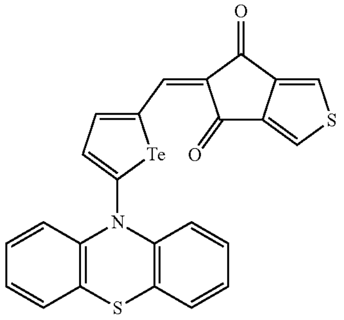
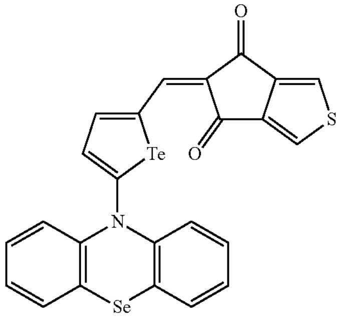
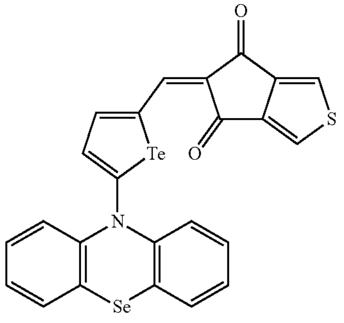
-continued
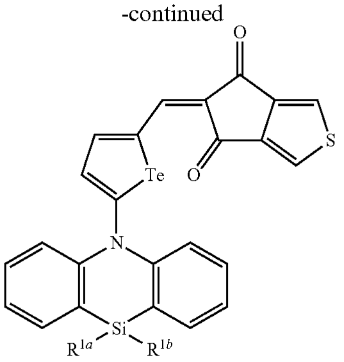
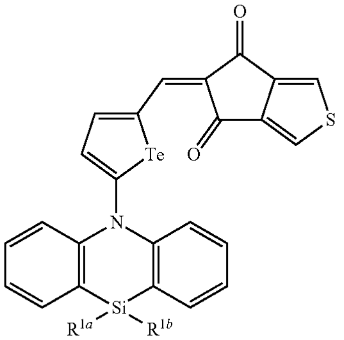
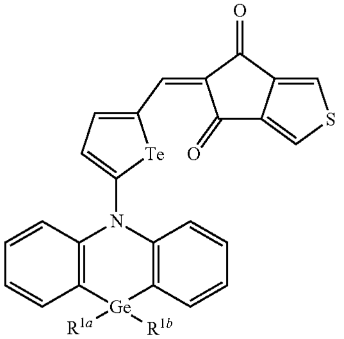
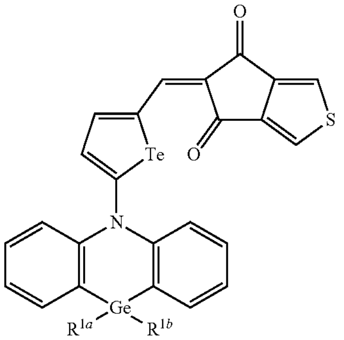
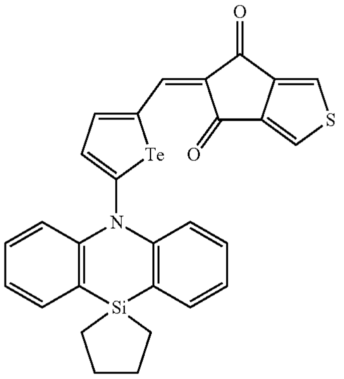

-continued
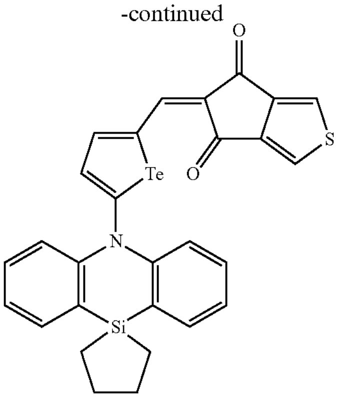
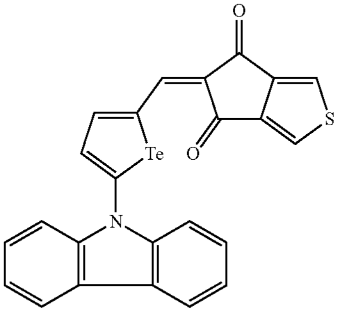
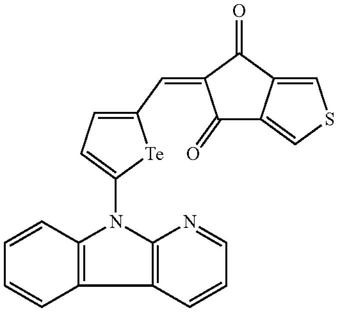
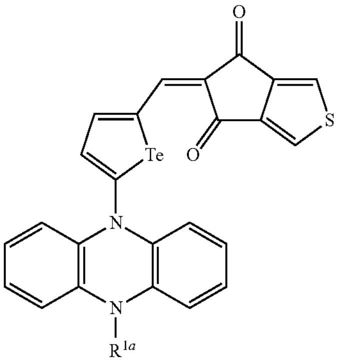
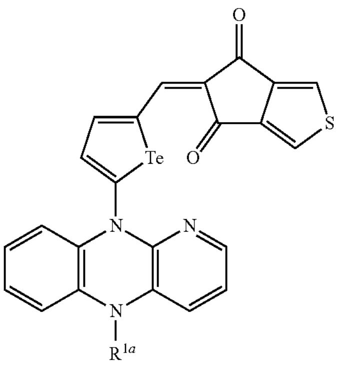
-continued
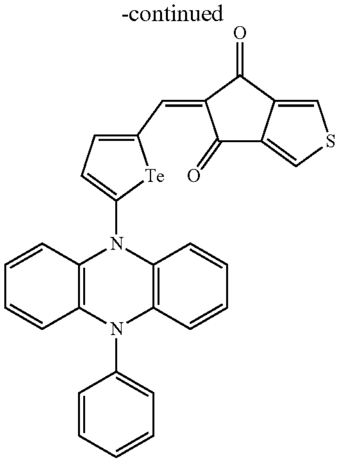
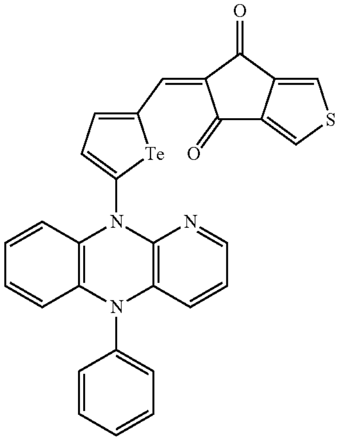
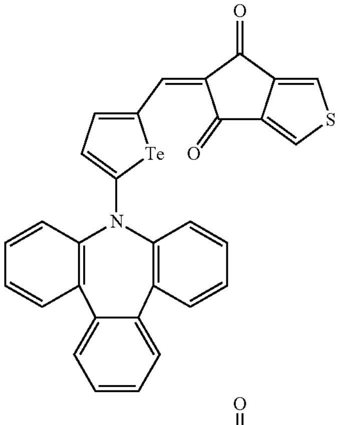
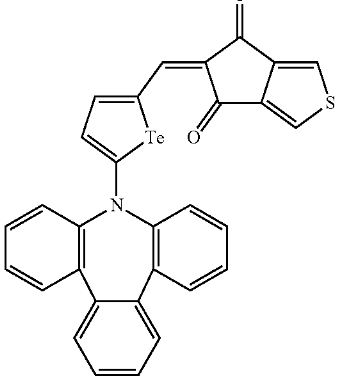
In Group 2B, at least one hydrogen present in each aromatic ring or heteroaromatic ring may each independently replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and any combination thereof, and $R^{1a}$, $R^{1b}$, $R^{11}$, and $R^{12}$ may each independently be hydrogen or a substituted or unsubstituted C1 to C6 alkyl group.

[Group 2C]

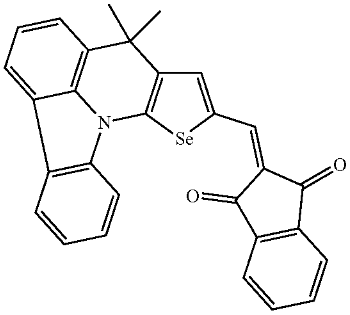

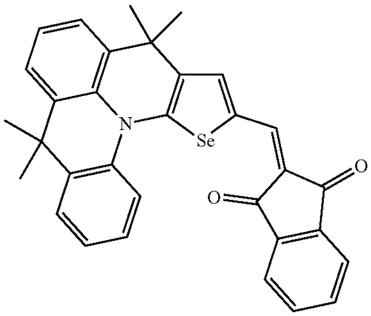

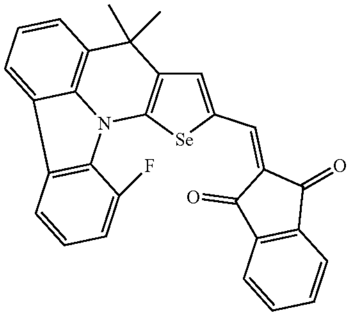

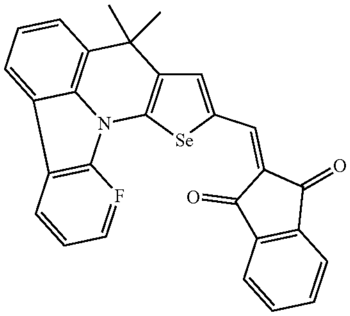

-continued

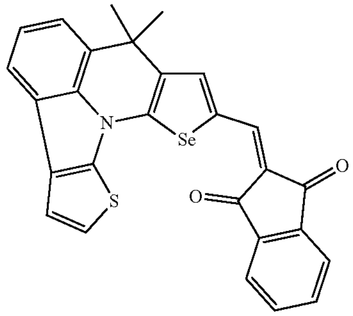

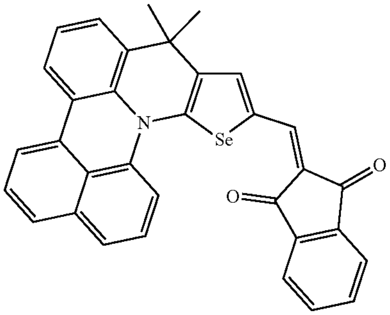

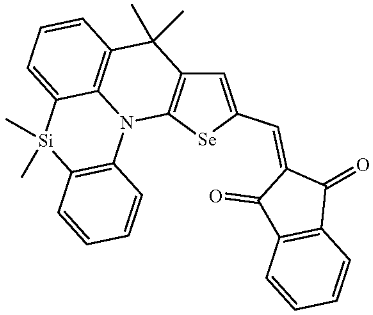

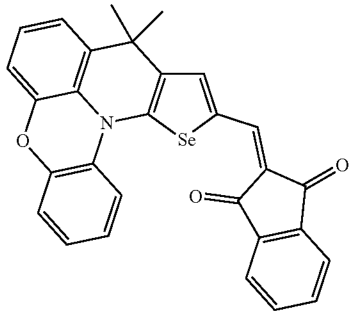

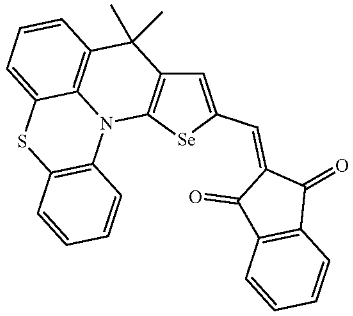

-continued
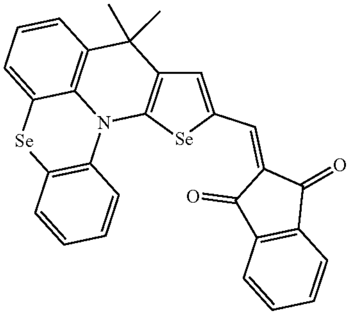
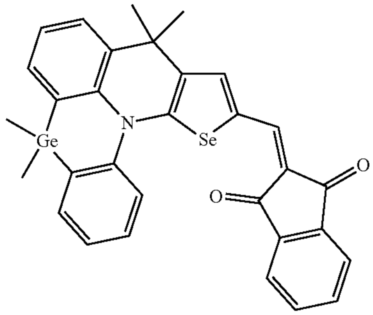
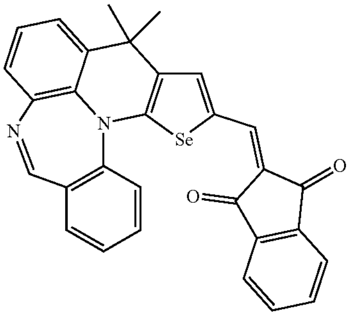
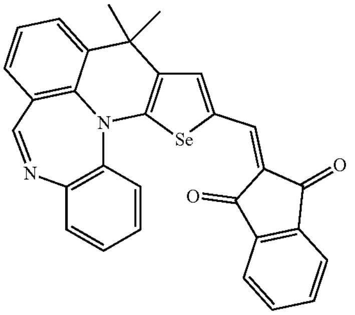
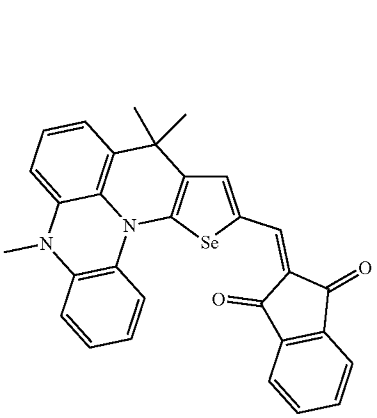
-continued
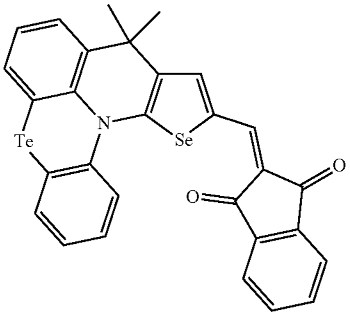
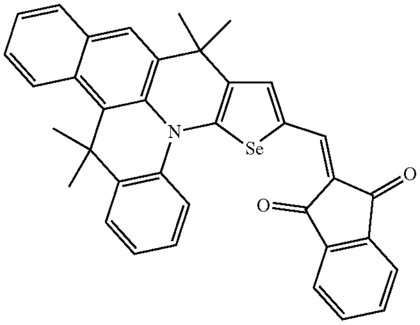
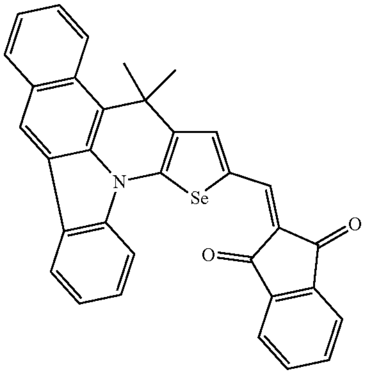
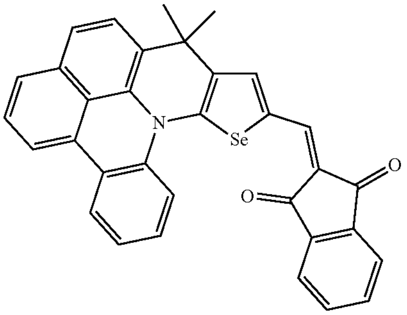
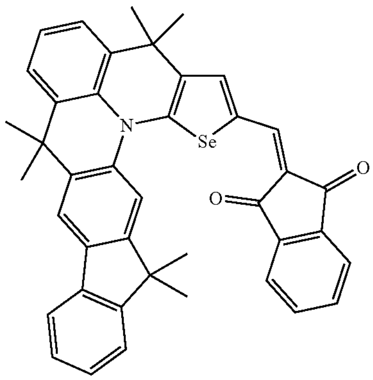

-continued
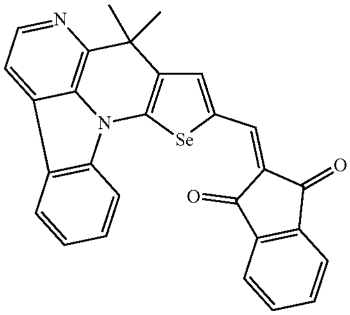
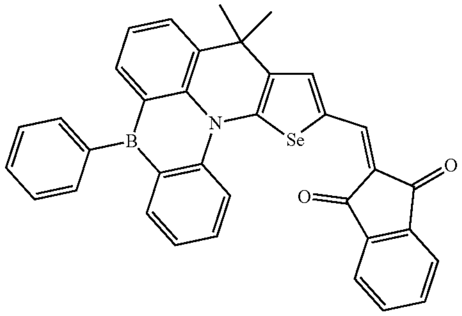
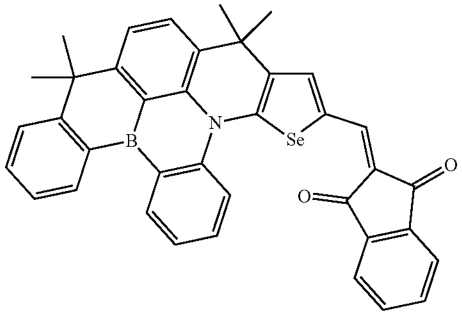
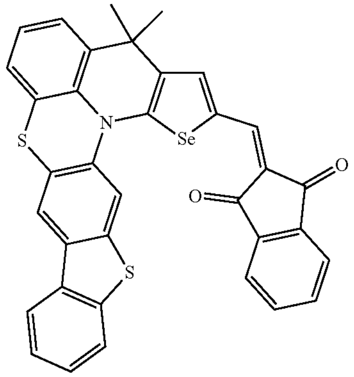
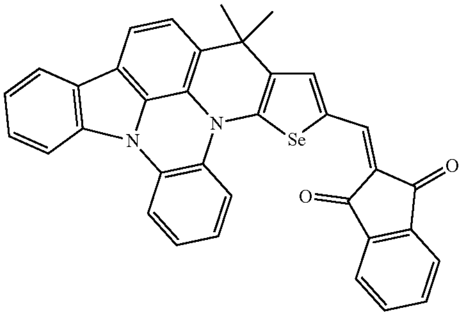
-continued
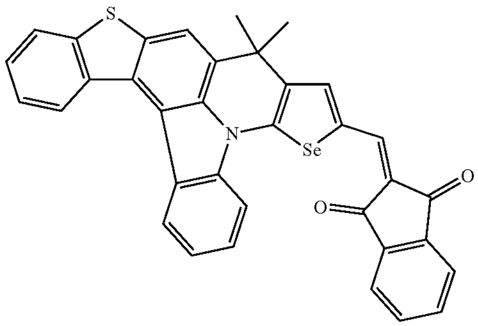
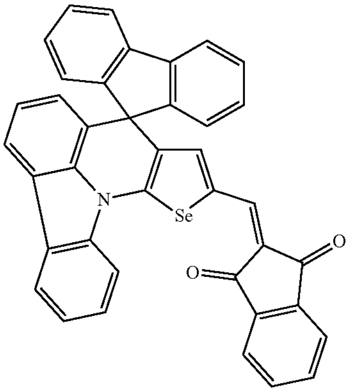
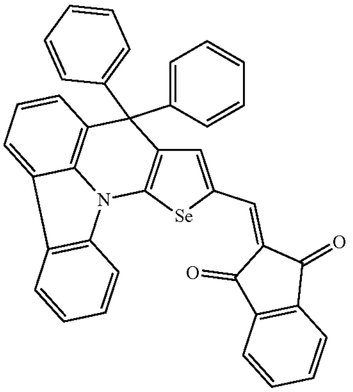
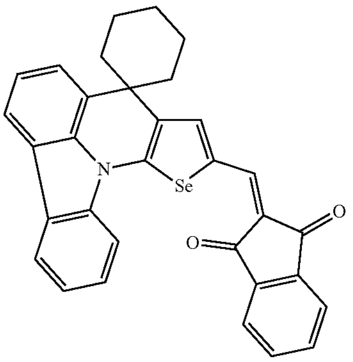

-continued
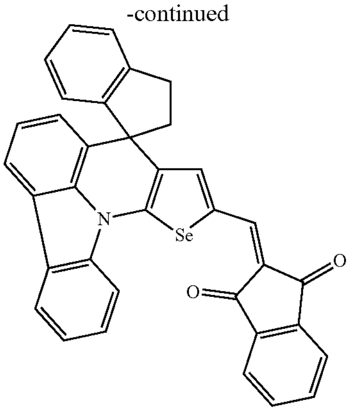
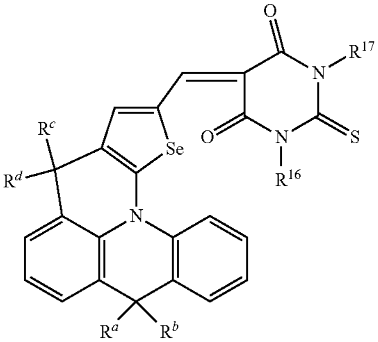
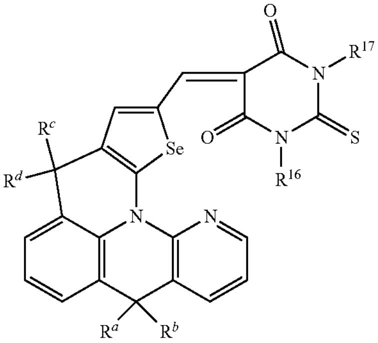
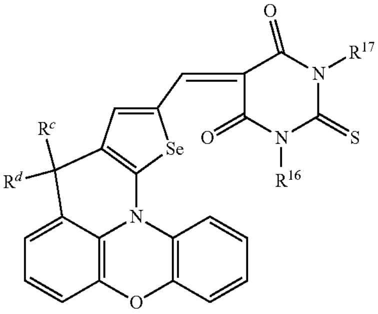
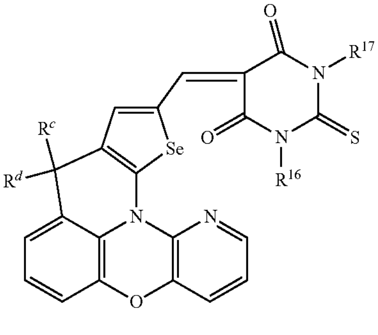
-continued
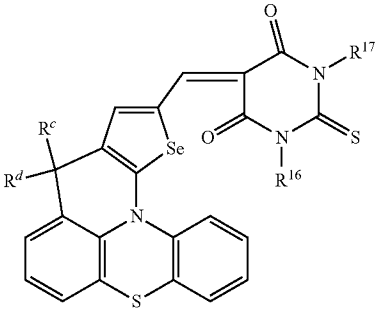
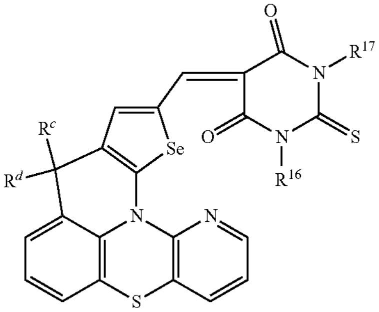
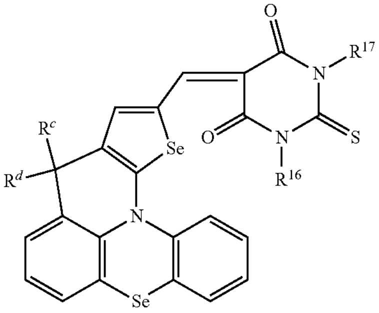
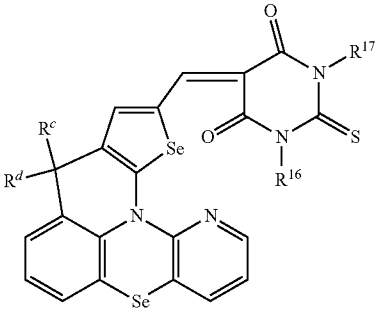
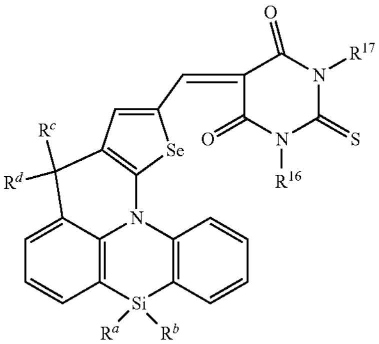

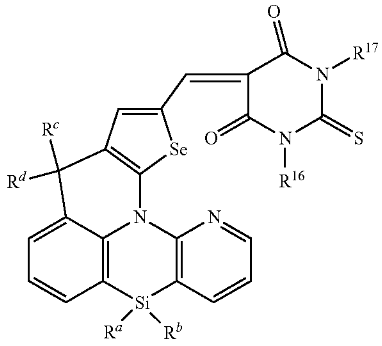
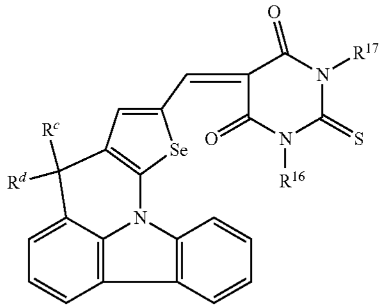
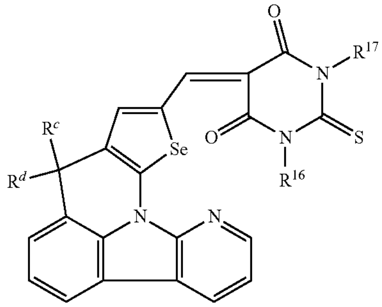
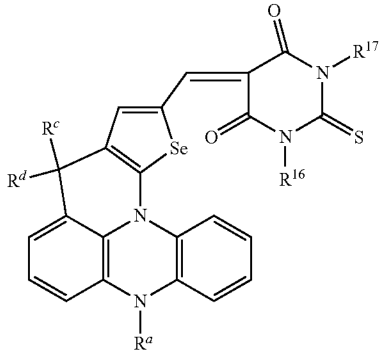
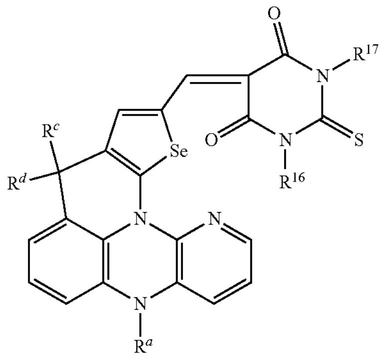
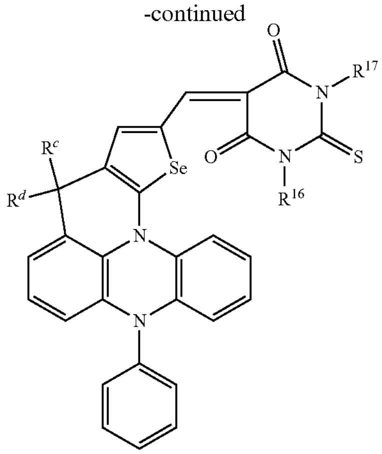
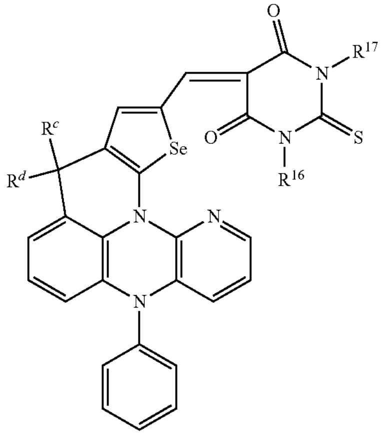
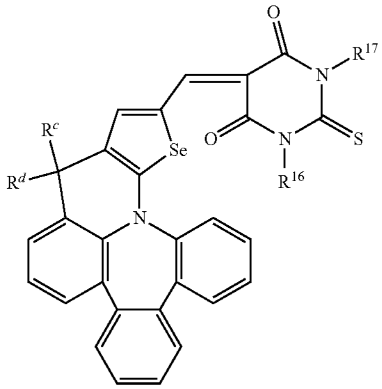
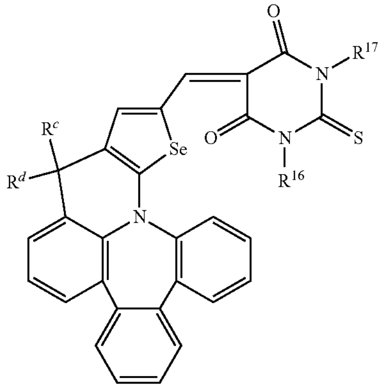

-continued

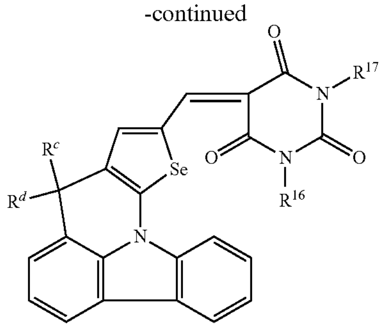

In Group 2C, at least one hydrogen present in each aromatic ring or heteroaromatic ring may each independently replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and any combination thereof, and $R^a$, $R^b$, $R^c$, $R^d$, $R^{16}$, and $R^{17}$ may each independently be hydrogen or a substituted or unsubstituted C1 to C6 alkyl group.

For example, the n-type semiconductor may be fullerene or a fullerene derivative, thiophene or a thiophene derivative, or any combination thereof, but is not limited thereto.

The photoelectric conversion layer 130 may be an intrinsic layer (1-layer) in which a p-type semiconductor and an n-type semiconductor are blended in a form of a bulk heterojunction. The p-type semiconductor and the n-type semiconductor may be blended in a volume ratio (e.g., thickness ratio) of about 1:9 to about 9:1, and within the above range, about 2:8 to about 8:2, within the above range, about 3:7 to about 7:3, within the above range, about 4:6 to about 6:4, or within the above range, about 5:5.

The photoelectric conversion layer 130 may include a bi-layer including a p-type layer including the aforementioned p-type semiconductor and an n-type layer including the aforementioned n-type semiconductor. In this case, the volume ratio (e.g., thickness ratio) of the p-type layer and the n-type layer may be about 1:9 to about 9:1, and within the above range, for example, about 2:8 to about 8:2, about 3:7 to about 7:3, about 4:6 to about 6:4, or about 5:5.

The photoelectric conversion layer 130 may further include a p-type layer and/or an n-type layer in addition to the intrinsic layer. The p-type layer may include the aforementioned p-type semiconductor, and the n-type layer may include the aforementioned n-type semiconductor. For example, the photoelectric conversion layer 130 may include in various combinations such as p-type layer/I-layer, I-layer/n-type layer, p-type layer/I-layer/n-type layer, and the like.

The photoelectric conversion layer 130 may have a thickness of about 1 nm to about 500 nm, and within the above range, about 5 nm to about 300 nm. Within the above thickness range, photoelectric conversion efficiency may be effectively improved by effectively absorbing light and effectively separating and transferring holes and electrons.

The auxiliary layers 140 and 150 may include a first auxiliary layer 140 between the first electrode 110 and the photoelectric conversion layer 130 and a second auxiliary layer 150 between the second electrode 120 and the photoelectric conversion layer 130. The first and second auxiliary layers 140 and 150 may each independently be a charge auxiliary layer for controlling the mobility of holes and/or electrons separated from the photoelectric conversion layer 130 or a light absorption auxiliary layer for improving light absorption characteristics.

The first and second auxiliary layers 140 and 150 may each include an independent organic material, an inorganic material, and/or an organic-inorganic material. The first and second auxiliary layers 140 and 150 may include at least one of a hole injecting layer HIL, a hole transporting layer HTL, an electron blocking layer EBL, and an electron injecting layer EIL, an electron transporting layer ETL, a hole blocking layer HBL, and a light absorption auxiliary layer, but are not limited thereto.

The hole injection layer, the hole transport layer, and/or the electron blocking layer may include, for example, a phthalocyanine compound such as copper phthalocyanine; DNTPD (N,N'-diphenyl-N,N'-bis-[4-(phenyl-m-tolyl-amino)-phenyl]-biphenyl-4,4'-diamine), m-MTDATA (4,4',4"-[tris(3-methylphenyl)phenylamino]triphenylamine), TDATA (4,4'4"-tris(N,N-diphenylamino)triphenylamine), 2-TNATA (4,4',4"-tris{(2-naphthyl)-N-phenylamino}-triphenylamine), PEDOT/PSS (poly(3,4-ethylenedioxythiophene)/poly(4-styrenesulfonate)), PANI/DBSA (polyaniline/dodecylbenzenesulfonic acid), PANI/CSA (polyaniline/Camphor sulfonic acid), PANI/PSS (polyaniline/poly(4-styrenesulfonate)), NPB (N,N'-di(naphthalene-l-yl)-N,N'-diphenylbenzidine), polyetherketone including triphenylamine (TPAPEK), 4-isopropyl-4'-methyldiphenyliodonium[tetrakis(pentafluorophenyl)borate], HAT-CN (dipyrazino[2,3-f: 2',3'-h] quinoxaline-2,3,6,7,10,11-hexacarbonitrile), a carbazole-based derivative such as N-phenylcarbazole, polyvinylcarbazole, and the like, a fluorene-based derivative, TPD (N,N'-bis(3-methylphenyl)-N,N'-diphenyl-[1,1-biphenyl]-4,4'-diamine), a triphenylamine-based derivative such as TCTA (4,4',4"-tris(N-carbazolyl)triphenylamine), NPB (N,N'-di(naphthalene-1-yl)-N,N'-diphenylbenzidine), TAPC (4,4'-cyclohexylidene bis[N,N-bis(4-methylphenyl)benzenamine]), HMTPD (4,4'-bis[N,N'-(3-tolyl)amino]-3,3'-dimethylbiphenyl), mCP (1,3-bis(N-carbazolyl)benzene), or any combination thereof, but is not limited thereto.

The electron injection layer, the electron transport layer, and/or the hole blocking layer may include, for example, a halogenated metal such as LiF, NaCl, CsF, RbCl, and RbI; a lanthanide metal such as Yb; a metal such as calcium (Ca), potassium (K), aluminum (Al), or an alloy thereof; a metal oxide such as $Li_2O$ or BaO; Liq (lithium quinolate), Alq3 (tris(8-hydroxyquinolinato)aluminum), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzimidazol-1-ylphenyl)-9,10-dinaphthylanthracene, TPBi (1,3,5-tri(1-phenyl-1H-benzo[d]imidazol-2-yl)phenyl), BCP (2,9-dimethyl-4,7-diphenyl-1,10-phenanthroline), Bphen (4,7-diphenyl-1,10-phenanthroline), TAZ (3-(4-biphenylyl)-4-phenyl-5-tertbutylphenyl-1,2,4-triazole), NTAZ (4-(naphthalen-1-yl)-3,5-diphenyl-4H-1,2,4-triazole), tBu-PBD (2-(4-biphenylyl)-5-(4-tert-butylphenyl)-1,3,4-oxadiazole), BAlq (bis(2-methyl-8-quinolinolato-N1,O8)-(1,1'-biphenyl-4-olato)aluminum), $Bebq_2$ (berylliumbis(benzoquinolin-10-olate), ADN (9,10-di(naphthalene-2-yl)anthracene), BmPyPhB (1,3-bis[3,5-di(pyridin-3-yl)phenyl]benzene), or any combination thereof, but is not limited thereto.

The light absorption auxiliary layer may include, for example, fullerene or a fullerene derivative.

Any one of the first or second auxiliary layers 140 or 150 may be omitted.

The buffer layer 160 may be between the first electrode 110 and the second electrode 120. The buffer layer 160 may be, for example, between the first electrode 110 and the photoelectric conversion layer 130, for example, between the photoelectric conversion layer 130 and the first auxiliary layer 140. For example, the buffer layer 160 may be in contact with the photoelectric conversion layer 130. For example, one surface of the buffer layer 160 may be in contact with the photoelectric conversion layer 130 and the other surface of the buffer layer 160 may be in contact with the first auxiliary layer 140 (or the first electrode 110).

The buffer layer 160 may be an organic buffer layer including an organic buffer material, and may include the aforementioned compound as the organic buffer material.

The compound may satisfy a particular (or, alternatively, predetermined) energy level due to the structure having an asymmetric core as described above. Accordingly, the buffer layer 160 including the aforementioned compound as an organic buffer material may effectively extract first charge carriers (e.g., holes) separated from the photoelectric conversion layer 130 toward the first electrode 110, while simultaneously reduce or prevent second charge carriers (e.g., electrons) from being injected back to the photoelectric conversion layer 130 from the first electrode 110 when a voltage is applied from the outside. Accordingly, electrical characteristics of the sensor 100 may be improved by increasing the photoelectric conversion efficiency of the sensor 100 and at the same time effectively reducing dark current and remaining charge carriers.

For example, the HOMO energy level of the buffer layer 160 including the compound may have a small difference from the HOMO energy level of the p-type semiconductor of the photoelectric conversion layer 130. For example, a difference between the HOMO energy level of the compound and the HOMO energy level of the p-type semiconductor may be less than or equal to about 0.5 eV, within the range, about 0 eV to about 0.5 eV, about 0 eV to about 0.4 eV, about 0 eV to about 0.3 eV, about 0 eV to about 0.2 eV, or about 0 eV to about 0.1 eV. For example, the HOMO energy level of the compound and the HOMO energy level of the p-type semiconductor may be about 5.0 eV to about 6.0 eV, respectively.

Herein, the HOMO energy level of the compound and the HOMO energy level of the p-type semiconductor may be evaluated as the amount of photoelectrons emitted according to energy generated by irradiating UV light on a thin film using AC-3 (Riken Keiki Co., LTD.). The HOMO energy level of the compound and the HOMO energy level of the p-type semiconductor are expressed as absolute values, and a difference between the HOMO energy level of the compound and the HOMO energy level of the p-type semiconductor may be a value obtained by subtracting a small absolute value from a large absolute value.

For example, the energy bandgap of the compound (buffer layer 160) may be greater than or equal to about 2.6 eV, within the above range, greater than or equal to about 2.8 eV, greater than or equal to about 3.0 eV, about 2.6 eV to about 4.0 eV, about 2.8 eV to about 4.0 eV, or about 3.0 eV to about 4.0 eV.

For example, the compound may be a visible light non-absorbing material. The visible light non-absorbing material may be a material that does not substantially absorb light in the visible region of about 400 nm to about 700 nm. Accordingly, the optical properties of the sensor 100 may not be affected by the buffer layer 160.

In addition, the buffer layer 160 may be less dependent on a thickness for implementing the aforementioned electrical characteristics, and for example, accordingly, the aforementioned electrical characteristics may be substantially maintained regardless of a thickness of the buffer layer 160. For example, when the thickness of the buffer layer 160 is about 5 to about 6 times changed, the electrical characteristics (e.g., photoelectric conversion efficiency) may have a variation ratio of less than or equal to about 10%, for example, less than or equal to about 8%, less than or equal to about 6%, less than or equal to about 5%, or less than or equal to about 3%. Accordingly, the thickness of the buffer layer 160 may be selected within a wide range without deteriorating the electrical characteristics.

In addition, the compound may have a relatively high glass transition temperature due to the structure having an asymmetric core, as described above, and accordingly, the buffer layer 160 including this compound as an organic buffer material may have high heat resistance which may not be easily deteriorated during the subsequent process.

For example, the aforementioned compound may be a depositable organic compound having relatively high heat resistance. For example, a temperature $Ts_{10}$ of the compound at which a weight loss of 10% relative to the initial weight occurs during thermogravimetric analysis at a pressure of less than or equal to about 1 Pa may be about 180° C. to about 450° C., about 190° C. to about 450° C., about 200° C. to about 450° C., about 210° C. to about 450° C. or about 220° C. to about 450° C. and a temperature $Ts_{50}$ of the compound at which a weight loss of 50% relative to the initial weight occurs may be about 200° C. to about 500° C., about 220° C. to about 500° C., or about 250° C. to about 500° C. By having such high heat resistance, the compound may be stably repeatedly deposited and may maintain good performance without deterioration in subsequent high temperature processes.

In addition to the aforementioned first and second auxiliary layers 140 and 150 and the buffer layer 160, the sensor 100 may further include one or more auxiliary layers (not shown) between the first electrode 110 and the photoelectric conversion layer 130 and/or between the second electrode 120 and the photoelectric conversion layer 130. The auxiliary layer may be between the first electrode 110 and the first auxiliary layer 140, between the first auxiliary layer 140 and the buffer layer 160, between the buffer layer 160 and the photoelectric conversion layer 130, between the second electrode 120 and the second auxiliary layer 150, and/or between the photoelectric conversion layer 130 and the second auxiliary layer 150. The auxiliary layer may include an organic material, an inorganic material, and/or an organic-inorganic material.

The sensor 100 may further include an anti-reflection layer (not shown) under the first electrode 110 or on the second electrode 120. For example, when the first electrode 110 is a light-receiving electrode, the anti-reflection layer may be under the first electrode 110. For example, when the second electrode 120 is a light-receiving electrode, the anti-reflection layer may be on the second electrode 120. The anti-reflection layer is disposed at a light incidence side and may lower reflectance of light of incident light and thereby light absorbance may be further improved. The anti-reflection layer may include, for example a material having a refractive index of about 1.6 to about 2.5, and may include for example at least one of metal oxide, metal sulfide, or an organic material having a refractive index within the ranges. The anti-reflection layer may include, for example a metal oxide such as aluminum-containing oxide, molybdenum-containing oxide, tungsten-containing oxide, vanadium-containing oxide, rhenium-containing oxide, niobium-containing oxide, tantalum-containing oxide, titanium-containing oxide, nickel-containing oxide, copper-containing oxide, cobalt-containing oxide, manganese-containing oxide, chromium-containing oxide, tellurium-containing oxide, or any combination thereof; a metal sulfide such as zinc sulfide; or an organic material such as an amine derivative, but is not limited thereto.

The sensor 100 may further include a focusing lens (not shown). The focusing lens may collect the light to a single point by controlling the direction of the incident light at a light incident position. The focusing lens may have a shape of, for example, a cylinder or a hemisphere, but is not limited thereto.

In the sensor 100, when light enters from the first electrode 110 or the second electrode 120 and the photoelectric conversion layer 130 may absorb light in a particular (or, alternatively, predetermined) wavelength region, excitons may be produced thereinside. The excitons may be separated into holes and electrons in the photoelectric conversion layer 130, and the separated holes are transported to an anode that is one of the first electrode 110 or the second electrode 120 and the separated electrons are transported to the cathode that is the other of the first electrode 110 or the second electrode 120 so as to flow a current.

The sensor 100 may be included in, for example, an image sensor or a biometric sensor.

For example, the aforementioned sensor 100 may be included in an image sensor, and as described above, has improved optical and electrical properties and reduces an image afterimage due to remaining charges, thereby being applied to an image sensor suitable for high-speed photographing.

Hereinafter, an image sensor according to some example embodiments is described.

Figure 2:
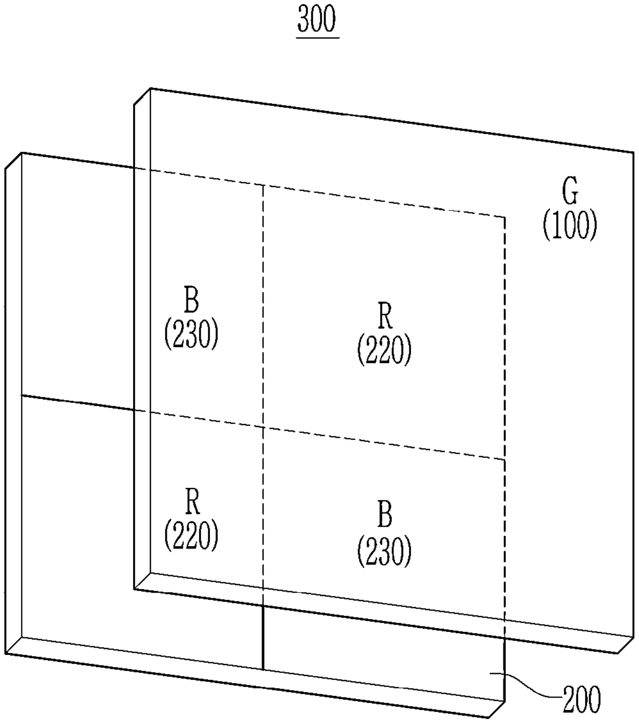
FIG. 2 is a plan view showing an example of an image sensor according to some example embodiments.
Figure 3:
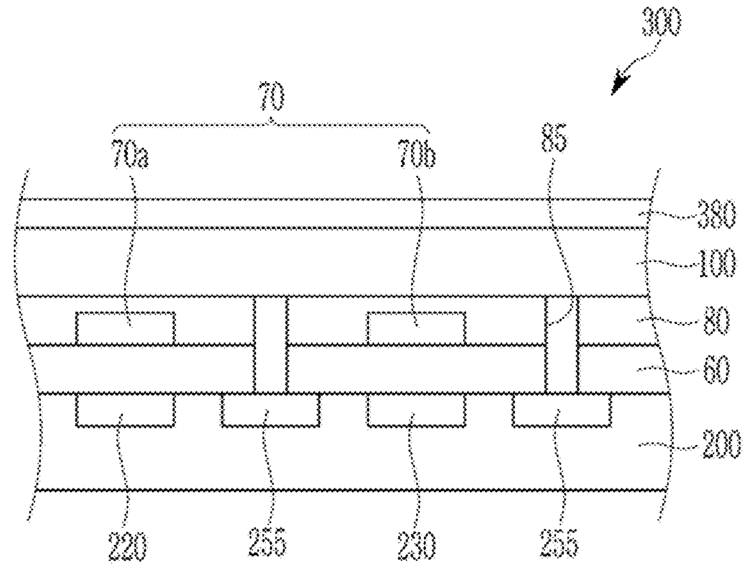
FIG. 3 is a cross-sectional view showing an example of the image sensor of FIG. 2.

FIG. 2 is a plan view showing an example of an image sensor according to some example embodiments, and FIG. 3 is a cross-sectional view showing an example of the image sensor of FIG. 2.

Referring to FIG. 2, the image sensor 300 according to some example embodiments may be a stacked sensor in which a semiconductor substrate 200 and the aforementioned sensor 100 are stacked, and the semiconductor substrate 200 includes a first photodiode 220 and a second photodiode 230 which are overlapped with the sensor 100. FIG. 2 illustrates an example of a repeating unit pixel group in the image sensor 300, and the unit pixel group is repeatedly arranged along rows and/or columns. In FIG. 2, the unit pixel group is shown as a 2×2 array in which two red pixels R and two blue pixels B are arranged on a semiconductor substrate 200, but not limited thereto.

A first photodiode 220 and a second photodiode 230 are each integrated in the semiconductor substrate 200 and thus may be configured to absorb and convert light each having different wavelength spectrum which is filtered by a color filter layer 70, which will be described later. A wavelength spectrum photoelectrically converted in the sensor 100 may be different respectively from the wavelength spectra photoelectrically converted in the first photodiode 220 and the second photodiode 230, for example, the wavelength spectrum photoelectrically converted in the first photodiode 220 and the wavelength spectrum photoelectrically converted in the second photodiode 230 may be respectively different from the wavelength spectrum photoelectrically converted in the sensor 100 and selected from light of a red wavelength spectrum, a green wavelength spectrum, and a blue wavelength spectrum. For example, the first photodiode 220 may be configured to photoelectrically convert light of the red wavelength spectrum R, the second photodiode 230 may be configured to photoelectrically convert light of the blue wavelength spectrum B, and the sensor 100 may be configured to photoelectrically convert light of the green wavelength spectrum G.

Referring to FIG. 3, an image sensor 300 according to some example embodiments includes a substrate 200, a lower insulation layer 60, a color filter layer 70, an upper insulation layer 80, a sensor 100, and an encapsulation layer 380.

The substrate 200 may be a semiconductor substrate, and the first and second photodiodes 220 and 230, a transmission transistor (not shown) and the charge storage 255 are integrated therein. The first or second photodiode 220 or 230, transmission transistor and/or charge storage 255 may be integrated for each pixel. As shown in the drawing, the first photodiode 220 may be included in the red pixel R and the second photodiode 230 may be included in the blue pixel B. The charge storage 255 is electrically connected to the sensor 100.

A metal wire (not shown) and a pad (not shown) are formed on the lower portion or upper portion of the substrate 200. In order to decrease signal delay, the metal wire and pad may be made of a metal having low resistivity, for example, aluminum Al, copper Cu, silver Ag, and alloys thereof, but is not limited thereto.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench 85 exposing the charge storage 255. The trench 85 may be filled with fillers.

The color filter layer 70 is formed on the lower insulation layer 60. The color filter layer 70 includes a red filter **70*a* formed in the red pixel R and a blue filter 70*b* formed in the blue pixel B. However, the present inventive concepts are not limited thereto, and a cyan filter, a magenta filter, and/or a yellow filter may be included instead of the red filter 70*a* and/or the blue filter 70*b*, or may be additionally included in addition to the red filter 70*a* and the blue filter 70*b*. Although an example in which the green filter is not provided is described in some example embodiments, including the example embodiments shown in FIG. 3**, a green filter may be provided in some example embodiments.

The upper insulation layer 80 is formed on the color filter layer 70. The upper insulation layer 80 removes the step difference caused by the color filter layer 70 and is planarized. The upper insulation layer 80 and the lower insulation layer 60 have a contact (not shown) exposing the pad and a trench 85 exposing the charge storage 255.

The aforementioned sensor 100 is formed on the upper insulation layer 80. A detailed description of the sensor 100 is the same as described above. One of the first electrode 110 and the second electrode 120 of the sensor 100 may be electrically connected to the charge storage 255 and the other of the first electrode 110 and the second electrode 120 of the sensor 100 may be a light-receiving electrode. For example, the first electrode 110 of the sensor 100 may be electrically connected to the charge storage 255, and the second electrode 120 of the sensor 100 may be a light-receiving electrode.

The encapsulation layer 380 may protect the image sensor 300, and may include a thin film of one or two or more layers including an organic material, an inorganic material, an organic-inorganic material, or any combination thereof. The encapsulation layer 380 may include, for example, a glass plate, a metal thin film, an organic layer, an inorganic layer, an organic-inorganic layer, or any combination thereof. The organic film may include, for example, an acrylic resin, a (meth)acrylic resin, polyisoprene, a vinyl resin, an epoxy resin, a urethane resin, a cellulose resin, a perylene resin, or any combination thereof, but is not limited thereto. The inorganic film may include, for example, an oxides, a nitride, and/or an oxynitride, for example silicon oxide, silicon nitride, silicon oxynitride, aluminum oxide, aluminum nitride, aluminum oxynitride, zirconium oxide, zirconium nitride, zirconium oxynitride, titanium oxide, titanium nitride, titanium oxynitride, hafnium oxide, hafnium nitride, hafnium oxynitride, tantalum oxide, tantalum nitride, tantalum oxynitride, lithium fluoride, or any combination thereof, but is not limited thereto. The organic-inorganic film may include, for example, polyorganosiloxane, but is not limited thereto. The encapsulation layer 380 may be one layer or two or more layers. The encapsulation layer 380 may be omitted.

A focusing lens (not shown) may be further formed on the sensor 100 (or the encapsulation layer 380). The focusing lens may control the direction of the incident light to collect the light to a single point. The focusing lens may have a shape of, for example, a cylinder or a hemisphere, but is not limited thereto.

Figure 4:
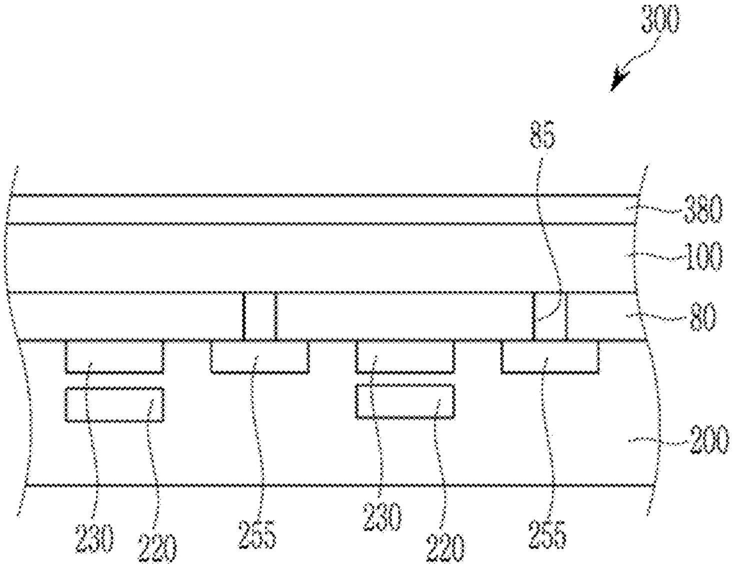
FIG. 4 is a cross-sectional view showing another example of the image sensor of FIG. 2.

FIG. 4 is a cross-sectional view showing another example of the image sensor of FIG. 2.

Referring to FIG. 4, the image sensor 300 according to some example embodiments includes a semiconductor substrate 200 integrated with the first and second photodiodes 220 and 230, a transmission transistor (not shown), and a charge storage 255, an upper insulation layer 80, a sensor 100, and an encapsulation layer 380, like some example embodiments, including the example embodiments shown in FIG. 3.

However, in the image sensor 300 according to this example, the first and second photodiodes 220 and 230 are stacked in a vertical direction with respect to the in-plane direction of the semiconductor substrate 200, and the color filter layer 70 and the lower insulation layer 60 are omitted, unlike some example embodiments, including the example embodiments shown in FIG. 3. The first and second photodiodes 220 and 230 are electrically connected to a charge storage (not shown) and may be transferred by a transmission transistor. The first and second photodiodes 220 and 230 may be configured to selectively absorb light in each wavelength region according to the stacking depth.

The sensor 100 is the same as described above. One of the first electrode 110 or the second electrode 120 of the sensor 100 may be a light-receiving electrode, and the other of the first electrode 110 and the second electrode 120 of the sensor 100 may be electrically connected to the charge storage 255.

Figure 5:
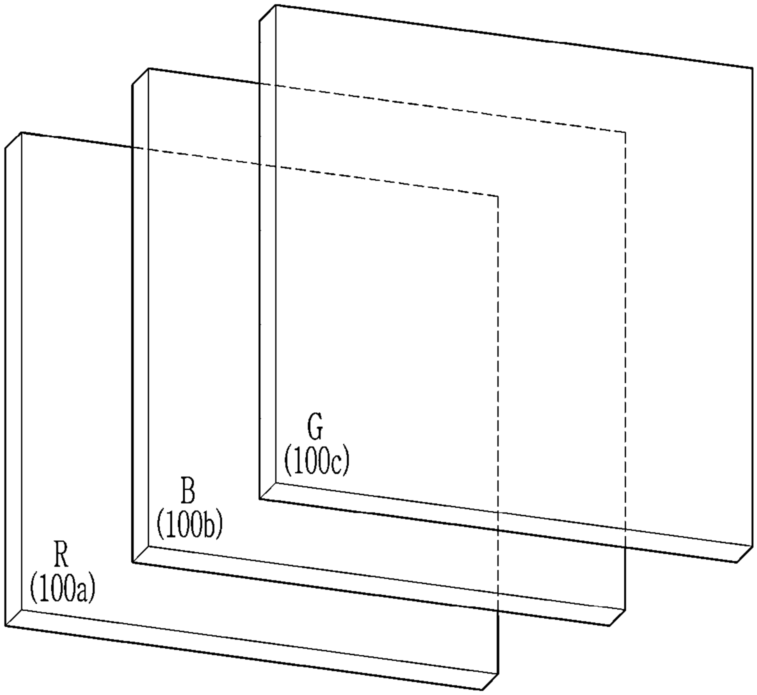
FIG. 5 is a plan view showing another example of an image sensor according to some example embodiments.
Figure 6:
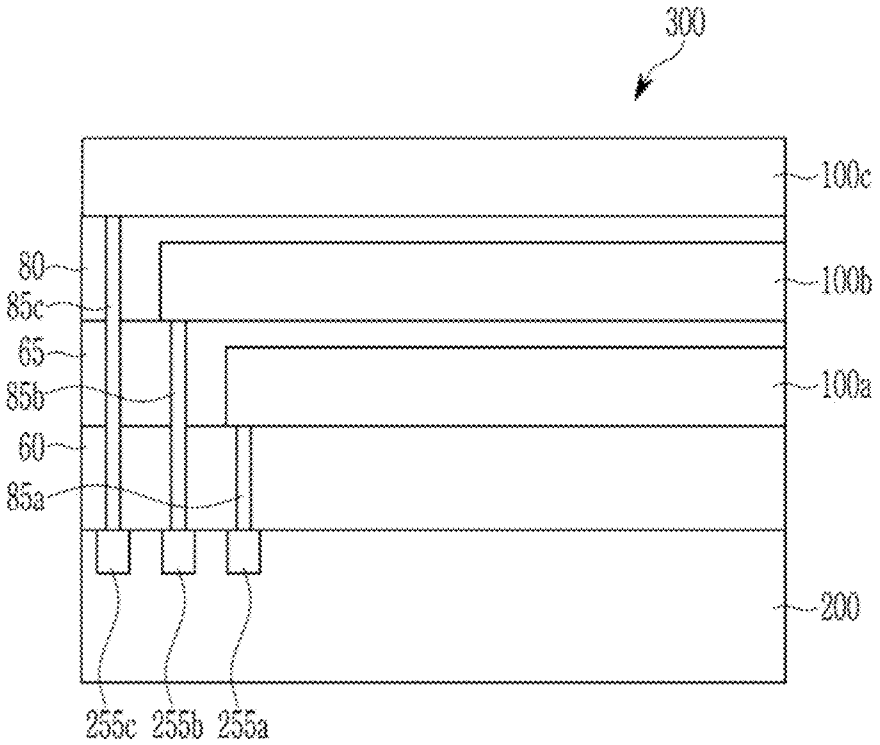
FIG. 6 is a cross-sectional view showing an example of the image sensor of FIG. 5.

FIG. 5 is a plan view showing another example of an image sensor according to some example embodiments, and FIG. 6 is a cross-sectional view showing an example of the image sensor of FIG. 5.

The image sensor 300 according to some example embodiments, including the example embodiments shown in FIGS. 5 and 6 may have a structure in which a green sensor configured to selectively absorb light in a green wavelength spectrum, a blue sensor configured to selectively absorb light in a blue wavelength spectrum, and a red sensor configured to selectively absorb light in a red wavelength spectrum are stacked.

The image sensor 300 according to some example embodiments includes a substrate 200, a lower insulation layer 60, an intermediate insulation layer 65, an upper insulation layer 80, a first sensor **100*a*, a second sensor 100*b*, and a third sensor 100*c***.

The substrate 200 may be a semiconductor substrate such as a silicon substrate, and a transmission transistor (not shown) and charge storages **255*a*, 255*b*, and 255*c*** are integrated.

A metal wire (not shown) and a pad (not shown) are formed on the substrate 200, and a lower insulation layer 60 is formed on the metal wire and the pad.

The first sensor **100*a*, the second sensor 100*b*, and the third sensor 100*c* are sequentially formed on the lower insulation layer 60**.

At least one of the first, second, or third sensors **100*a*, 100*b*, and 100*c* may be the aforementioned sensor 100. For example, one of the first, second, and third sensors 100*a*, 100*b*, and 100*c* may be the aforementioned sensor 100, and the rest two may be conventional sensors in the present field, For another example, the first, second, and third sensors 100*a*, 100*b*, and 100*c* may each be the aforementioned sensor 100. One of the first electrode 110 or the second electrode 120 of the first, second, and third sensors 100*a*, 100*b*, and 100*c* may be a light-receiving electrode, and the other of the first electrode 110 and the second electrode 120 of the first, second, and third sensors 100*a*, 100*b*, and 100*c* may be connected to the charge storages 255*a*, 255*b*, and 255*c***.

The first sensor **100*a* may be configured to selectively absorb light in any one wavelength region of red, blue, or green to photoelectrically convert it. For example, the first sensor 100*a* may be a red sensor. The intermediate insulation layer 65 is formed on the first sensor 100*a***.

The second sensor **100*b* is formed on the intermediate insulation layer 65. The second sensor 100*b* may be configured to selectively absorb light of any one wavelength region among red, blue, or green to photoelectrically convert it. For example, the second sensor 100*b*** may be a blue sensor.

The upper insulation layer 80 is formed on the second sensor **100*b*. The lower insulation layer 60, the intermediate insulation layer 65, and the upper insulation layer 80 have a plurality of trenches 85*a*, 85*b*, and 85*c* exposing charge storages 255*a*, 255*b*, and 255*c***.

The third sensor **100*c* is formed on the upper insulation layer 80. The third sensor 100*c* may be configured to selectively absorb light of any one wavelength region among red, blue, or green to photoelectrically convert it. For example, the third sensor 100*c*** may be a green sensor.

A focusing lens (not shown) may be further formed on the third sensor **100*c***. The focusing lens may control the direction of the incident light to collect the light to a single point. The focusing lens may have a shape of, for example, a cylinder or a hemisphere, but is not limited thereto.

Although the drawing shows a structure in which the first sensor **100*a*, the second sensor 100*b*, and the third sensor 100*c*** are sequentially stacked, the stacking order is not limited thereto and the stacking order may be variously changed.

As described above, the first sensor **100*a*, the second sensor 100*b*, and the third sensor 100*c*** configured to absorb light in different wavelength spectra are stacked, thereby further reducing a size of the image sensor to provide a miniaturized image sensor.

Figure 7:
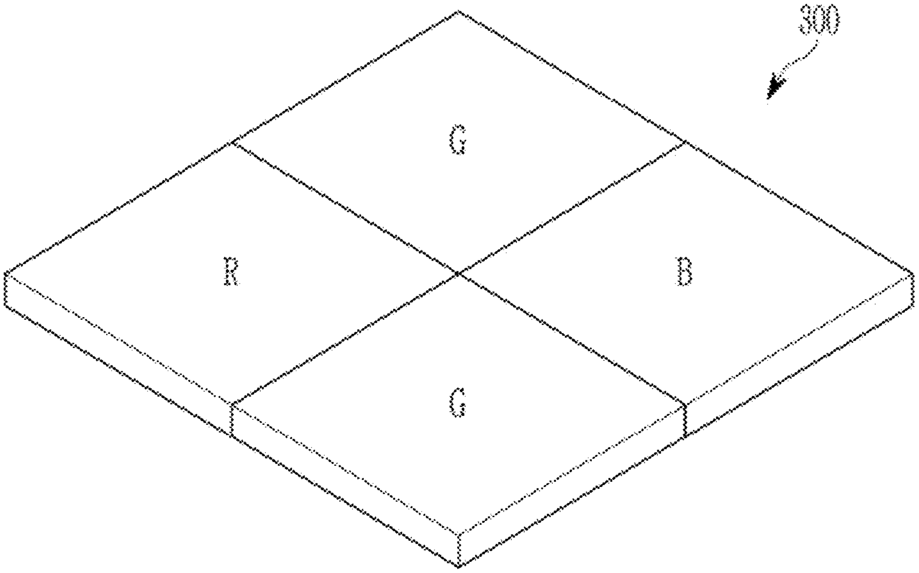
FIG. 7 is a plan view showing another example of an image sensor according to some example embodiments.
Figure 8:
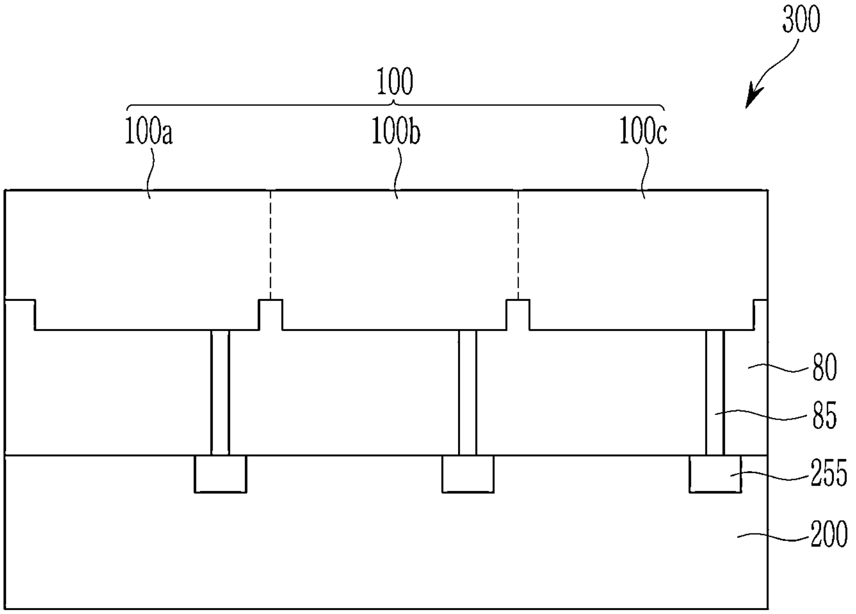
FIG. 8 is a cross-sectional view showing an example of the image sensor of FIG. 7.

FIG. 7 is a plan view showing another example of an image sensor according to some example embodiments, and FIG. 8 is a cross-sectional view showing an example of the image sensor of FIG. 7.

Referring to FIGS. 7 and 8, the image sensor 300 includes an insulation layer 80 on the semiconductor substrate 200 and the sensor 100 on the insulation layer 80, and the sensor 100 includes the first, second, and third sensors 100*a*, 100*b*, and 100*c*. The first, second, and third sensors 100*a*, 100*b*, and 100*c* may be configured to convert light of different wavelength spectra (e.g., blue light, green light, or red light) into electrical signals.

Referring to FIG. 8, the first, second, and third sensors 100*a*, 100*b*, and 100*c* are arranged in a parallel direction to the surface of the substrate 200 unlike some example embodiments, including the example embodiments shown in FIGS. 5 and 6. Each first, second, and third sensor 100*a*, 100*b*, and 100*c* is electrically connected to the charge storage 255 integrated in the substrate 200 through the trench 85.

For example, the aforementioned sensor 100 may be included in a display panel, and may be, for example, applied to a sensor-embedded display panel in which the sensor 100 is embedded in the display panel.

Hereinafter, a sensor-embedded display panel including the aforementioned sensor is described.

The sensor-embedded display panel according to some example embodiments may be a display panel capable of performing a display function and a recognition function (e.g., biometric recognition function), and may be an in-cell type display panel in which a sensor performing a recognition function (e.g., biometric recognition function) is embedded in the display panel.

Figure 9:
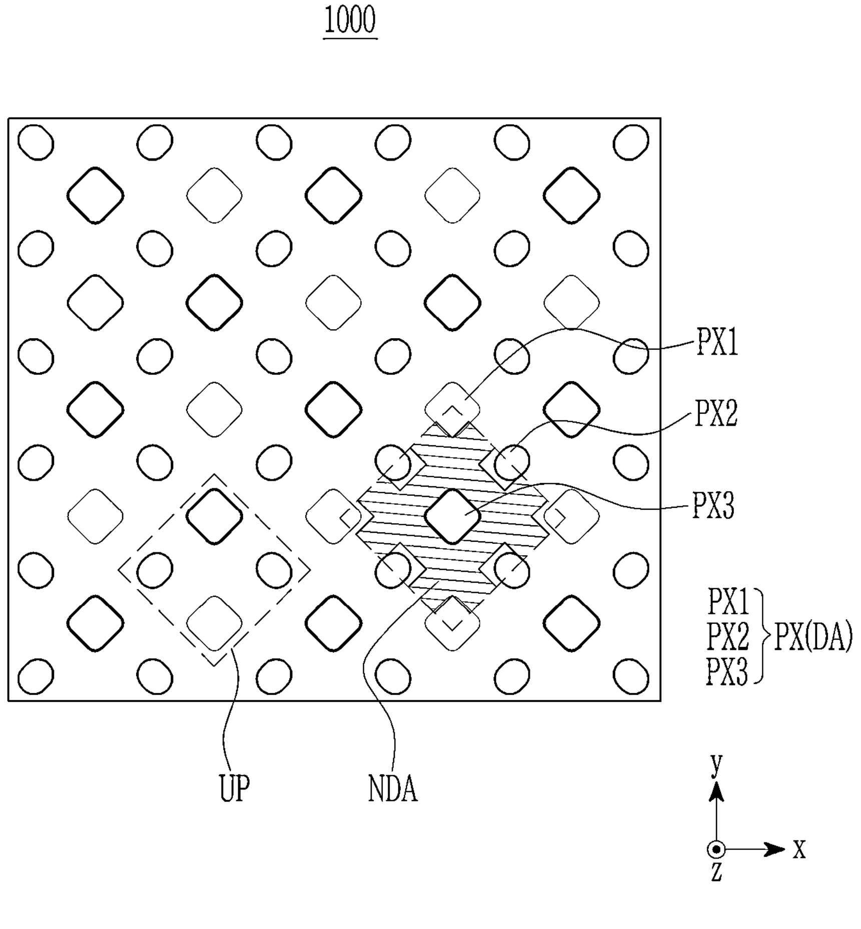
FIG. 9 is a plan view illustrating an example of a sensor-embedded display panel according to some example embodiments.
Figure 10:
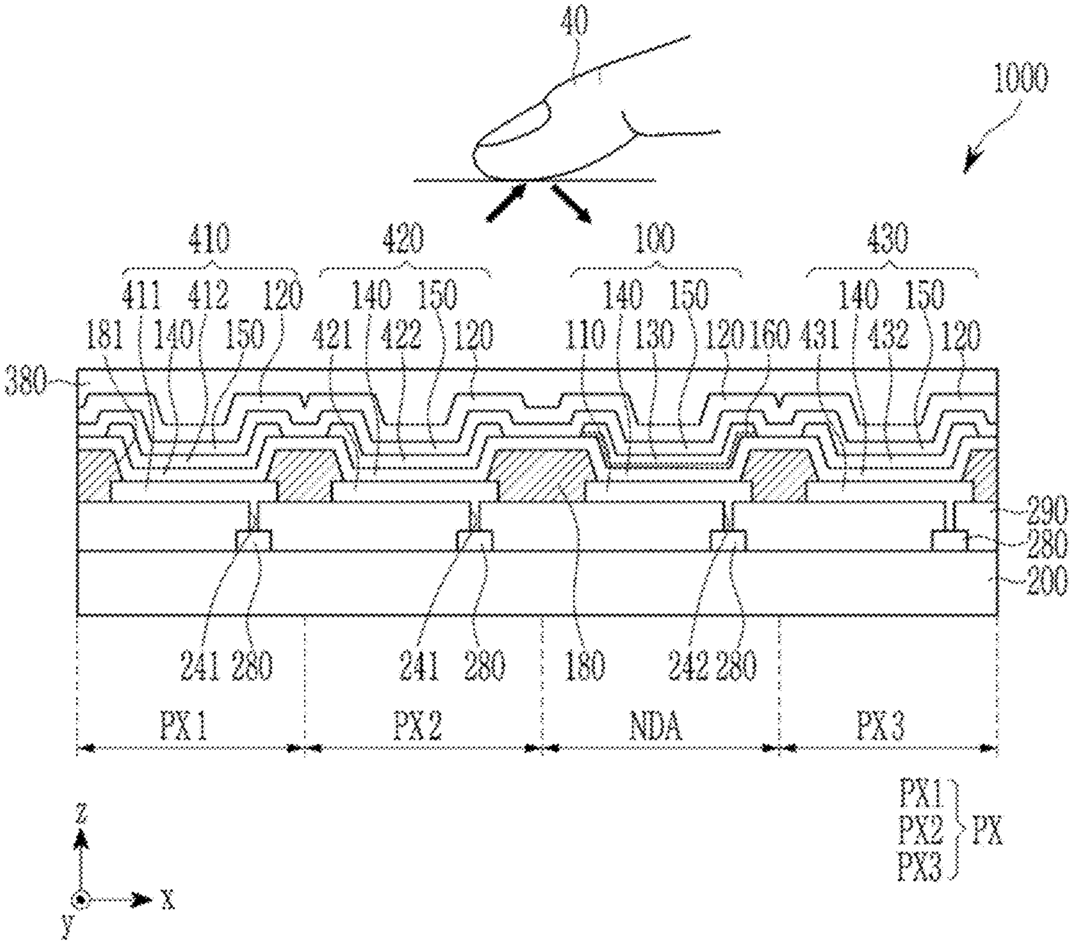
FIG. 10 is a cross-sectional view illustrating an example of a sensor-embedded display panel according to some example embodiments.

FIG. 9 is a plan view illustrating an example of a sensor-embedded display panel according to some example embodiments, and FIG. 10 is a cross-sectional view illustrating an example of a sensor-embedded display panel according to some example embodiments.

Referring to FIGS. 9 and 10, a sensor-embedded display panel 1000 according to some example embodiments includes a plurality of subpixels PXs configured to display different colors. The plurality of subpixels PXs may be configured to display at least three primary colors, for example, a first subpixel PX1, a second subpixel PX2, and a third subpixel PX3 may be configured to display different first color, second color, and third color selected from red, green, and blue. For example, the first color, the second color, and the third color may be red, green, and blue, respectively. The first subpixel PX1 may be a red subpixel configured to display red, the second subpixel PX2 may be a green subpixel configured to display green, and the third subpixel PX3 may be a blue subpixel configured to display blue. However, the present inventive concepts are not limited thereto, and an auxiliary subpixel (not shown) such as a white subpixel may be further included.

The plurality of subpixels PXs including the first subpixel PX1, the second subpixel PX2, and the third subpixel PX3 may constitute one unit pixel UP to be arranged repeatedly along the row and/or column. In FIG. 9, a structure including one first subpixel PX1, two second subpixels PX2, and one third subpixel PX3 in the unit pixel UP is illustrated, but the present inventive concepts are not limited thereto. At least one first subpixel PX1, at least one second subpixel PX2, and at least one third subpixel PX3 may be included. In the drawing of FIGS. 9 and 10, as an example, an arrangement of a Pentile type is illustrated, but the present inventive concepts are not limited thereto. The subpixels PXs may be arranged variously. An area occupied by the plurality of subpixels PXs and configured to display colors by the plurality of subpixels PXs may be a display area DA configured to display an image.

Each of the first subpixel PX1, the second subpixel PX2, and the third subpixel PX3 may include a light emitting element. As an example, the first subpixel PX1 may include a first light emitting element 410 configured to emit light of a wavelength spectrum of a first color, the second subpixel PX2 may include a second light emitting element 420 configured to emit light of a wavelength spectrum of a second color, and the third subpixel PX3 may include a third light emitting element 430 configured to emit light of a wavelength spectrum of a third color. However, the present inventive concepts are not limited thereto, and at least one of the first subpixel PX1, the second subpixel PX2, or the third subpixel PX3 may include a light emitting element configured to emit light of any combination of a first color, a second color, or a third color, that is, light in a white wavelength spectrum, and may be configured to display a first color, a second color, or a third color through a color filter (not shown).

The sensor-embedded display panel 1000 according to some example embodiments includes the aforementioned sensor 100. The sensor 100 may be in a non-display area NDA. The non-display area NDA may be an area other than the display area DA, in which the first subpixel PX1, the second subpixel PX2, the third subpixel PX3, and auxiliary subpixels are not arranged. For example, the area (e.g., in the xy plane) of the sub-pixels (PX) may collectively define the display area (DA) that is configured to display an image thereon (e.g., configured to display one or more colors). A portion of the area (e.g., in the xy plane) of the sensor embedded display panel 1000 that excludes the display area (DA) (e.g., portions of the area of the sensor embedded display panel 1000 that are between adjacent subpixels (PX) in the xy direction, xy plane, etc.) may be a non-display area (NDA) that is configured to not display an image thereon (e.g., configured to not display any color). The sensor 100 may be between at least two selected from the first subpixel PX1, the second subpixel PX2, or the third subpixel PX3, and may be in parallel with the first, second, and third light emitting elements 410, 420, and 430 in the display area DA.

The sensor 100 may be an optical type recognition sensor (e.g., biometric sensor). The sensor 100 may be configured to absorb light emitted from at least one of the first, second or third light emitting elements 410, 420, and 430 in the display area DA and then reflected by a recognition target 40 such as a living body, a tool, or a thing, and convert the absorbed light into an electrical signal. Herein, the living body may be a finger, a fingerprint, a palm, an iris, a face, and/or a wrist, but is not limited thereto. The sensor 100 may be, for example, a fingerprint sensor, an illumination sensor, an iris sensor, a distance sensor, a blood vessel distribution sensor, and/or a heart rate sensor, but is not limited thereto.

The sensor 100 may be on the same plane as the first, second, and third light emitting elements 410, 420, and 430, and may be embedded in the display panel 1000.

Referring to FIG. 10, the sensor-embedded display panel 1000 includes a substrate 200; a thin film transistor 280 on the substrate 200; an insulation layer 290 on thin film transistor 280; a pixel definition layer 180 on the insulation layer 290; and first, second, or third light emitting elements 410, 420, and 430 and the sensor 100 in a space partitioned by the pixel definition layer 180.

The substrate 200 may be a light-transmitting substrate, for example, a glass substrate or a polymer substrate. The polymer substrate may include, for example, polycarbonate, polymethylmethacrylate, polyethyleneterephthalate, polyethylenenaphthalate, polyimide, polyamide, polyamideimide, polyethersulfone, polyorganosiloxane, styrene-ethylene-butylene-styrene copolymer, polyurethane, polyacrylate, polyolefin, or any combination thereof, but is not limited thereto.

A plurality of thin film transistors 280 are formed on the substrate 200. One or more thin film transistor 280 may be included in each subpixel PX, and may include, for example, at least one switching thin film transistor and/or at least one driving thin film transistor. The substrate 200 on which the thin film transistor 280 is formed may be referred to as a thin film transistor substrate (TFT substrate) or a thin film transistor backplane (TFT backplane).

The insulation layer 290 may cover the substrate 200 and the thin film transistor 280 and may be formed on the whole surface of the substrate 200. The insulation layer 290 may be a planarization layer or a passivation layer, and may include an organic insulating material, an inorganic insulating material, an organic-inorganic insulating material, or any combination thereof. The insulation layer 290 may have a plurality of contact holes 241 for electrically connecting the first, second, and third light emitting elements 410, 420, and 430 and the thin film transistor 280 and a plurality of contact holes 242 for electrically connecting the sensor 100 and the thin film transistor 280.

The pixel definition layer 180 may also be formed on the whole surface of the substrate 200 and may be disposed between adjacent subpixels PX's to partition each subpixel PX. The pixel definition layer 180 may have a plurality of openings 181 in each subpixel PX, and in each opening 181, any one of first, second, or third light emitting elements 410, 420, or 430 and the sensor 100 may be disposed.

The first, second and third light emitting elements 410, 420, and 430 are formed on the substrate 200 (or thin film transistor substrate), and are repeatedly arranged along the in-plane direction (e.g., xy direction) of the substrate 200. As described above, the first, second, and third light emitting elements 410, 420, and 430 may be included in the first subpixel PX1, the second subpixel PX2, and the third subpixel PX3, respectively. The first, second, and third light emitting elements 410, 420, and 430 may be electrically connected to separate thin film transistors 280 and may be driven independently.

The first, second and third light emitting elements 410, 420, and 430 may be configured to each independently emit light of a red wavelength spectrum, a green wavelength spectrum, a blue wavelength spectrum, or any combination thereof.

For example, the first light emitting element 410 may be configured to emit light of a red wavelength spectrum, the second light emitting element 420 may be configured to emit light of a green wavelength spectrum, and the third light emitting element 430 may be configured to emit light of a blue wavelength spectrum. Herein, the red wavelength spectrum, the green wavelength spectrum, and the blue wavelength spectrum may have a maximum emission wavelength ($\lambda_{max}$) in a wavelength region of greater than about 600 nm and less than about 750 nm, about 500 nm to about 600 nm, and greater than or equal to about 400 nm and less than about 500 nm, respectively.

The first, second, and third light emitting elements 410, 420, 430 may be, for example, light emitting diodes, for example, an organic light emitting diode including an organic material, an inorganic light emitting diode including an inorganic material, a quantum dot light emitting diode including quantum dots, or a perovskite light emitting diode including perovskite.

The sensor 100 may be formed on the substrate 200 (or the thin film transistor substrate), and may be randomly or regularly arranged along the in-plane direction (e.g., xy direction) of the substrate 200. As described above, the sensor 100 may be disposed in the non-display area NDA, and may be connected to a separate thin film transistor 280 to be independently driven. The sensor 100 may be configured to absorb light of the same wavelength spectrum as the light emitted from at least one of the first, second, or third light emitting elements 410, 420, and 430 to convert it into an electrical signal. For example, the sensor 100 may be configured to absorb light of a red wavelength spectrum, a green wavelength spectrum, a blue wavelength spectrum, or any combination thereof to convert it into an electrical signal. The sensor 100 may be, for example, a photoelectric conversion diode and may be, for example, an organic photoelectric conversion diode including an organic material.

Each of the first, second, and third light emitting elements 410, 420, and 430 and the sensor 100 may include pixel electrodes 411, 421, 431, and 110; a common electrode 120 facing the pixel electrodes 411, 421, 431, and 110 and to which a common voltage is applied; and light emitting layers 412, 422, and 432 or a photoelectric conversion layer 130, a first common auxiliary layer 140, and a second common auxiliary layer 150 between the pixel electrodes 411, 421, 431, and 110 and the common electrode 120. The pixel electrode 110 of the sensor 100 may correspond to the first electrode 110 of the aforementioned sensor 100, the common electrode 120 of the sensor 100 may correspond to the second electrode 120 of the aforementioned sensor 100, and the first and second common auxiliary layers 140 and 150 may correspond to the first and second auxiliary layers 140 and 150 of the aforementioned sensor 100.

The first, second, and third light emitting elements 410, 420, and 430 and the sensor 100 may be arranged in parallel along the in-plane direction (e.g., xy direction) of the substrate 200, and the common electrode 120, the first common auxiliary layer 140, and the second common auxiliary layer 150 which are formed on the whole surface may be shared. For example, as shown in at least FIG. 10, the photoelectric conversion layer 130 of the sensor 100 and the light emitting layers 412, 422, and 432 of the first, second, and third light emitting elements 410, 420, and 430 may at least partially overlap with each other (e.g., partially or completely overlap each other) in the in-plane direction (e.g., xy direction) of the substrate 200, which may be understood to be a horizontal direction that extends in parallel to an in-plane direction of the substrate 200 as shown in FIG. 10 and/or a horizontal direction that extends in parallel to an upper surface of the substrate 200 as shown in FIG. 10, and the photoelectric conversion layer 130 and the light emitting layers 412, 422, and 432 may be at least partially positioned on the same plane (e.g., an xy plane extending in the xy directions that intersects each of the photoelectric conversion layer 130 and the light emitting layers 412, 422, and 432).

The common electrode 120 is continuously formed as a single piece of material that extends on the light emitting layers 412, 422, and 432 and the photoelectric conversion layer 130, and is substantially formed on the whole surface of the substrate 200. The common electrode 120 may apply a common voltage to the first, second, and third light emitting elements 410, 420, and 430 and the sensor 100.

The first common auxiliary layer 140 is between the pixel electrodes 411, 421, 431, and 110 and the light emitting layers 412, 422, 432, and the photoelectric conversion layer 130, and may be continuously formed as a single piece of material that extends on the pixel electrodes 411, 421, 431, and 110, and under the light emitting layers 412, 422, and 432 and the photoelectric conversion layer 130.

The first common auxiliary layer 140 may be a charge auxiliary layer (e.g., hole auxiliary layer) that facilitates injection and/or movement of charge carriers (e.g., holes) from the pixel electrodes 411, 421, and 431 to the light emitting layers 412, 422, and 432.

For example, the HOMO energy level of the first common auxiliary layer 140 may be between the HOMO energy level of the light emitting layers 412, 422, and 432 and the work function of the pixel electrodes 411, 421, 431. The work function of the pixel electrodes 411, 421, and 431, the HOMO energy level of the first common auxiliary layer 140, and the HOMO energy level of the light emitting layers 412, 422, and 432 may be sequentially deepened. On the other hand, the LUMO energy level of the first common auxiliary layer 140 may be shallower than the LUMO energy level of the photoelectric conversion layer 130 and the work function of the pixel electrode 110, respectively.

The first common auxiliary layer 140 may include an organic material, an inorganic material, an organic-inorganic material, or any combination thereof satisfying the HOMO energy level, for example a phthalocyanine compound such as copper phthalocyanine; DNTPD (N,N'-diphenyl-N,N'-bis-[4-(phenyl-m-tolyl-amino)-phenyl]-biphenyl-4,4'-diamine), m-MTDATA (4,4',4"-[tris(3-methylphenyl)phenylamino] triphenylamine), TDATA (4,4'4"-tris(N-diphenylamino)triphenylamine), 2-TNATA (4,4',4"-tris{N,N-(2-naphthyl)-N-phenylamino}-triphenylamine), PEDOT/PSS (poly(3,4-ethylenedioxythiophene)/poly(4-styrenesulfonate)), PANI/DBSA (polyaniline/dodecylbenzenesulfonic acid), PANI/CSA (polyaniline/Camphor sulfonic acid), PANI/PSS (polyaniline/poly(4-styrenesulfonate)), NPB (N,N'-di(naphthalene-l-yl)-N,N'-diphenylbenzidine), polyetherketone including triphenylamine (TPAPEK), 4-isopropyl-4'-methyldiphenyliodonium[tetrakis(pentafluorophenyl)borate], HAT-CN (dipyrazino[2,3-f: 2',3'-h] quinoxaline-2,3,6,7,10,11-hexacarbonitrile), a carbazole-based derivative such as N-phenylcarbazole, polyvinylcarbazole, and the like, a fluorene-based derivative, TPD (N,N'-bis(3-methylphenyl)-N,N'-diphenyl-[1,1-biphenyl]-4,4'-diamine), a triphenylamine-based derivative such as TCTA (4,4',4"-tris(N-carbazolyl)triphenylamine), NPB (N,N'-di(naphthalene-1-yl)-N,N'-diphenylbenzidine), TAPC (4,4'-cyclohexylidene bis[N,N-bis(4-methylphenyl)benzenamine]), HMTPD (4,4'-bis[N,N'-(3-tolyl)amino]-3,3'-dimethylbiphenyl), mCP (1,3-bis(N-carbazolyl)benzene), or any combination thereof, but is not limited thereto. The first common auxiliary layer 140 may be one layer or two or more layers.

The second common auxiliary layer 150 may be between the light emitting layers 412, 422, and 432 and the photoelectric conversion layer 130, and the common electrode 120. The second common auxiliary layer 150 may be continuously formed as a single piece of material that extends on the light emitting layers 412, 422, and 432, and the photoelectric conversion layer 130, and under the common electrode 120.

The second common auxiliary layer 150 may be a charge auxiliary layer (e.g., an electron auxiliary layer) that facilitates injection and/or movement of charge carriers (e.g., electrons) from the common electrode 120 to the light emitting layers 412, 422, and 432. For example, the LUMO energy level of the second common auxiliary layer 150 may be located between the LUMO energy level of the light emitting layers 412, 422, and 432 and the work function of the common electrode 120. The work function of the common electrode 120, the LUMO energy level of the second common auxiliary layer 150, and the LUMO energy level of the light emitting layers 412, 422, and 432 may become shallow in sequence.

The second common auxiliary layer 150 may include an organic material, an inorganic material, an organic-inorganic material, or any combination thereof satisfying the LUMO energy level, for example a halogenated metal such as LiF, NaCl, CsF, RbCl, and RbI; a lanthanides metal such as Yb; a metal oxide such as $Li_2O$ or BaO; Liq (lithium quinolate), Alq3 (tris(8-hydroxyquinolinato)aluminum), 1,3,5-tri[(3-pyridyl)-phen-3-yl]benzene, 2,4,6-tris (3'-(pyridin-3-yl)biphenyl-3-yl)-1,3,5-triazine, 2-(4-(N-phenylbenzimidazol-1-ylphenyl)-9,10-dinaphthylanthracene, TPBi (1,3,5-tri(1-phenyl-1H-benzo[d]imidazol-2-yl)phenyl), BCP (2,9-dimethyl-4,7-diphenyl-1,10-phenanthroline), Bphen (4,7-diphenyl-1,10-phenanthroline), TAZ (3-(4-biphenylyl)-4-phenyl-5-tertbutylphenyl-1,2,4-triazole), NTAZ (4-(naphthalen-1-yl)-3,5-diphenyl-4H-1,2,4-triazole), tBu-PBD (2-(4-biphenylyl)-5-(4-tert-butylphenyl)-1,3,4-oxadiazole), BAlq (bis(2-methyl-8-quinolinolato-N1,08)-(1,1'-biphenyl-4-olato)aluminum), $Bebq_2$ (berylliumbis(benzoquinolin-10-olate), ADN (9,10-di(naphthalene-2-yl) anthracene), BmPyPhB (1,3-bis[3,5-di(pyridin-3-yl)phenyl] benzene), or any combination thereof, but is not limited thereto. The first common auxiliary layer 140 may be one layer or two or more layers.

Each of the first, second, and third light emitting elements 410, 420, and 430 and the sensor 100 may include pixel electrodes 411, 421, 431, and 110 facing the common electrode 120. One of the pixel electrodes 411, 421, 431, and 110 and the common electrode 120 is an anode and the other is a cathode. For example, the pixel electrodes 411, 421, 431, and 110 may be an anode and the common electrode 120 may be a cathode. The pixel electrodes 411, 421, 431, and 110 are separated for each subpixel PX, and may be electrically connected to a separate thin film transistor 280 to be independently driven.

The pixel electrodes 411, 421, 431, and 110 and the common electrode 120 may each be a light-transmitting electrode or a reflective electrode, and for example, at least one of the pixel electrodes 411, 421, 431, and 110 or the common electrode 120 may be a light-transmitting electrode.

For example, when the pixel electrodes 411, 421, 431, and 110 are light-transmitting electrodes and the common electrode 120 is a reflective electrode, the sensor-embedded display panel 1000 may be a bottom emission type display panel configured to emit light toward the substrate 200. For example, when the pixel electrodes 411, 421, 431, and 110 are reflective electrodes and the common electrode 120 are light-transmitting electrode, the sensor-embedded display panel 1000 may be a top emission type display panel configured to emit light toward the opposite side of the substrate 200. For example, when the pixel electrodes 411, 421, 431, and 110 and the common electrode 120 are light-transmitting electrodes, respectively, the sensor-embedded display panel 1000 may be a both side emission type display panel configured to emit light toward both the substrate 200 and the opposite side of the substrate 200.

For example, the pixel electrodes 411, 421, 431, and 110 may be reflective electrodes and the common electrode 120 may be a semi-transmissive electrode. In this case, the sensor-embedded display panel 1000 may have a microcavity structure. In the microcavity structure, reflection may occur repeatedly between the reflective electrode and the semi-transmissive electrode separated by a particular (or, alternatively, predetermined) optical length (e.g., a distance between the semi-transmissive electrode and the reflective electrode) and light of a particular (or, alternatively, predetermined) wavelength spectrum may be enhanced to improve optical properties.

For example, among the light emitted from the light emitting layers 412, 422, and 432 of the first, second, and third light emitting elements 410, 420, and 430, light of a particular (or, alternatively, predetermined) wavelength spectrum may be repeatedly reflected between the semi-transmissive electrode and the reflective electrode and then may be modified. Among the modified light, light of a wavelength spectrum corresponding to a resonance wavelength of a microcavity may be enhanced to exhibit amplified light emission characteristics in a narrow wavelength region. Accordingly, the sensor-embedded display panel 1000 may express colors with high color purity.

For example, among the light incident on the sensor 100, light of a particular (or, alternatively, predetermined) wavelength spectrum may be repeatedly reflected between the semi-transmissive electrode and the reflective electrode to be modified. Among the modified light, light having a wavelength spectrum corresponding to the resonance wavelength of a microcavity may be enhanced to exhibit photoelectric conversion characteristics amplified in a narrow wavelength region. Accordingly, the sensor 100 may exhibit high photoelectric conversion characteristics in a narrow wavelength region.

Each of the first, second, and third light emitting elements 410, 420, and 430 includes light emitting layers 412, 422, and 432 between the pixel electrodes 411, 421, and 431 and the common electrode 120. Each of the light emitting layer 412 included in the first light emitting element 410, the light emitting layer 422 included in the second light emitting element 420, and the light emitting layer 432 included in the third light emitting element 430 may be configured to emit light in the same or different wavelength spectra and may be configured to emit light in, for example a red wavelength spectrum, a green wavelength spectrum, a blue wavelength spectrum, or any combination thereof.

For example, when the first light emitting element 410, the second light emitting element 420, and the third light emitting element 430 are a red light emitting elements, a green light emitting element, and a blue light emitting element, respectively, the light emitting layer 412 included in the first light emitting element 410 may be a red light emitting layer configured to emit light in a red wavelength spectrum, the light emitting layer 422 included in the second light emitting element 420 may be a green light emitting layer configured to emit light in a green wavelength spectrum, and the light emitting layer 432 included in the third light emitting element 430 may be a blue light emitting layer configured to emit light in a blue wavelength spectrum. Herein, the red wavelength spectrum, the green wavelength spectrum, and the blue wavelength spectrum may have a maximum emission wavelength in a wavelength region of greater than about 600 nm and less than about 750 nm, about 500 nm to about 600 nm, and greater than or equal to about 400 nm and less than about 500 nm, respectively.

For example, when at least one of the first light emitting element 410, the second light emitting element 420, or the third light emitting element 430 is a white light emitting element, the light emitting layer of the white light emitting element may be configured to emit light of a full visible light wavelength spectrum, for example, light in a wavelength spectrum of greater than or equal to about 380 nm and less than about 750 nm, about 400 nm to about 700 nm, or about 420 nm to about 700 nm.

The light emitting layers 412, 422, and 432 may include an organic light emitter, a quantum dot, a perovskite, or any combination thereof as a light emitter. For example, the light emitting layers 412, 422, and 432 may include an organic light emitter, and may include at least one host material and a fluorescent or phosphorescent dopant.

The organic light emitter may be, for example, perylene; rubrene; 4-(dicyanomethylene)-2-methyl-6-[p-(dimethylamino)styryl]-4H-pyran; coumarin or a derivative thereof; carbazole or a derivative thereof; TPBi (2,2',2"-(1,3,5-benzenetriyl)-tris(1-phenyl-1-H-benzimidazole); TBADN (2-t-butyl-9,10-di(naphth-2-yl)anthracene); AND (9,10-di(naphthalene-2-yl)anthracene); CBP (4,4'-bis(N-carbazolyl)-1,1'-biphenyl); TCTA (4,4',4"-tris(carbazol-9-yl)-triphenylamine); TPBi (1,3,5-tris(N-phenylbenzimidazole-2-yl)benzene); TBADN (3-tert-butyl-9,10-di(naphth-2-yl) anthracene); DSA (distyrylarylene); CDBP (4,4"-dimethyl-biphenyl); MADN (2-methyl-9,10-bis(naphthalen-2-yl) anthracene); TCP (1,3,5-tris(carbazol-9-yl)benzene); Alq3 (tris(8-hydroxyquinolino)lithium); an organometallic compound including Pt, Os, Ti, Zr, Hf, Eu, Tb, Tm, Rh, Ru, Re, Be, Mg, Al, Ca, Mn, Co, Cu, Zn, Ga, Ge, Pd, Ag, and/or Au, a derivative thereof or any combination thereof, but is not limited thereto.

The quantum dot may include, for example, a Group II-VI semiconductor compound, a Group III-V semiconductor compound, a Group IV-VI semiconductor compound, a Group IV semiconductor element or compound, a Group I-III-VI semiconductor compound, a Group I-II-IV-VI semiconductor compound, a Group II-III-V semiconductor compound, or any combination thereof. The Group II-IV semiconductor compound may be, for example, selected from a binary element semiconductor compound selected from CdSe, CdTe, ZnS, ZnSe, ZnTe, ZnO, HgS, HgSe, HgTe, MgSe, MgS, or a mixture thereof; a ternary element semiconductor compound selected from CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, or a mixture thereof; and a quaternary element semiconductor compound selected from HgZnTeS, CdZnSeS, CdZnSeTe, CdZnSTe, CdHgSeS, CdHgSeTe, CdHgSTe, HgZnSeS, HgZnSeTe, HgZnSTe, or a mixture thereof, but is not limited thereto. The Group III-V semiconductor compound may be, for example, selected from a binary element semiconductor compound selected from GaN, GaP, GaAs, GaSb, AlN, AlP, AlAs, AlSb, InN, InP, InAs, InSb, or a mixture thereof; a ternary element semiconductor compound selected from GaNP, GaNAs, GaNSb, GaPAs, GaPSb, AlNP, AlNAs, AlNSb, AlPAs, AlPSb, InNP, InNAs, InNSb, InPAs, InPSb, or a mixture thereof; and a quaternary element semiconductor compound selected from GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, or a mixture thereof, but is not limited thereto. The Group IV-VI semiconductor compound may be, for example, selected from a binary element semiconductor compound selected from SnS, SnSe, SnTe, PbS, PbSe, PbTe, or a mixture thereof; a ternary element semiconductor compound selected from SnSeS, SnSeTe, SnSTe, PbSeS, PbSeTe, PbSTe, SnPbS, SnPbSe, SnPbTe, or a mixture thereof; and a quaternary element semiconductor compound selected from SnPbSSe, SnPbSeTe, SnPbSTe, or a mixture thereof, but is not limited thereto.

The Group IV semiconductor element or compound may be, for example, selected from a single-element semiconductor such as Si, Ge, or a mixture thereof; and a binary element compound selected from SiC, SiGe, or a mixture thereof, but is not limited thereto. The Group I-III-VI semiconductor compound may be, for example, $CuInSe_2$, $CuInS_2$, CuInGaSe, CuInGaS, or a mixture thereof, but is not limited thereto. The Group I-II-IV-VI semiconductor compound may be, for example, CuZnSnSe, CuZnSnS, or a mixture thereof, but is not limited thereto. The Group II-III-V semiconductor compound may be, for example, InZnP, but is not limited thereto.

The perovskite may be $CH_3NH_3PbBr_3$, $CH_3NH_3PbI_3$, $CH_3NH_3SnBr_3$, $CH_3NH_3SnI_3$, $CH_3NH_3Sn_{1x}Pb_xBr_3$, $CH_3NH_3Sn_{1x}Pb_xI_3$ ($0<x<1$), $HC(NH_2)_2PbI_3$, $HC(NH_2)_2SnI_3$, $(C4H_9NH_3)_2PbBr_4$, $(C6H_5CH_2NH_3)_2PbBr_4$, $(C6H_5CH_2NH_3)_2PbI_4$, $(C6H_5C2H_4NH_3)_2PbBr_4$, $(C6H_{13}NH_3)_2(CH_3NH_3)_{n-1}Pbnl_{3n+1}$ (n is an integer), any combination thereof, but is not limited thereto.

The sensor 100 includes a photoelectric conversion layer 130 between the pixel electrode 110 and the common electrode 120. The photoelectric conversion layer 130 is in parallel with the light emitting layers 412, 422, and 432 of the first, second, and third light emitting elements 410, 420, and 430 along the in-plane direction (e.g., xy direction) of the substrate 200. The photoelectric conversion layer 130 and the light emitting layers 412, 422, and 432 may be disposed on the same plane.

The photoelectric conversion layer 130 may be configured to absorb light of a particular (or, alternatively, predetermined) wavelength spectrum and convert the absorbed light into an electrical signal. The photoelectric conversion layer 130 may be configured to absorb light emitted from at least one of the first, second, or third light emitting elements 410, 420, and 430 and then reflected by the recognition target 40, and convert the absorbed light into an electrical signal. The photoelectric conversion layer 130 may be configured to absorb light of a red wavelength spectrum, a green wavelength spectrum, a blue wavelength spectrum, an infrared wavelength spectrum, or any combination thereof.

For example, the photoelectric conversion layer 130 may be configured to selectively absorb light of a red wavelength spectrum having a maximum absorption wavelength belonging to greater than about 600 nm and less than about 750 nm, and may be configured to absorb light generated from the red light emitting element among the first, second, and third light emitting elements 410, 420, and 430 and then reflected by the recognition target 40.

For example, the photoelectric conversion layer 130 may be configured to selectively absorb light of a green wavelength spectrum having a maximum absorption wavelength belonging to about 500 nm to about 600 nm, and may be configured to absorb light generated from the green light emitting element among the first, second, and third light emitting elements 410, 420, and 430 and then reflected by the recognition target 40.

For example, the photoelectric conversion layer 130 may be configured to selectively absorb light in a blue wavelength spectrum having a maximum absorption wavelength belonging to greater than or equal to about 380 nm and less than about 500 nm, and may be configured to absorb light generated from the blue light emitting element among the first, second, and third light emitting elements 410, 420, and 430 and then reflected by the recognition target 40.

For example, the photoelectric conversion layer 130 may be configured to absorb light of a red wavelength spectrum, a green wavelength spectrum, and a blue wavelength spectrum, that is, light of a full visible wavelength spectrum of greater than or equal to about 380 nm and less than about 750 nm. The photoelectric conversion layer 130 may be configured to absorb light generated from the first, second, and third light emitting elements 410, 420, and 430 and then reflected by the recognition target 40.

A detailed description of the photoelectric conversion layer 130 is the same as described above.

The thickness of the light emitting layers 412, 422, and 432 and the thickness of the photoelectric conversion layer 130 may each independently be about 5 nm to about 300 nm, and within the above range, about 10 nm to about 250 nm, about 20 nm to about 200 nm, or about 30 nm to about 180 nm. A difference in thickness between the light emitting layers 412, 422, and 432 and the photoelectric conversion layer 130 may be less than or equal to about 20 nm, and within the above range, less than or equal to about 15 nm, less than or equal to about 10 nm, or less than or equal to about 5 nm, and the light emitting layers 412, 422, and 432 and the photoelectric conversion layer 130 may have substantially the same thickness.

As described above, the sensor 100 further includes a buffer layer 160. The buffer layer 160 may be between the pixel electrode 110 and the common electrode 120, for example, between the photoelectric conversion layer 130 and the first common auxiliary layer 140. For example, the buffer layer 160 may be in contact with the photoelectric conversion layer 130. For example, one surface of the buffer layer 160 may be in contact with the photoelectric conversion layer 130, and the other surface of the buffer layer 160 may be in contact with the first common auxiliary layer 140.

The buffer layer 160 may include the aforementioned compound represented by Chemical Formula 1, and may compensate for electrical mismatching between the photoelectric conversion layer 130 and the first common auxiliary layer 140 by electrical characteristics of the aforementioned compound represented by Chemical Formula 1.

As described above, the first common auxiliary layer 140 has electrical characteristics of facilitating injection and/or movement of charge carriers (e.g., holes) from the pixel electrodes 411, 421, and 431 to the light emitting layers 412, 422, and 432 of the first, second, and third light emitting elements 410, 420, and 430, but the electrical characteristics of the first common auxiliary layer 140 may be equally applied between the photoelectric conversion layer 130 and the pixel electrode 110 of the sensor 100.

In other words, since the charge carriers (e.g., holes) moving direction in the sensor 100 may be different from that in the first, second, and third light emitting elements 410, 420, and 430, and the electrical characteristics of the photoelectric conversion layer 130 may be different from that of the light emitting layers 412, 422, and 432, unlike the first common auxiliary layer 140 facilitating the injection and/or movement of charge carriers (e.g., holes) from the pixel electrodes 411, 421, and 431 to the light emitting layers 412, 422, and 432 in the first, second, and third light emitting element 410, 420, and 430, the first common auxiliary layer 140 between the photoelectric conversion layer 130 and the pixel electrode 110 in the sensor 100 may work as a barrier preventing movement and/or extraction of the charge carriers (e.g., holes) from the photoelectric conversion layer 130 to the pixel electrode 110, and resultantly deteriorate the electrical characteristics of the sensor 100.

The buffer layer 160 is between the photoelectric conversion layer 130 and the first common auxiliary layer 140, and thus may compensate for electrical mismatching between the photoelectric conversion layer 130 and the first common auxiliary layer 140, so that the charge carriers (e.g., holes) generated in the photoelectric conversion layer 130 may pass through the buffer layer 160 and the first common auxiliary layer 140 and be effectively transferred and/or extracted to the pixel electrode 110. Accordingly, photoelectric conversion efficiency of the sensor 100 may be increased to improve electrical performance.

In addition, when a voltage is applied from the outside to drive the sensor 100, the buffer layer 160 may block reverse injection of charge carriers (e.g., electrons) from the pixel electrode 110 to the photoelectric conversion layer 130 due to the electrical characteristics of the aforementioned compound and thus effectively reduce a dark current. Accordingly, the electrical performance may be improved by reducing a leakage current of the sensor 100.

In addition, since the buffer layer 160 may have, as described above, sufficient heat resistance and thus be stably repeatedly deposited, sufficient performance may be maintained without deterioration in the subsequent high temperature process.

An encapsulation layer 380 is formed on the first, second, and third light emitting elements 410, 420, 430, and the sensor 100. The encapsulation layer 380 may include, for example, a glass plate, a metal thin film, an organic layer, an inorganic layer, an organic-inorganic layer, or any combination thereof. The organic film may include, for example, an acrylic resin, a (meth)acrylic resin, polyisoprene, a vinyl resin, an epoxy resin, a urethane resin, a cellulose resin, a perylene resin, or any combination thereof, but is not limited thereto. The inorganic film may include, for example, an oxides, a nitride, and/or an oxynitride, for example silicon oxide, silicon nitride, silicon oxynitride, aluminum oxide, aluminum nitride, aluminum oxynitride, zirconium oxide, zirconium nitride, zirconium oxynitride, titanium oxide, titanium nitride, titanium oxynitride, hafnium oxide, hafnium nitride, hafnium oxynitride, tantalum oxide, tantalum nitride, tantalum oxynitride, lithium fluoride, or any combination thereof, but is not limited thereto. The organic-inorganic film may include, for example, polyorganosiloxane, but is not limited thereto. The encapsulation layer 380 may be one layer or two or more layers.

As described above, the sensor-embedded display panel 1000 according to some example embodiments includes the first, second, and third light emitting elements 410, 420, and 430 configured to emit light of a particular (or, alternatively, predetermined) wavelength spectrum to display colors, and the sensor 100 configured to absorb light generated by reflection of the light, by the recognition target 40 and convert it into an electrical signal, in the same plane on the substrate 200, thereby performing a display function and a recognition function (e.g., biometric recognition function) together. Accordingly, unlike conventional display panels in which the sensor is formed on the outside of the display panel or formed under the display panel by manufacturing the sensor as a separate module, it may improve performance without increasing the thickness, implementing a slim-type high performance sensor-embedded display panel 1000.

In addition, since the sensor 100 uses light emitted from the first, second, and third light emitting elements 410, 420, and 430, the recognition function (e.g., biometric recognition function) may be performed without a separate light source. Therefore, it is not necessary to provide a separate light source outside the display panel, thereby preventing a decrease in the aperture ratio of the display panel due to the area occupied by the light source, and at the same time saving power consumed by the separate light source to improve power consumption.

In addition, as described above, the first, second, and third light emitting elements 410, 420, and 430 and the sensor 100 share the common electrode 120, the first common auxiliary layer 140, and the second common auxiliary layer 150 and thus the structure and process may be simplified compared with the case where the first, second, and third light emitting elements 410, 420, and 430 and the sensor 100 are formed in separate processes.

In addition, as described above, the sensor 100 may be an organic sensor including an organic photoelectric conversion layer, and accordingly, it may have a light absorbance that is two or more times higher than that of an inorganic diode such as a silicon photodiode, performing a high-sensitivity sensing function with further thinner thickness.

In addition, as described above, the sensor 100 may be disposed anywhere in the non-display area NDA, they may be disposed at a desired location of the sensor-embedded display panel 1000 as many as desired. Therefore, for example, by randomly or regularly arranging the sensor 100 over the entire sensor-embedded display panel 1000, the biometric recognition function may be performed on any portion of the screen of an electronic device such as a mobile device and the biometric recognition function may be selectively performed only in a specific location where the biometric recognition function is required.

In addition, as described above, the sensor 100 is disposed between the first common auxiliary layer 140 and the photoelectric conversion layer 130 and includes the buffer layer 160 including the aforementioned compound and may compensate electrical mismatching between the first common auxiliary layer 140 and the photoelectric conversion layer 130 and thus improve photoelectric conversion efficiency and simultaneously prevent reverse injection of charge carriers (e.g., electrons) from the pixel electrode 110 to the photoelectric conversion layer 130 when an external voltage is applied thereto, effectively improving a dark current. Accordingly, in a sensor-embedded display panel 1000, the electrical performance of the sensor 100 may be improved.

Hereinafter, another example of the sensor-embedded display panel 1000 according to some example embodiments is described.

Figure 11:
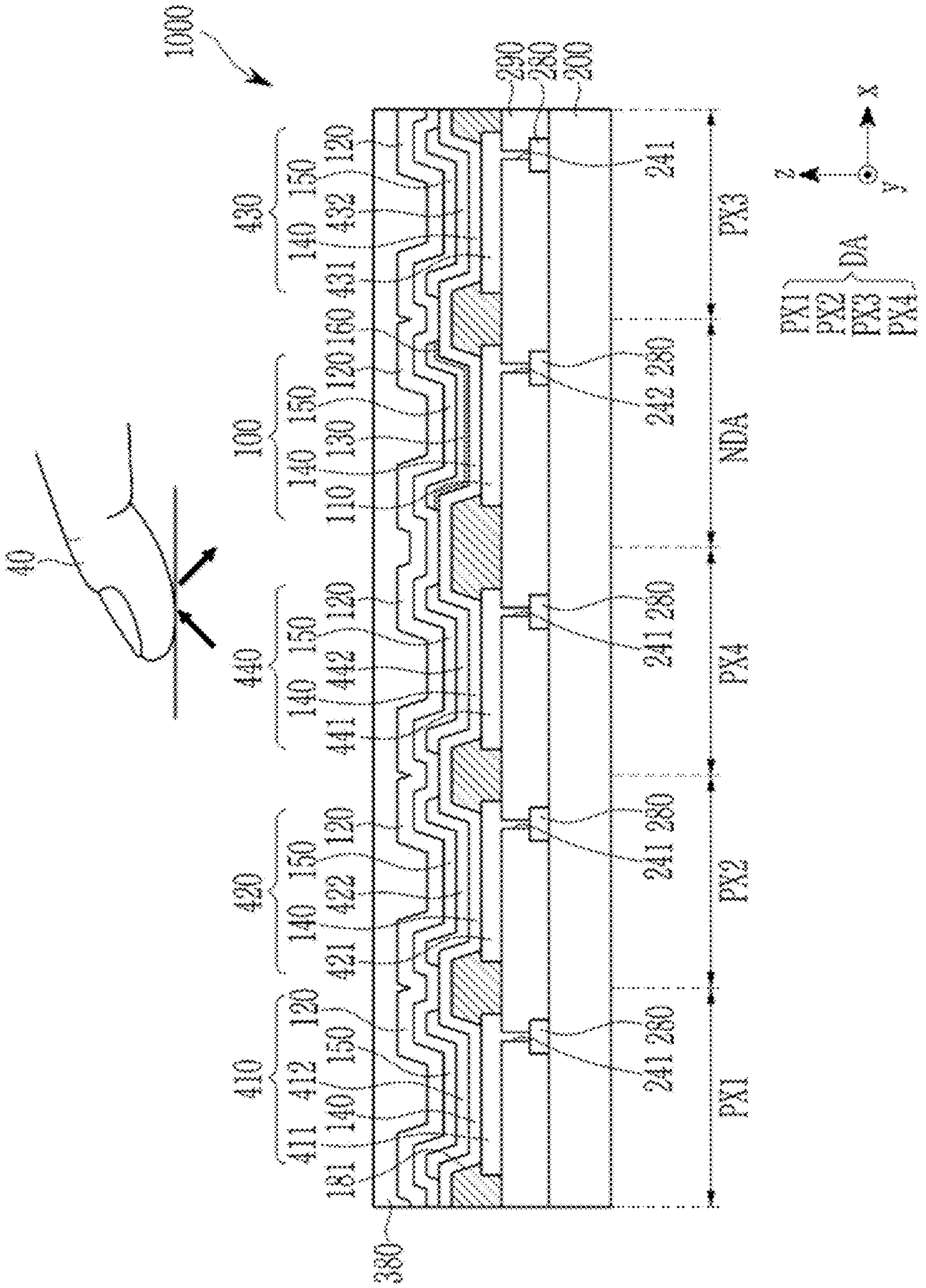
FIG. 11 is a cross-sectional view illustrating another example of a sensor-embedded display panel according to some example embodiments.

FIG. 11 is a cross-sectional view illustrating another example of a sensor-embedded display panel according to some example embodiments.

Referring to FIG. 11, a sensor-embedded display panel 1000 according to some example embodiments includes a plurality of subpixels PX configured to display different colors, that is, a first subpixel PX1, a second subpixel PX2, and a third subpixel PX3 configured to display a first color, a second color, or a third color selected from red, green, and blue, and the first subpixel PX1, the second subpixel PX2, and the third subpixel PX3 include a first light emitting element 410, a second light emitting element 420, and a third light emitting element 430, respectively, like some example embodiments, including the example embodiments shown in FIGS. 9 and 10.

However, unlike some example embodiments, including the example embodiments shown in FIGS. 9 and 10, the sensor-embedded display panel 1000 according to some example embodiments may include the fourth light emitting element 440 configured to emit light in an infrared wavelength spectrum. For example, the fourth light emitting element 440 may be included in the fourth subpixel PX4 adjacent to the first subpixel PX1, the second subpixel PX2, and/or the third subpixel PX3, or may be included in a non-display area, NDA. The fourth subpixel PX4 may form one unit pixel UP together with the first subpixel PX1, the second subpixel PX2, and the third subpixel PX3, and the unit pixel UP may be arranged repeatedly along rows and/or columns.

Descriptions of the first subpixel PX1, the second subpixel PX2, the third subpixel PX3, the first light emitting element 410, the second light emitting element 420, the third light emitting element 430, and the sensor 100 are the same as described above.

The fourth light emitting element 440 is disposed on the substrate 200 and is in parallel with the sensor 100 along the in-plane direction (xy direction) of the substrate 200 together with the first, second, and third light emitting elements 410, 420, and 430, such that the first, second, third, and fourth light emitting elements 410, 420, 430, and 440 and the sensor 100 at least partially overlap in the in-plane direction. The fourth light emitting element 440 may be disposed on the same plane as the first, second, and third light emitting elements 410, 420, and 430 and the sensor 100. The fourth light emitting element 440 may be electrically connected to a separate thin film transistor 280 and driven independently. The fourth light emitting element 440 may have a structure in which the pixel electrode 441, the first common auxiliary layer 140, the light emitting layer 442, the second common auxiliary layer 150, and the common electrode 120 are sequentially stacked. Among them, the common electrode 120, the first common auxiliary layer 140, and the second common auxiliary layer 150 may be shared with the first, second, and third light emitting elements 410, 420, and 430 and the sensor 100. The light emitting layer 442 may be configured to emit light of an infrared wavelength spectrum, which may have for example a maximum emission wavelength in a region of greater than or equal to about 750 nm, about 750 nm to about 20 μm, about 780 nm to about 20 μm, about 800 nm to about 20 μm, about 750 nm to about 15 μm, about 780 nm to about 15 μm, about 800 nm to about 15 μm, about 750 nm to about 10 μm, about 780 nm to about 10 μm, about 800 nm to about 10 μm, about 750 nm to about 5 μm, about 780 nm to about 5 μm, about 800 nm to about 5 μm, about 750 nm to about 3 μm, about 780 nm to about 3 μm, about 800 nm to about 3 μm, about 750 nm to about 2 μm, about 780 nm to about 2 μm, about 800 nm to about 2 μm, about 750 nm to about 1.5 μm, about 780 nm to about 1.5 μm, or about 800 nm to about 1.5 μm.

The sensor 100 may be configured to absorb light generated from at least one of the first, second, third, or fourth light emitting elements 410, 420, 430, and 440 and then reflected by a recognition target 40 such as a living body or a tool, and convert the absorbed light into an electrical signal. For example, the sensor 100 may be configured to absorb light in an infrared wavelength spectrum generated from the fourth light emitting element 440 and then reflected by the recognition target 40, and convert the absorbed light into an electrical signal. In this case, the photoelectric conversion layer 130 of the sensor 100 may include an organic material, an inorganic material, an organic-inorganic material, or any combination thereof configured to selectively absorb light in the infrared wavelength spectrum. For example, the photoelectric conversion layer 130 may include a quantum dot, a quinoid metal complex compound, a polymethine compound, a cyanine compound, a phthalocyanine compound, a merocyanine compound, a naphthalocyanine compound, an immonium compound, a diimmonium compound, a triarylmethane compound, a dipyrromethene compound, an anthraquinone compound, a diquinone compound, a naphthoquinone compound, a squarylium compound, a rylene compound, a perylene compound, a squaraine compound, a pyrylium compound, a squaraine compound, a thiopyrylium compound, a diketopyrrolopyrrole compound, a boron dipyrromethene compound, a nickel-dithiol complex compound, a croconium compound, a derivative thereof, or any combination thereof, but is not limited thereto.

The sensor-embedded display panel 1000 according to some example embodiments includes the fourth light emitting element 440 configured to emit light in the infrared wavelength spectrum and the sensor 100 configured to absorb light in the infrared wavelength spectrum. Therefore, in addition to the biometric detection function, the sensitivity of the sensor 100 may be improved even in a low-illumination environment, and the detection capability of a 3D image may be further increased by widening a dynamic range for detailed division of black and white contrast. Accordingly, the sensing capability of the sensor-embedded display panel 1000 may be further improved. In particular, since light in the infrared wavelength spectrum may have a deeper penetration depth due to its long wavelength characteristics and information located at different depths may be effectively obtained, images or changes in blood vessels such as veins, iris and/or face, etc., in addition to fingerprints may be effectively detected, and the scope of application nay be further expanded.

The aforementioned sensor-embedded display panel 1000 may be applied to (e.g., included in) electronic devices such as various display devices. Electronic devices such as display devices may be applied to, for example, mobile phones, video phones, smart phones, smart pads, smart watches, digital cameras, tablet PCs, laptop PCs, notebook computers, computer monitors, wearable computers, televisions, digital broadcasting terminals, e-books, personal digital assistants (PDAs), portable multimedia player (PMP), enterprise digital assistant (EDA), head mounted display (HMD), vehicle navigation, Internet of Things (loT), Internet of all things (loE), drones, door locks, safes, automatic teller machines (ATM), security devices, medical devices, or automotive electronic components, but are not limited thereto.

Figure 12:
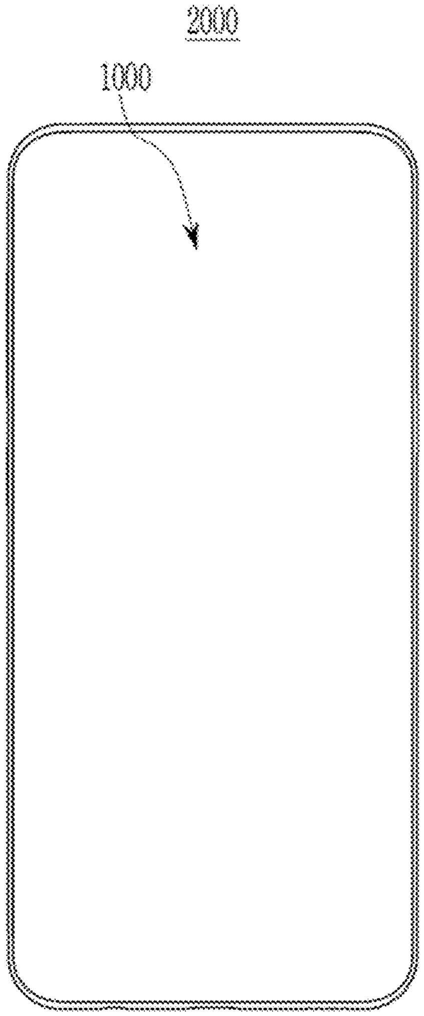
FIG. 12 is a schematic view illustrating an example of a smart phone as an electronic device according to some example embodiments.

FIG. 12 is a schematic view illustrating an example of a smart phone as an electronic device according to some example embodiments.

Referring to FIG. 12, the electronic device 2000 may include the aforementioned sensor-embedded display panel 1000, and the sensor 100 disposed in the whole or a part of the sensor-embedded display panel 1000, and thus a biometric recognition function may be performed on any part of the screen, and according to the user's selection, the biometric recognition function may be selectively performed only at a specific location where the biometric recognition function is required.

An example of a method of recognizing the recognition target 40 in an electronic device 2000 such as a display device may include, for example, driving the first, second, and third light emitting elements 410, 420, and 430 of the sensor-embedded display panel 1000 (or the first, second, third, and fourth light emitting elements 410, 420, 430, and 440) and the sensor 100 to detect the light emitted from the first, second, and third light emitting elements 410, 420, and 430 (or the first, second, third, and fourth light emitting elements 410, 420, 430, and 440) and then reflected by the recognition target 40, in the sensor 100; comparing the image of the recognition target 40 stored in advance with the image of the recognition target 40 detected by the sensor 100; and judging the consistency of the compared images and if they match according to the determination that recognition of the recognition target 40 is complete, turning off the sensor 100, permitting user's access to the display device, and driving the sensor-embedded display panel 1000 to display an image.

Figure 13:
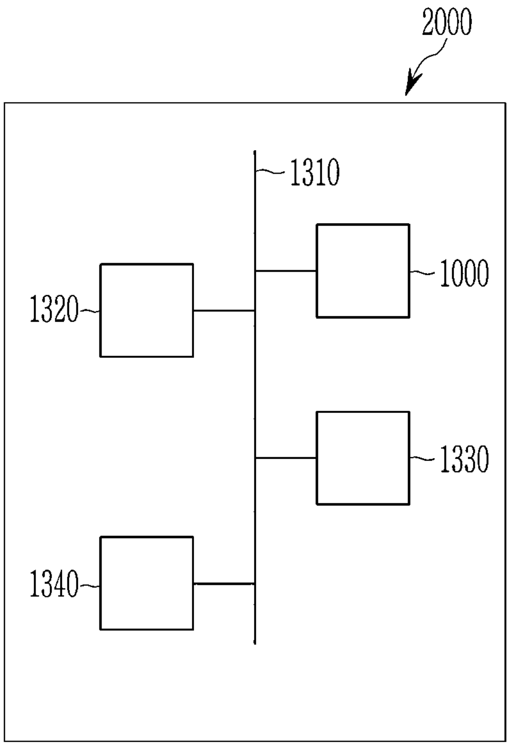
FIG. 13 is a schematic view illustrating an example of a configuration diagram of an electronic device according to some example embodiments.

FIG. 13 is a schematic view illustrating an example of a configuration diagram of an electronic device according to some example embodiments.

Referring to FIG. 13, in addition to the aforementioned constituent elements (e.g., the sensor-embedded display panel 1000), the electronic device 2000 may further include a bus 1310, a processor 1320, a memory 1330, and at least one additional device 1340. Information of the aforementioned sensor-embedded display panel 1000, processor 1320, memory 1330, and at least one additional device 1340 may be transmitted to each other through the bus 1310. In some example embodiments, the at least one additional device 1340 may be omitted. In some example embodiments, the sensor-embedded display panel 1000 may be replaced by a display device including, for example, exclusively light emitting elements and no light absorption sensors, while the at least one additional device 1340 may include one or a plurality (e.g., an array) of sensors according to any of the example embodiments which may serve as a biometric sensor, a camera, or the like.

The processor 1320 may include one or more articles of processing circuitry such as a hardware including logic circuits; a hardware/software combination such as processor-implemented software; or any combination thereof. For example, the processing circuitry may be a central processing unit (CPU), an arithmetic logic unit (ALU), a digital signal processor, a microcomputer, a field programmable gate array (FPGA), System-on-Chip (SoC), a programmable logic unit, a microprocessor, an application-specific integrated circuit (ASIC), and the like. As an example, the processing circuitry may include a non-transitory computer readable storage device. The processor 1320 may control, for example, a display operation of the sensor-embedded display panel 1000 or a sensing operation of the sensor 100.

The memory 1330 may be a non-transitory computer readable storage medium, such as, for example, as a solid state drive (SSD) and may store an instruction program (e.g., program of instructions), and the processor 1320 may perform a function related to the sensor-embedded display panel 1000 by executing the stored instruction program.

The at least one additional device 1340 may include one or more communication interfaces (e.g., wireless communication interfaces, wired interfaces), user interfaces (e.g., keyboard, mouse, buttons, etc.), power supply and/or power supply interfaces, or any combination thereof.

The units and/or modules described herein may be implemented using hardware constituent elements and software constituent elements. The units and/or modules described herein may include, may be included in, and/or may be implemented by one or more articles of processing circuitry such as a hardware including logic circuits; a hardware/software combination such as processor-implemented software; or any combination thereof. For example, the processing circuitry may be a central processing unit (CPU), an arithmetic logic unit (ALU), a digital signal processor, a microcomputer, a field programmable gate array (FPGA), System-on-Chip (SoC), a programmable logic unit, a microprocessor, an application-specific integrated circuit (ASIC), and the like. For example, the hardware constituent elements may include microphones, amplifiers, band pass filters, audio-to-digital converters, and processing devices. The processing device may be implemented using one or more hardware devices configured to perform and/or execute program code by performing arithmetic, logic, and input/output operations. The processing device may include a processor, a controller and an arithmetic logic unit, a digital signal processor, a microcomputer, a field programmable array, a programmable logic unit, a microprocessor, or any other device capable of responding to and executing instructions. The processing device may access, store, operate, process, and generate data in response to execution of an operating system (OS) and one or more software running on the operating system.

The software may include a computer program, a code, an instruction, or any combination thereof, and may transform a processing device for a special purpose by instructing and/or configuring the processing device independently or collectively to operate as desired. The software and data may be implemented permanently or temporarily as signal waves capable of providing or interpreting instructions or data to machines, parts, physical or virtual equipment, computer storage media or devices, or processing devices. The software may also be distributed over networked computer systems so that the software may be stored and executed in a distributed manner. The software and data may be stored by one or more non-transitory computer readable storage devices.

The method according to the foregoing embodiments may be recorded in a non-transitory computer readable storage device including program instructions for implementing various operations of some example embodiments. The storage device may also include program instructions, data files, data structures, and the like alone or in combination. The program instructions recorded in the storage device may be specially designed for some example embodiments or may be known to those skilled in computer software and available for use. Examples of non-transitory computer-readable storage devices may include magnetic media such as hard disks, floppy disks, and magnetic tapes; optical media such as CD-ROM discs, DVDs and/or blue-ray discs; magneto-optical media such as optical disks; and a hardware device configured to store and execute program instructions such as ROM, RAM, flash memory, and the like. The aforementioned device may be configured to operate as one or more software modules to perform the operations of some example embodiments.

Hereinafter, some example embodiments are illustrated in more detail with reference to examples. However, the present scope of the inventive concepts is not limited to these examples.

Synthesis Example: Synthesis of Compound 3

[Compound 3]

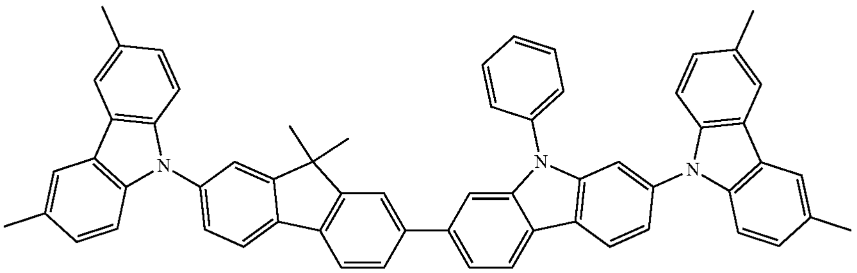

(1) Synthesis of Compound 1

[Reaction Scheme 1]

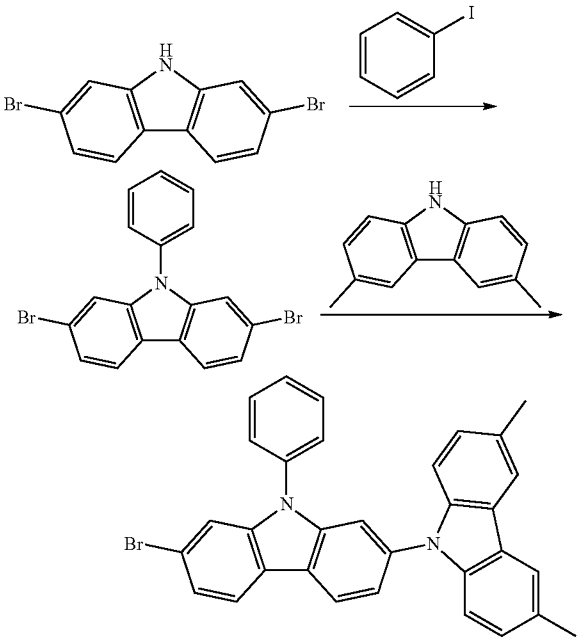

1 i) Synthesis of Intermediate 1

3.08 g (9.47 mmol) of 2,7-dibromo-9H-carbazole and 2.32 g (11.37 mmol) of iodobenzene are dissolved in 50 ml of anhydrous toluene and then, heated under reflux for 8 hours in the presence of 10 mol % of $Pd(dba)_2$ and 20 mol % of $P(t\text{-}Bu)_3$, based on the molar number of 2,7-dibromo-9H-carbazole and 2.73 g (28.42 mmol) of sodium t-butoxide (NaOtBu). After removing the organic solvent, the obtained product is separated and purified through silica gel column chromatography, obtaining 3.27 g of 2,7-dibromo-9-phenyl-9H-carbazole (Intermediate 1). A yield thereof is 86%.

ii) Synthesis of Compound 1

3.27 g (8.15 mmol) of Intermediate 1 and 1.91 g (9.78 mmol) of 3,6-dimethyl-9H-carbazole are dissolved in 50 ml of anhydrous toluene and then, heated under reflux for 8 hours in the presence of 10 mol % of $Pd(dba)_2$ and 20 mol % of $P(t\text{-}Bu)_3$ based on the molar number of Intermediate 1, and 2.35 g (24.44 mmol) of sodium t-butoxide (NaOtBu). After removing the organic solvent, the obtained product is separated and purified through silica gel column chromatography, obtaining 3.53 g of 7-bromo-3',6'-dimethyl-9-phenyl-9H-2,9'-bicarbazole (Compound 1). A yield thereof is 84%.

[Reaction Scheme 2]

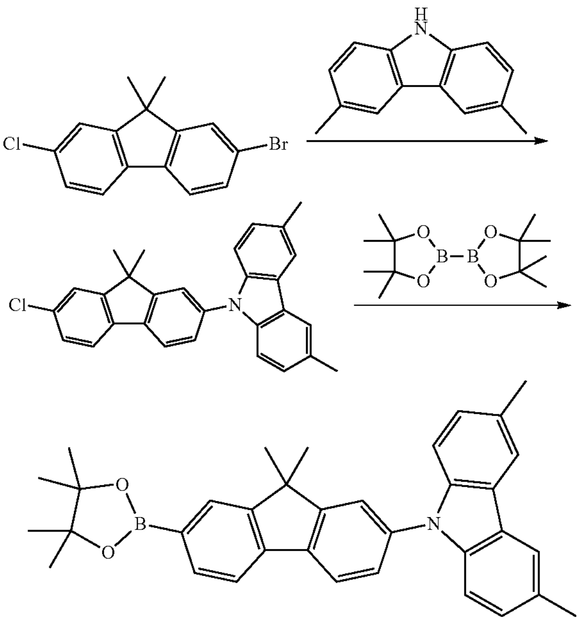

2 i) Synthesis of Intermediate 2

3.28 g (10.66 mmol) of 2-bromo-7-chloro-9,9-dimethyl-9H-fluorene and 2.50 g (12.80 mmol) of 3,6-dimethyl-9H-carbazole are dissolved in 50 ml of anhydrous toluene and then, heated under reflux for 8 hours in the presence of 10 mol % of $Pd(dba)_2$ and 20 mol % of $P(t\text{-}Bu)_3$ based on the molar number of 2-bromo-7-chloro-9,9-dimethyl-9H-fluorene, and 3.08 g (31.99 mmol) of sodium t-butoxide (NaOtBu). After removing the organic solvent, the obtained product is separated and purified through silica gel column chromatography, obtaining 3.98 g of 9-(7-chloro-9,9-dimethyl-9H-fluoren-2-yl)-3,6-dimethyl-9H-carbazole (Intermediate 2). A yield thereof is 88%.

ii) Synthesis of Compound 2

3.12 g (7.40 mmol) of Intermediate 2 and 2.01 g (7.92 mmol) of 4,4,4',4',5,5,5',5'-octamethyl-2,2'-bi(1,3,2-dioxaborolane) are dissolved in 30 ml of dioxane, and then, 2.18 g (22.20 mmol) of potassium acetate is added thereto and then, heated and stirred for 12 hours. When a reaction is completed, the resultant is extracted with methylenechloride (MC) and $H_2O$ and then, separated and purified through silica gel column chromatography, obtaining 3.10 g of 9-(9,9-dimethyl-7-(4,4,5,5-tetramethyl-1,3,2-dioxaborolan-2-yl)-9H-fluoren-2-yl)-3,6-dimethyl-9H-carbazole (Compound 2). A yield thereof is 82%.

(3) Synthesis of Compound 3

[Reaction Scheme 3]

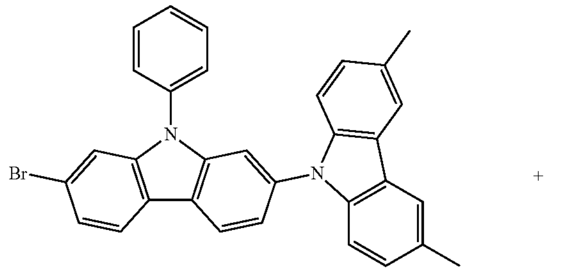

1

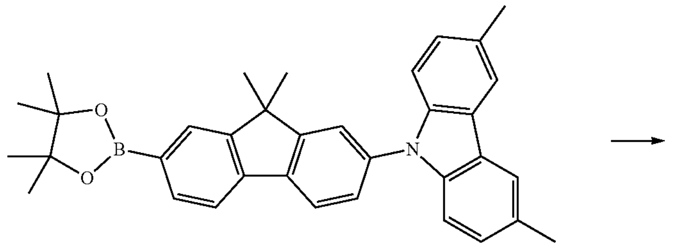

2

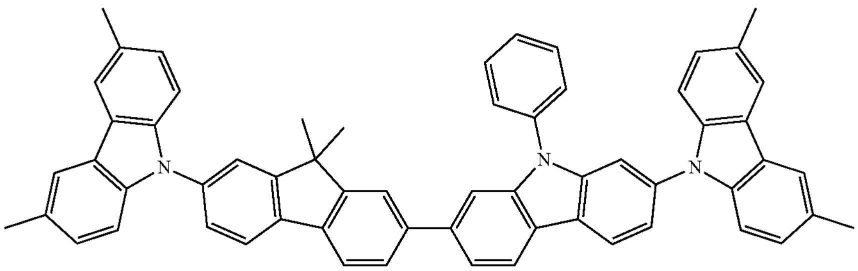

3

2.51 g (4.87 mmol) of Compound 1, 2.50 g (4.87 mmol) of Compound 2, 0.281 g (0.24 mmol) of $Pd(PPh_3)_4$, and 2.02 g (14.6 mmol) of $K_2CO_3$ are dissolved in 50 ml of a $THF/H_2O$ (a volume ratio of 2:1) solvent and then, heated under reflux at 80° C. for 12 hours. Subsequently, a product obtained through extraction with water and ethylether is separated and purified through silica gel column chromatography, obtaining 3.23 g of 7-(7-(3,6-dimethyl-9H-carbazol-9-yl)-9,9-dimethyl-9H-fluoren-2-yl)-3',6'-dimethyl-9-phenyl-9H-2,9'-bicarbazole (Compound 3). A yield thereof is 81%.

1H NMR (500 MHz, CDCl3): δ 8.35 (d, 1H), 8.30 (d, 1H), 7.95-7.91 (m, 4H), 7.85 (d, 1H), 7.76 (s, 1H), 7.71-7.69 (m, 3H), 7.67-7.59 (m, 6H), 7.56-7.53 (m, 2H), 7.50-7.45 (m, 2H), 7.38 (d, 2H), 7.34 (d, 2H), 7.26-7.20 (m, 4H), 2.57 (s, 6H), 2.55 (s, 6H), 1.61 (s, 6H)

Evaluation I

Compound 3 of Synthesis Example is evaluated with respect to an energy level.

HOMO energy level is evaluated by irradiating UV light to a thin film with AC-3 (Riken Keiki Co., LTD.) and measuring an amount of photoelectrons emitted according to energy, while LUMO energy level is evaluated by using the HOMO energy level and an energy bandgap measured with a UV-Vis spectrometer (Shimadzu Corporation).

The results are shown in Table 1.

TABLE 1

| | HOMO (eV) | LUMO (eV) | Eg (eV) |
|---|---|---|---|
| Compound 3 | 5.62 | 2.61 | 3.01 |

* HOMO, LUMO: absolute value
* Eg: energy bandgap

Evaluation II

The compounds according to Synthesis Examples are evaluated with respect to thermal resistance property.

The thermal resistance property is evaluated by measuring a weight loss according to a temperature increase under a high vacuum of less than or equal to 10 Pa, and accordingly, a temperature where an initial weight is reduced respectively by 10 wt % and 50 wt % is each expressed as $Ts_{10}$ and $Ts_{50}$.

A glass transition temperature Tg and a crystallization temperature (Tc) are measured by using a differential scanning calorimeter DSC (Model: Discovery DSC, Manufacturer: TA Instruments).

A melting point Tm is measured under a normal pressure through a differential thermal analysis DTA (Model: TG-DTA2000SE, Manufacturer: NETZSCH).

A single film is evaluated with respect to heat resistance by depositing a compound to be 30 nm thick on a Si wafer and heat-treating it for 3 hours and then, measuring the highest temperature where the single film is no more crystalized, when examined with an optical electron microscope OEM.

The results are shown in Table 2.

TABLE 2

| | Compound 3 |
|---|---|
| Glass transition temperature Tg (° C.) | 200.1 |
| Crystallization temperature Tc (° C.) | 281.4 |
| Melting temperature Tm (° C.) | 298 |
| $T_{s10}$ (° C.) | 342 |
| $T_{s50}$ (° C.) | 372 |
| Heat resistance of single film (° C.) | 200 |

* $T_{s10}$: a temperature at the point where a weight is reduced by 10 wt % compared to the initial weight
* $T_{s50}$: a temperature at the point where a weight is reduced by 50 wt % compared to the initial weight Manufacture of Sensor I Example 1

Al (10 nm), ITO (100 nm), and Al (8 nm) are sequentially deposited on the glass substrate to form a lower electrode (work function: 4.9 eV) having an Al/ITO/Al structure. Subsequently, N,N'-bis(3-methylphenyl)-N,N'-diphenyl-[1,1-biphenyl]-4,4'-diamine is formed on the lower electrode to form a 165 nm-thick hole auxiliary layer (HOMO: 5.3 eV to 5.6 eV, LUMO: 2.0 eV to 2.3 eV). Then, on the hole auxiliary layer, Compound 3 according to Synthesis Example is deposited to form a 5 nm-thick buffer layer (HOMO: 5.62 eV, LUMO: 2.61 eV). On the buffer layer, Compound A (HOMO: 5.60 eV, LUMO: 3.52 eV) is deposited to form a 10 nm-thick p-type semiconductor layer, and fullerene (C60, HOMO: 6.40 eV, LUMO: 4.23 eV) is deposited to form a 5 nm-thick n-type semiconductor layer, forming a bi-layered photoelectric conversion layer. On the photoelectric conversion layer, 4,7-diphenyl-1,10-phenanthroline is deposited to form a 40 nm-thick electron auxiliary layer (HOMO: 6.1-6.4 eV, LUMO: 2.9-3.2 eV). Subsequently, on the electron auxiliary layer, magnesium and silver are deposited to form a 15 nm-thick Mg:Ag upper electrode, and thus manufacturing a sensor.

[Compound A]

Example 2

A sensor is manufactured according to the same method as Example 1 except that a 10 nm-thick buffer layer is formed.

Example 3

A sensor is manufactured according to the same method as Example 1 except that a 30 nm-thick buffer layer is formed.

Comparative Example 1

A sensor is manufactured according to the same method as Example 1 except that the buffer layer is not formed.

Comparative Example 2

A sensor is manufactured according to the same method as Example 1 except that Compound 4 instead of Compound 3 is deposited to form a 5 nm-thick buffer layer.

[Compound 4]

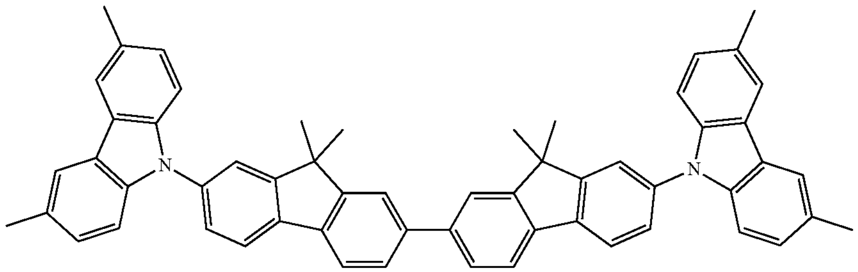

Comparative Example 3

A sensor is manufactured according to the same method as Comparative Example 2 except that Compound 4 is deposited to form a 10 nm-thick buffer layer.

Comparative Example 4

A sensor is manufactured according to the same method as Comparative Example 2 except that Compound 4 is deposited to form a 30 nm-thick buffer layer.

Evaluation III

The sensors according to Examples and Comparative Examples are evaluated with respect to photoelectric conversion efficiency.

The photoelectric conversion efficiency is evaluated from the external quantum efficiency EQE, and the EQE may be evaluated from the EQE at the maximum absorption wavelength $\lambda_{max}$, and is evaluated using Incident Photon to Current Conversion Efficiency (IPCE) method in a wavelength region of 400 nm to 700 nm.

Figure 14:
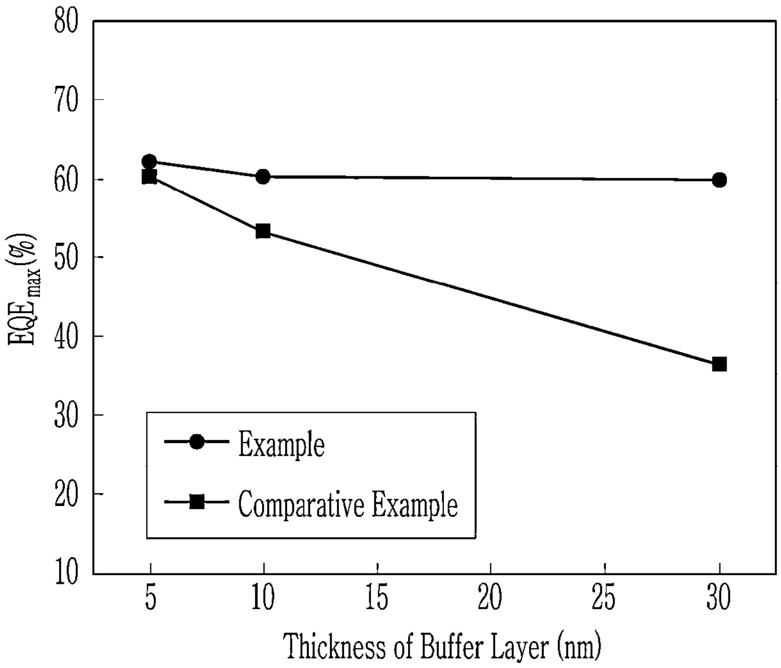
FIG. 14 is a graph showing a change in external quantum efficiency according to a thickness of a buffer layer in sensors according to examples and comparative examples.

The results are shown in Table 3 and FIG. 14.

FIG. 14 is a graph showing a change in external quantum efficiency according to a thickness of a buffer layer in sensors according to Examples and Comparative Examples.

TABLE 3

| | $EQE_{max}$ (%) | ΔEQE (%) |
|---|---|---|
| Example 1 | 62.11 | Ref 1. |
| Example 2 | 60.4 | −2.8 |
| Example 3 | 59.88 | −3.6 |
| Comparative Example 2 | 60.32 | Ref 2. |
| Comparative Example 3 | 53.19 | −11.8 |
| Comparative Example 4 | 36.48 | −40 |

Referring to Table 3 and FIG. 14, the sensors according to Examples exhibit improved photoelectric conversion efficiency, compared with the sensors according to Comparative Examples. Particularly, the sensors according to Examples exhibit small photoelectric conversion efficiency change rates (within about 5%) according to a thickness (5 nm to 30 nm) of a buffer layer, and the sensors according to Comparative Examples exhibit large photoelectric conversion efficiency change rates (about 10 to 40%) according to a thickness (5 nm to 30 nm) of a buffer layer.

Accordingly, the sensors according to Examples have a low dependence on a thickness of the buffer layer, compared with the sensors according to Comparative Examples, and thus exhibit high stability of photoelectric conversion efficiency according to a thickness of the buffer layer.

Evaluation IV

The sensors according to Examples and Comparative Examples are evaluated with respect to a dark current under a reverse bias voltage.

The dark current is evaluated by dark current density obtained by dividing a dark current measured with a current-voltage evaluation equipment (Keithley K4200 parameter analyzer) by a unit pixel area (0.04 $cm^2$), and the dark current density is evaluated from a current, when a reverse bias of −3 V is applied to the sensors.

The results are shown in Table 4.

TABLE 4

| | Dark current ($mA/cm^2$) |
|---|---|
| Example 1 | $1.1 \times 10^{-5}$ |
| Example 2 | $5.5 \times 10^{-6}$ |
| Example 3 | $2.5 \times 10^{-6}$ |
| Comparative Example 1 | $1.8 \times 10^{-5}$ |
| Comparative Example 2 | $8.9 \times 10^{-6}$ |
| Comparative Example 3 | $9.7 \times 10^{-6}$ |
| Comparative Example 4 | $8.3 \times 10^{-6}$ |

Referring to Table 4, the sensors according to Examples exhibit a lower or equivalent dark current when a reverse bias is applied thereto, compared with the sensors according to Comparative Examples.

Manufacture of Sensor II

Example 4

ITO is deposited on a glass substrate to form a 100 nm-thick lower electrode (a work function: 4.9 eV). Subsequently, Compound 3 according to Synthesis Example is deposited on the lower electrode to form a 5 nm-thick buffer layer (HOMO: 5.62 eV, LUMO: 2.61 eV). On the buffer layer, Compound A (p-type semiconductor) and fullerene (C60, n-type semiconductor) are co-deposited in a volume ratio (thickness ratio) of 1:1 to form a 100 nm-thick photoelectric conversion layer. On the photoelectric conversion layer, Yb (a work function: 3 eV) is deposited to form a 2 nm-thick electron auxiliary layer. Subsequently, on the electron auxiliary layer, ITO is deposited to form a 7 nm-thick upper electrode (a work function: 4.7 eV), manufacturing a sensor.

Comparative Example 5

A sensor is manufactured according to the same method as Example 4 except that Compound 4 instead of Compound 3 is deposited to form a 5 nm-thick buffer layer.

Evaluation V

The sensors according to Examples and Comparative Examples are evaluated with respect to thermal resistance property.

The thermal resistance property is evaluated by heat-treating the sensors according to Examples and Comparative Examples up to 210° C. and examining a dark current and a residual charge carrier change according to a temperature increase.

The residual charge carrier characteristics relate to an amount of residual charge carriers, which are charge carriers not photoelectrically converted into signals in one frame but remain and are read in the next frame, and are evaluated by irradiating light in a green wavelength region for particular (or, alternatively, predetermined) time (40 μs) to the devices according to Examples and Comparative Examples and turning it off and then, measuring a current amount by a unit of $10^{-6}$ second with a Keithley 2400 equipment. An amount of residual electrons is evaluated at 5000 lux by a unit of $h+/\mu m^2$.

The results are shown in Tables 5 and 6.

TABLE 5

| | D.C (pristine) ($h/s/\mu m^2$) | D.C 200° C. ($h/s/\mu m^2$) | D.C 210° C. ($h/s/\mu m^2$) |
|---|---|---|---|
| Example 4 | 26 | 2 | 367 |
| Comparative Example 5 | 42 | 89 | 3662 |

* D.C: dark current

TABLE 6

| | R.C (pristine) ($h+/\mu m^2$) | R.C 180° C. ($h+/\mu m^2$) | R.C 210° C. ($h+/\mu m^2$) |
|---|---|---|---|
| Example 4 | 30 | 18 | 25 |
| Comparative Example 5 | 22 | 26 | 48 |

* R.C: remaining charge carriers (remaining electrons)

Referring to Tables 5 and 6, the sensors according to Examples exhibit small changes in terms of the dark current and the residual charge carriers according to a temperature increase and thus relatively high heat resistance, compared with the sensors according to Comparative Examples.

While the inventive concepts have been described in connection with what is presently considered to be practical embodiments, it is to be understood that the inventive concepts are not limited to such example embodiments. On the contrary, the inventive concepts are intended to cover various modifications and equivalent arrangements included within the spirit and scope of the appended claims.

What is claimed is:

1. A compound represented by Chemical Formula 1:

[Chemical Formula 1]

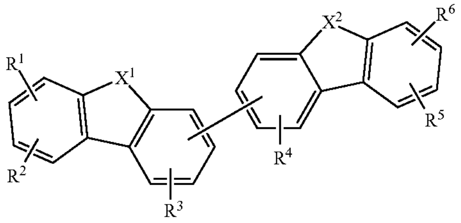

wherein, in Chemical Formula 1, $X^1$ and $X^2$ are different from each other and are each independently $CR^aR^b$, $SiR^cR^d$ or $NR^e$, $R^2$ to $R^5$ are each independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heterocyclic group, a halogen, a cyano group, —$NR^fR^g$, or any combination thereof, $R^a$ to $R^g$ are each independently hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof, $R^a$ and $R^b$ are each independently present or are linked to each other to form a ring, $R^c$ and $R^d$ are each independently present or are linked to each other to form a ring, $R^f$ and $R^g$ are each independently present or are linked to each other to form a ring, and $R^1$ and $R^6$ are each —$NR^fR^g$, wherein $R^f$ and $R^g$ are each a substituted or unsubstituted C6 to C20 aryl group, and $R^f$ and $R^g$ are linked to each other through a single bond, a substituted or unsubstituted C1 to C5 alkylene group, a substituted or unsubstituted C2 to C5 alkenylene group, a substituted or unsubstituted C6 to C20 arylene group, O, S, Se, Te, $CR^hR^i$, $SiR^jR^k$, or $GeR^lR^m$ to form a ring, wherein $R^h$ to $R^m$ are each independently hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof.

2. The compound of claim 1, wherein $X^1$ is $CR^aR^b$ or $SiR^cR^d$, wherein $R^a$ to $R^d$ are each independently hydrogen, a substituted or unsubstituted C1 to C30 alkyl group or a substituted or unsubstituted C6 to C20 aryl group, and $X^2$ is $NR^e$, wherein Re is a substituted or unsubstituted C6 to C20 aryl group.

3. The compound of claim 1, wherein the compound is represented by Chemical Formula 1A:

[Chemical Formula 1A]

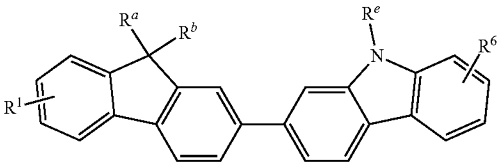

wherein, in Chemical Formula 1A, $R^a$ and $R^b$ are each independently hydrogen, a substituted or unsubstituted C1 to C30 alkyl group or a substituted or unsubstituted C6 to C20 aryl group, $R^e$ is a substituted or unsubstituted C6 to C20 aryl group, and $R^1$ and $R^6$ are each one group of a set of groups listed in Group 1,

[Group 1]

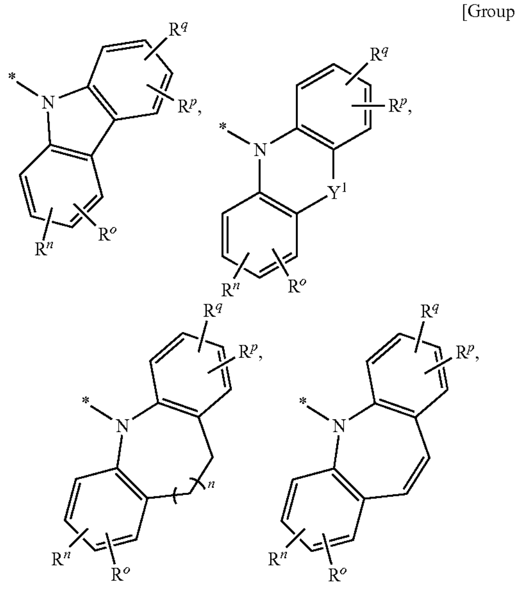

-continued

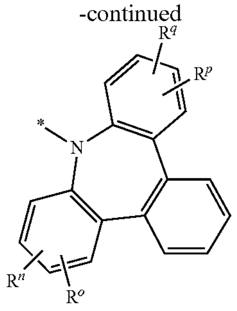

wherein, in Group 1, $Y^1$ is O, S, Se, Te, $CR^hR^i$, $SiR^jR^k$ or $GeR^lR^m$, $R^h$ to $R^q$ are each independently hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof, n is an integer of 0 to 2, and

* is a linking point with Chemical Formula 1A.

4. The compound of claim 1, wherein a glass transition temperature of the compound is about 170° C. to about 400° C., and a LUMO energy level of the compound is about 2.00 eV to about 2.80 eV.

5. A sensor, the sensor comprising:

a first electrode and a second electrode;

a photoelectric conversion layer between the first electrode and the second electrode; and a buffer layer between the first electrode and the photoelectric conversion layer, wherein the buffer layer includes a compound represented by Chemical Formula

[Chemical Formula 1]

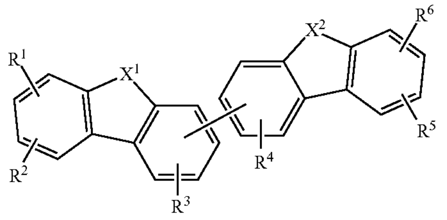

wherein, in Chemical Formula 1, $X^1$ and $X^2$ are different from each other and are each $CR^aR^b$, $SiR^cR^d$, or $NR^e$, $R^2$ to $R^5$ are each independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heterocyclic group, a halogen, a cyano group, —$NR^fR^g$, or any combination thereof, $R^a$ to $R^g$ are each independently hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof, $R^a$ and $R^b$ are each independently present or are linked to each other to form a ring, $R^c$ and $R^d$ are each independently present or are linked to each other to form a ring, $R^f$ and $R^g$ are each independently present or are linked to each other to form a ring, and $R^1$ and $R^6$ are each —$NR^fR^g$, wherein $R^f$ and $R^g$ are each a substituted or unsubstituted C6 to C20 aryl group, $R^f$ and $R^e$ are linked to each other through a single bond, a substituted or unsubstituted C1 to C5 alkylene group, a substituted or unsubstituted C2 to C5 alkenylene group, a substituted or unsubstituted C6 to C20 arylene group, O, S, Se, Te, $CR^hR^i$, $SiR^jR^k$, or $GeR^lR^m$ to form a ring, wherein $R^h$ to $R^m$ are each independently hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof.

6. The sensor of claim 5, wherein $X^1$ is $CR^aR^b$ or $SiR^cR^d$, wherein $R^a$ to $R^d$ are each independently hydrogen, a substituted or unsubstituted C1 to C30 alkyl group or a substituted or unsubstituted C6 to C20 aryl group, and $X^2$ is $NR^e$, wherein $R^e$ is a substituted or unsubstituted C6 to C20 aryl group.

7. The sensor of claim 5, wherein the compound is represented by Chemical Formula 1A:

[Chemical Formula 1A]

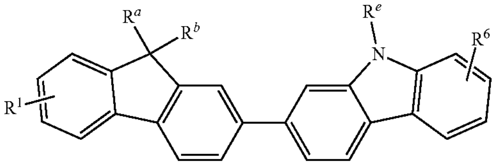

wherein, in Chemical Formula 1A, $R^a$ and $R^b$ are each independently hydrogen, a substituted or unsubstituted C1 to C30 alkyl group or a substituted or unsubstituted C6 to C20 aryl group, $R^e$ is a substituted or unsubstituted C6 to C20 aryl group, and $R^1$ and $R^6$ are each one group of a set of groups listed in Group 1,

[Group 1]

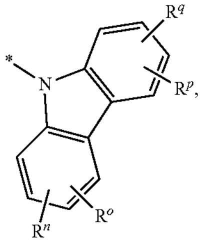

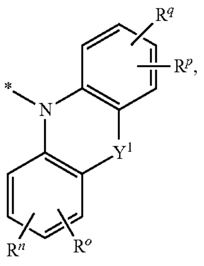

-continued

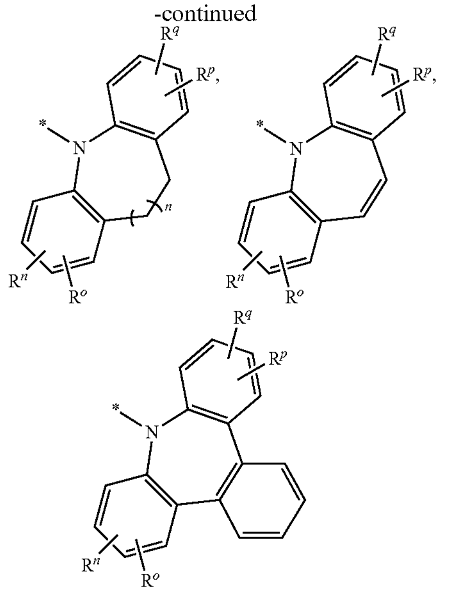

wherein, in Group 1, $Y^1$ is O, S, Se, Te, $CR^hR^i$, $SiR^jR^k$, or $GeR^lR^m$, $R^h$ to $R^q$ are each independently hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof, n is an integer of 0 to 2, and

* is a linking point with Chemical Formula 1A.

8. The sensor of claim 5, further comprising:

a semiconductor substrate, wherein the semiconductor substrate includes circuitry that is electrically connected to the first electrode or the second electrode.

9. A sensor-embedded display panel, comprising:

a substrate;

a light emitting element on the substrate; and a sensor on the substrate, the sensor being in parallel with the light emitting element along an in-plane direction of the substrate such that the sensor and the light emitting element at least partially overlap in the in-plane direction, wherein the sensor includes a first electrode and a second electrode, a photoelectric conversion layer between the first electrode and the second electrode, and a buffer layer between the first electrode and the photoelectric conversion layer, wherein the buffer layer includes a compound represented by Chemical Formula 1:

[Chemical Formula 1]

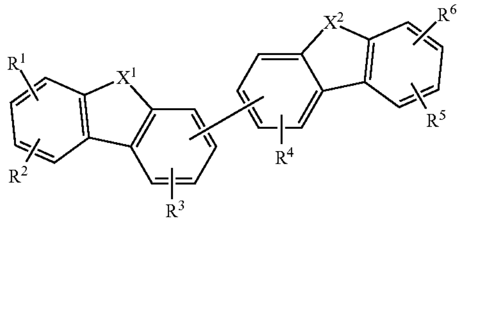

wherein, in Chemical Formula 1, $X^1$ and $X^2$ are different from each other and are each independently $CR^aR^b$, $SiR^cR^d$, or $NR^e$, $R^1$ to $R^6$ are each independently hydrogen, a substituted or unsubstituted C1 to C30 alkyl group, a substituted or unsubstituted C1 to C30 alkoxy group, a substituted or unsubstituted C6 to C20 aryl group, a substituted or unsubstituted C3 to C20 heterocyclic group, a halogen, a cyano group, $-NR^fR^g$, or any combination thereof, at least one of $R^1$ or $R^6$ is a substituted or unsubstituted C6 to C20 aryl group, a substituted or unsubstituted C3 to C20 heterocyclic group, $-NR^fR^g$, or any combination thereof, $R^a$ to $R^g$ are each independently hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof, $R^a$ and $R^b$ are each independently present or are linked to each other to form a ring, $R^c$ and $R^d$ are each independently present or are linked to each other to form a ring, and $R^f$ and $R^g$ are each independently present or are linked to each other to form a ring.

10. The sensor-embedded display panel of claim 9, wherein the light emitting element comprises a plurality of light emitting elements, the plurality of light emitting elements including a first light emitting element, a second light emitting element, and a third light emitting element, the plurality of light emitting elements arranged in parallel along the in-plane direction of the substrate, the plurality of light emitting elements configured to emit light of different wavelength spectra in relation to each other, and the sensor is configured to absorb light generated from at least one of the first light emitting element, the second light emitting element, or the third light emitting element and then reflected by a recognition target to convert the absorbed light into an electrical signal.

11. The sensor-embedded display panel of claim 9, wherein $R^1$ and $R^6$ are each $-NR^fR^g$, wherein $R^f$ and $R^e$ are each a substituted or unsubstituted C6 to C20 aryl group, $R^f$ and $R^g$ are linked to each other through a single bond, a substituted or unsubstituted C1 to C5 alkylene group, a substituted or unsubstituted C2 to C5 alkenylene group, a substituted or unsubstituted C6 to C20 arylene group, O, S, Se, Te, $CR^hR^i$, $SiR^jR^k$, or $GeR^lR^m$ to form a ring, wherein $R^h$ to $R^m$ are each independently hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof.

12. The sensor-embedded display panel of claim 9, wherein $X^1$ is $CR^aR^b$ or $SiR^cR^d$, wherein $R^a$ to $R^d$ are each independently hydrogen, a substituted or unsubstituted C1 to C30 alkyl group or a substituted or unsubstituted C6 to C20 aryl group, and $X^2$ is $NR^e$, wherein $R^e$ is a substituted or unsubstituted C6 to C20 aryl group.

13. The sensor-embedded display panel of claim 9, wherein the compound is represented by Chemical Formula 1A:

[Chemical Formula 1A]

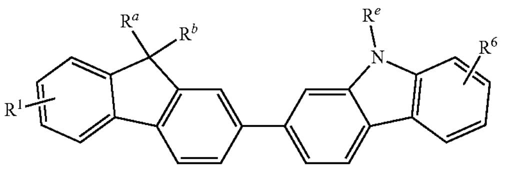

wherein, in Chemical Formula 1A, $R^a$ and $R^b$ are each independently hydrogen, a substituted or unsubstituted C1 to C30 alkyl group or a substituted or unsubstituted C6 to C20 aryl group, $R^e$ is a substituted or unsubstituted C6 to C20 aryl group, and $R^1$ and $R^6$ are each one group of a set of groups listed in Group 1,

[Group 1]

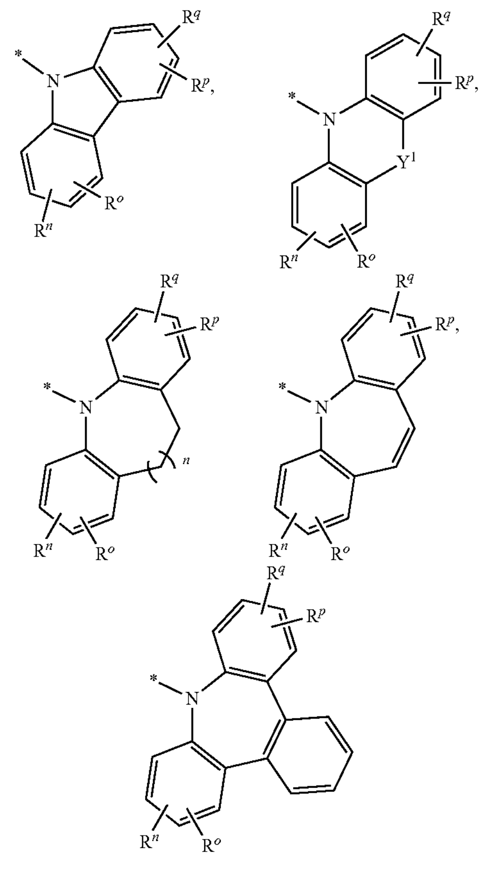

wherein, in Group 1, $Y^1$ is O, S, Se, Te, $CR^hR^i$, $SiR^jR^k$ or $GeR^lR^m$, $R^h$ to $R^q$ are each independently hydrogen, a substituted or unsubstituted C1 to C30 alkyl group, a substituted or unsubstituted C6 to C20 aryl group, a substituted or unsubstituted C3 to C20 heterocyclic group, a halogen, a cyano group, or any combination thereof, n is an integer of 0 to 2, and

* is a linking point with Chemical Formula 1A.

14. The sensor-embedded display panel of claim 9, wherein the light emitting element comprises a third electrode and a fourth electrode, and a light emitting layer between the third electrode and the fourth electrode, and the second electrode of the sensor and the fourth electrode of the light emitting element are a common electrode to which a common voltage is applied.

15. The sensor-embedded display panel of claim 14, further comprising a first common auxiliary layer that is a single piece of material that extends continuously between the third electrode and the light emitting layer and between the first electrode and the buffer layer.

16. The sensor-embedded display panel of claim 15, wherein the first common auxiliary layer is in contact with the buffer layer in the sensor and the light emitting layer in the light emitting element, respectively.

17. The sensor-embedded display panel of claim 15, wherein the buffer layer is thinner than the first common auxiliary layer.

18. The sensor-embedded display panel of claim 14, further comprising a second common auxiliary layer that is a single piece of material that extends continuously between the fourth electrode and the light emitting layer and between the second electrode and the photoelectric conversion layer.

19. The sensor-embedded display panel of claim 14, wherein the light emitting layer comprises an organic light emitter, a quantum dot, a perovskite, or any combination thereof, and the photoelectric conversion layer comprises an organic photoelectric conversion material.

20. The sensor-embedded display panel of claim 9, wherein

The light emitting element comprises a plurality of light emitting elements, the plurality of light emitting elements including a first light emitting element, a second light emitting element, and a third light emitting element, the plurality of light emitting elements each configured to emit light in any one of a red wavelength spectrum, a green wavelength spectrum, or a blue wavelength spectrum, and the photoelectric conversion layer is configured to absorb light having a same wavelength spectrum as light emitted from at least one of the first light emitting element, the second light emitting element, or the third light emitting element.

21. The sensor-embedded display panel of claim 9, wherein the sensor-embedded display panel comprises a display area configured to display a color, and a non-display area excluding the display area, and the sensor is in the non-display area.

22. The sensor-embedded display panel of claim 21, wherein the light emitting element comprises a plurality of light emitting elements, the plurality of light emitting elements including a first light emitting element, a second light emitting element, and a third light emitting element, the plurality of light emitting elements each configured to emit light of any one of a red wavelength spectrum, a green wavelength spectrum, or a blue wavelength spectrum, the display area comprises a plurality of first subpixels configured to display red, the plurality of first subpixels including the first light emitting element, a plurality of second subpixels configured to display green, the plurality of second subpixels including the second light emitting element, and a plurality of third subpixels configured to display blue, the plurality of third subpixels including the third light emitting element, and the sensor is between at least two selected from the plurality of first subpixels, the plurality of second subpixels, or the plurality of third subpixels.

23. An electronic device comprising the sensor of claim 5.

24. An electronic device comprising the sensor-embedded display panel of claim 9.

* * * * *